US006469006B1

United States Patent
Blair et al.

(10) Patent No.: US 6,469,006 B1
(45) Date of Patent: *Oct. 22, 2002

(54) ANTIVIRAL INDOLEOXOACETYL PIPERAZINE DERIVATIVES

(75) Inventors: Wade S. Blair, Clinton; Milind Deshpande, Madison; Haiquan Fang, Wallingford; Pin-Fang Lin, Branford; Timothy P. Spicer, Wethersfield; Owen B. Wallace, Madison; Hui Wang; Tao Wang, both of Middletown; Zhongxing Zhang, Madison; Kap-Sun Yeung, Middletown, all of CT (US)

(73) Assignee: Bristol-Myers Squibb Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/571,460

(22) Filed: May 16, 2000

Related U.S. Application Data

(60) Provisional application No. 60/139,213, filed on Jun. 15, 1999.

(51) Int. Cl.$^7$ .................. A61K 31/497; A61K 31/495; C07D 239/72; C07D 241/36; C07D 401/00

(52) U.S. Cl. .................. 514/253.09; 514/246; 514/248; 514/249; 514/252.13; 514/253.03; 514/253.06; 514/258.1; 544/180; 544/193.2; 544/215; 544/216; 544/235; 544/253; 544/283; 544/284; 544/349; 544/353; 544/359; 544/362; 544/363; 544/366; 544/373

(58) Field of Search .................. 514/246, 248, 514/249, 252.13, 253.03, 253.06, 253.09, 258.1; 544/180, 193.2, 215, 216, 235, 253, 283, 284, 349, 353, 359, 362, 363, 366, 373

(56) References Cited

U.S. PATENT DOCUMENTS

| | | | |
|---|---|---|---|
| 5,124,327 A | * 6/1992 | Greenlee et al. | 514/235.2 |
| 5,192,770 A | * 3/1993 | Clark et al. | 514/305 |
| 5,424,329 A | * 6/1995 | Boschelli et al. | 514/418 |
| 5,681,954 A | * 10/1997 | Yamamoto et al. | 544/114 |

FOREIGN PATENT DOCUMENTS

| | | | |
|---|---|---|---|
| EP | 0484071 A2 | * | 5/1992 |
| EP | 0530907 A1 | * | 3/1993 |
| WO | WO 93/01181 | * | 1/1993 |
| WO | 97/09308 | * | 3/1997 |
| WO | WO 99/55696 | * | 11/1999 |

OTHER PUBLICATIONS

H. Hotoda, "Small–Molecule Inhibitors of HIV–1 Entry Via Chemokine Receptors," Drugs of the Future, 24(12), pp. 1355–1362, 1999.*

J. G. Sodroski, "HIV–1 Entry Inhibitors in the Side Pocket," Cell, 9, pp. 243–246, 1999.*

W. S. Blair, et al, "HIV–1 Entry—An Expanding Portal for Drug Discovery," Drug Discovery Today, 5(5), pp. 183–194, 2000.*

B. A. Larder, et al, "Multiple Mutations in HIV–1 Reverse Transcriptase Confer High–Level Resistance to Zidovudine (AZT)," Science, 246, pp. 1155–1158, 1989.

R. M. Gulick, "Current Antiretroviral Therapy: An Overview," Quality of Life Research, 6, pp. 471–474, 1997.

D. R. Kuritzkes, "HIV Resistance to Current Therapies," Antiviral Therapy, 2(Supplement 3), pp. 61–67, 1997.

S. Morris–Jones, et al, "Antiretroviral Therapies in HIV–1 Infection," Expert Opinion on Investigational Drugs, 6(8), pp. 1049–1061, 1997.

R. F. Schinazi, et al, "Mutations in Retroviral Genes Associated with Drug Resistance," International Antiviral News, 5, pp. 129–142, 1997.

J. P. Vacca, et al, "Clinically Effective HIV–1 Protease Inhibitors," Drug Discovery Today, 2(7), pp. 261–272, 1997.

C. Flexner, "HIV–Protease Inhibitors," Drug Therapy, 338(18), pp. 1281–1292, 1998.

E. DeClercq, "The Role of Non–Nucleoside Reverse Transcriptase Inhibitors (NNRTI's) in the Therapy of HIV–1 Infection," Antiviral Research, 38, pp. 153–179, 1998.

M. Font, et al, "Indoles and Pyridazinol[4,5–b]indoles as Nonnucleoside Analog Inhibitors of HIV–1 Reverse Transcriptase," Eur. J. Med. Chem., 30, pp. 963–971, 1995.

D. L. Romero, et al, J. Med. Chem., 36, pp. 1505–1508, 1993.

S. D. Young, et al, "2–Heterocyclic Indole–3–Sulfones as Inhibitors of HIV–1 Reverse Transcriptase," Bioorg. Med. Chem. Lett., 5(5), pp. 491–496, 1995.

M. J. Genin, et al, "Synthesis and Bioactivity of Novel Bis(Heteroaryl)Piperazine (BHAP) Reverse Transcriptase Inhibitors: Structure–Activity Relationships and Increased Metabolic Stability of Novel Substituted Pyridine Analogs," J. Med. Chem., 39, pp. 5267–5275, 1996.

R. Silvestri, et al, Antiviral Chem. Chemother., 9, pp. 139–148, 1998.

(List continued on next page.)

*Primary Examiner*—Mukund J. Shah
*Assistant Examiner*—Tamthom N. Truong
(74) *Attorney, Agent, or Firm*—Samuel J. DuPoff

(57) ABSTRACT

This invention provides compounds having drug and bio-affecting properties, their pharmaceutical compositions and method of use. In particular, the invention is concerned with indoleoxoacetyl piperazine derivatives. These compounds possess unique antiviral activity, whether used alone or in combination with other antivirals, antiinfectives, immuno-modulators or HIV entry inhibitors. More particularly, the present invention relates to the treatment of HIV and AIDS.

13 Claims, No Drawings

OTHER PUBLICATIONS

A. Fredenhagen, et al, "Semicochliodinol A and B: Inhibitors of HIV–1 Protease and EGF–R Protein Tyrosine Kinease Related Asterriquinones Produced by the Fungus *Chrysosporium Merdarium,*" J. of Antibiotics, 50, pp. 395–401, 1997.

K. Brewster, et al, "Antihypertensive 1,4–bis (2–Indol–3–Ylethyl) Piperazines," Chim. Ther., 8, pp. 169–172, 1973.

J. Archibald, et al, "1,4–Bis (2–Indol–3–Ylethyl) Piperazines," J. Med. Chem., 17, pp. 745–747, 1974.

T. J. Dueweke, et al, "The Binding of a Novel Bisheteroarylpiperazine Mediates Inhibition of Human Immunodeficiency Virus Type 1 Reverse Transcriptase," J. Biol. Chem., 267(1), pp. 27–30, 1992.

T. J. Dueweke, et al, "U–90152, a Potent Inhibitor of Human Immunodeficiency Virus Type 1 Replication," Antimicrob. Agent, Chemother., 37(5), pp. 1127–1131, 1993.

G. W. Gribble, "Recent Developments in Indole Ring Synthesis–Methodology and Applications," Contemp. Org. Synth., 1, pp. 145–172, 1994.

Von Franz Lingens, et al, "Synthese von 3–[Indolyl–(3)] –Glycerin Und 3–[N–Methyl–Indolyl–(3)]–Glycerin," Justus Liebigs Ann. Chem., 738, pp. 46–53, 1970.

M. Desai, et al, "A Convenient Preparation of 1–Aroylpiperazines," Org. Prep. Proced. In., 8(2), pp. 85–86, 1976.

B. J. Potts, "Mini Reverse Transcriptase (RT) Assay," In Aldovini, A., B. D. Walker (ed), Techniques in HIV Research, Stockton Press, NY pp. 103–106, 1990.

O. S. Weislow, et al, "New Soluble–Formazan Assay for HIV–1 Cytopathic Effects: Application to High–Flux Screening of Synthetic and Natural Products for AIDS–Antiviral Activity," Journal of National Cancer Institute, 81(8), pp. 577–586, 1989.

V. A. Johnson, et al, Infectivity Assay, in Aldovini, A., B. D. Walker (ed), Techniques in HIV Research, Stockton Press, NY pp. 71–76, 1990.

S. Harada, et al, "Infection of HTLV–III/LAV in HTLV–I–Carrying Cells MT–2 and MT–4 and Application in a Plaque Assay," Science, 229, pp. 563–566, 1985.

J. D. Behun, et al, "The Chemistry of Pyrazine and Its Derivatives. IV. the Alkylation and Arylation of Methylpyrazine," J. Org. Chem., 26, pp. 3379–3381, 1961.

K. Rossen, et al, Tetrahedron Letters, 36(36), pp. 6419–6422, 1995.

L. W. Jenneskens, et al, "2–(Trifluoromethyl)Piperazine: Synthesis and Characterizatin Using NMR and X–Ray Photoelectron Spectroscopy," J. Recl. Trav. Chim. PAYS–BAS, 114, pp. 97–102, 1995.

T. Wang, et al, "Benzoylation of Dianions: Preparation of Mono–Benzoylated Symmetric Secondary Diamines," J. Org. Chem., 64, pp. 7661–7662, 1999.

M. Adamczyk, et al, "Synthesis of Procainamide Metabolites, N–Acetyl Desethylprocainamide and Desethylprocainamide," Org. Prep. Proced. Int., 28(4), pp. 470–474, 1996.

K. Masuzawa, et al, "Reduction of 4–Benzoyl–2–Piperazinone with Sodium Borohydride in Triethylamine," Bull Chem. Soc. Jpn., 40(1), pp. 244, 1967.

M. Furber, et al, "Studies Relating to the Immunosuppressive Activity of FK506," Tetrahedron Lett., 34(8), pp. 1351–1354, 1993.

G. Bartoli, et al, Tetrahedron Lett., 30(16), pp. 2129–2132, 1989.

G. Bartoli, et al, J. Chem. Soc. Perkin Trans., 1, pp. 2757–2761, 1991.

M. Bosco, et al, J. Chem. Soc. Perkin Trans., 2, pp. 657–663, 1991.

B. K. Chen, et al, J. Virol, 68(2), pp. 654–660, 1994.

* cited by examiner

ANTIVIRAL INDOLEOXOACETYL PIPERAZINE DERIVATIVES

CROSS REFERENCE TO RELATED APPLICATION

This application claims the benefit of U.S. Provisional Application No. 60/139,213 filed Jun. 15, 1999.

BACKGROUND OF THE INVENTION

1. Field of the Invention

This invention provides compounds having drug and bio-affecting properties, their pharmaceutical compositions and method of use. In particular, the invention is concerned with indoleoxoacetyl piperazine derivatives. These compounds possess unique antiviral activity, whether used alone or in combination with other antivirals, antiinfectives, immunomodulators or HIV entry inhibitors. More particularly, the present invention relates to the treatment of HIV and AIDS.

2. Background Art

HIV-1 (human immunodeficiency virus-1) infection remains a major medical problem, with an estimated 33.4 million people infected worldwide. Currently available HIV drugs include six nucleoside reverse transcriptase (RT) inhibitors (zidovudine, didanosine, stavudine, lamivudine, zalcitabine and abacavir), three non-nucleoside reverse transcriptase inhibitors (nevirapine, delavirdine and efavirenz) as well as five peptidomimetic protease inhibitors (saquinavir, indinavir, ritonavir, nelfinavir and amprenavir). Each of these drugs can only transiently restrain viral replication if used alone. However, when used in combination, these drugs have a profound effect on disease progression. In fact, significant reductions in death rates among AIDS patients have been recently documented. Despite these results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when suboptimal drug concentrations are present (Larder and Kemp, Gulick, Morris-Jones, et al, Kuritzkes, Vacca and Condra, Schinazi, et al and Flexner, Ref. 6–12). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors have recently gained an increasingly important role in the therapy of HIV infections. At least 30 different classes of NNRTIs have been published in the literature (DeClercq, Ref. 13). Dipyridodiazepinone (nevirapine), benzoxazinone (efavirenz) and bis(heteroaryl) piperazine derivatives (delavirdine) are already approved for clinical use. In addition, several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1, Williams et al, Ref. 2, Romero et al, Ref. 3, Font et al, Ref. 14, Romero et al, Ref. 15, Young et al, Ref. 16, Genin et al, Ref. 17, and Silvestri et al, Ref. 18).

Indole 2-carboxamides have also been described as inhibitors of cell adhesion and HIV infection (Boschelli et al. in U.S. Pat. No. 5,424,329, Ref. 4). Finally, 3-substituted indole natural products (Semicochliodinol A and B, didemethylasterriquinone and isocochliodinol) were disclosed as inhibitors of HIV-1 protease (Fredenhagen et al, Ref. 19). However, nothing in these references can be construed to disclose or suggest the novel compounds of this invention and their use to inhibit antiviral infection, including HIV infection.

Structurally related compounds have been disclosed previously (Brewster et al, Ref. 20, Archibald et al, Ref. 21, American Home Products in GB 1126245, Ref. 5). However, the structures differ from those claimed herein in that they are symmetrical bis(3-indolylglyoxamides) rather than unsymmetrical aroyl indoleoxoacetyl piperazine derivatives, and there is no mention of use for treating antiviral infections. Interestingly, the indole moiety present in the compounds disclosed here is the common feature of many non-nucleoside HIV-1 reverse transcriptase inhibitors including Delavirdine from Upjohn (Dueweke et al. 1992, 1993, Ref. 22 and 23).

Additionally, the following compounds are available commercially but have not been reported as being useful as pharmaceuticals, and more specifically for antiviral use in mammals.

Compound LJ952 (available from Menai Organics Ltd., Gwynedd, North Wales):

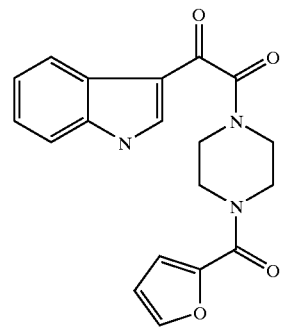

Compound TRI-29586 (available from Tripos):

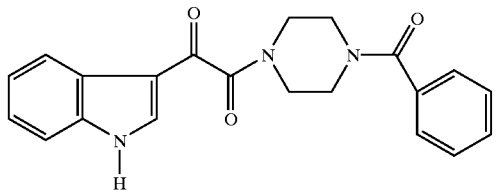

REFERENCES CITED

Patent Documents

1. Greenlee, W. J.; Srinivasan, P. C., Indole reverse transcriptase inhibitors. U.S. Pat. No. 5,4124,327.
2. Williams, T. M.; Ciccarone, T. M.; Saari, W. S.; Wai, J. S.; Greenlee, W. J.; Balani, S. K.; Goldman, M. E.; Theohrides, A. D., Indoles as inhibitors of HIV reverse transcriptase. European Patent 530907.
3. Romero, D. L.; Thomas, R. C., Preparation of substituted indoles as anti-AIDS pharmaceuticals. PCT WO 93/01181.

4. Boschelli, D. H.; Connor, D. T.; Unangst, P. C., Indole-2-carboxamides as inhibitors of cell adhesion. U.S. Pat. No. 5,424,329.
5. Therapeutic bis(indolyl) compounds. British Patent 1126245 (American Home Products Corp.).

OTHER PUBLICATIONS

6. Larder B. A & Kemp S. D., Multiple mutations in the HIV-1 reverse transcriptase confer high-level resistance to zidovudine (AZT), Science, 246:1155–1158, 1989.
7. Gulick R. M., Current antiretroviral therapy: an overview., Quality of Life Research, 6:471–474, 1997.
8. Kuritzkes D. R., HIV resistance to current therapies, Antiviral Therapy, 2(Supplement 3):61–67, 1997.
9. Morris-Jones S, Moyle G & Easterbrook P. J., Antiretroviral therapies in HIV-1 infection, Expert Opinion on Inzestigational Drugs, 6(8):1049–1061, 1997.
10. Schinazi R. F, Larder B. A & Mellors J. W., Mutations in retroviral genes associated with drug resistance, International Antiviral News, 5:129–142, 1997.
11. Vacca J. P & Condra J. H., Clinically effective HIV-1 protease inhibitors, Drug Discovery Today, 2:261–272, 1997.
12. Flexner D., HIV-protease inhibitors, Drug Therapy, 338:1281–1292, 1998.
13. De Clercq E., The role of non-nucleoside reverse transcriptase inhibitors (NNRTIs) in the therapy of HIV-1 infection, Antiviral Research Vol. 38 pp. 153–179, 1998.
14. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F., Indoles and pyrazino[4,5-b]indoles as nonnucleoside analog inhibitors of HIV-1 reverse transcriptase, Eur. J. Med. Chem., 30, 963–971, 1995.
15. Romero, D. L.; Morge, R. A.; Genin, M. J.; Biles, C.; Busso, M,; Resnick, L.; Althaus, I. W.; Reusser, F.; Thomas, R. C and Tarpley, W. G., Bis(heteroaryl) piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate, J. Med. Chem., 36, 1505–1508,1993.
16. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase, Bioorg. Med. Chem. Lett, 5, 491–496, 1995.
17. Genin, M. J.; Poel, T. J.; Yagi, Y.; Biles, C.; Althaus, I.; Keiser, B. J.; Kopta, L. A.; Friis, J. M.; Reusser, F.; adams, W. J.; Olmsted, R. A.; Voorman, R. L.; Thomas, R. C. and Romero, D. L., Synthesis and bioactivity of novel bis (heteroaryl)piperazine (BHAP) reverse transcriptase inhibitors: structure-activity relationships and increased metabolic stability of novel substituted pyridine analogs, J. Med. Chem., 39, 5267–5275,1996.
18. Silvestri, R.; Artico, M.; Bruno, B.; Massa, S.; Novellino, E.; Greco, G.; Marongiu, M. E.; Pani, A.; De Montis, A and La Colla, P., Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. Antiviral Chem. Chemother., 9, 139–148, 1998.
19. Fredenhagen, A.; Petersen, F.; Tintelnot-Blomley, M.; Rosel, J.; Mett, H and Hug, P. J., Semicochliodinol A and B: inhibitors of HIV-1 protease and EGF-R protein Tyrosine Kinase related to Asterriquinones produced by the fungus Chrysosporium nerdarium, Antibiotics, 50, 395–401, 1997.
20. Brewster, K.; Green, D. M.; Pinder, R. M.; Thompson, P. B. J., Antihypertensive 1,4-bis(2-indol-3-ylethyl) piperazines, Chim. Ther., 8, 169–72, 1973.
21. Archibald, John L.; Freed, Meier E., 1,4-Bis(2-indol-3-ylethyl)piperazines, J. Med Chem., 17, 745–7, 1974.
22. Dueweke T. J. et al, The binding of a novel bisheteroaryliperazine mediates inhibition of human immunodeficiency virus type 1 reverse transcriptase, J Biol. Chem. Vol. 267 pp27–30,1992.
23. Dueweke T. J. et al, U-90152, a potent inhibitor of human immunodeficiency virus replication, Antimicrob. Agent. Chemother. Vol. 37 pp1127–1131, 1993.
24. Gribble, G. W., Recent developments in indole ring synthesis-methodology and applications, Contemp. Org. Synth., 1, 145–72 1994.
25. Lingens, F.; Lange, J., Synthesis of 3-indol-3-ylglycerol and of 3-(N-methylindol-3-yl)glycerol., Justus Liebigs Ann. Chem., 738, 46–53, 1970.
26. Desai, M.; Watthey, J. W. H.; Zuckerman, M., A convenient preparation of 1-aroylpiperazines, Org. Prep. Proced. Int., 8, 85–6, 1976.
27. Potts, B. J., Mini Reverse transcriptase (RT) assay, In Aldovini A., B. D. Walker (ed), Techniques in HIV Research, Stockton Press, NY, p. 103–106, 1990.
28. Weislow, O. S., R. Kiser, D. L. Fine, J. Bader, R. H. Shoemaker, and Boyd, M. R., New soluble-formazan assay for HIV-1 cytopathic effects: application to high-flux screening of synthetic and natural products for AIDS-antiviral activity, Journal of National Cancer Institute 81:577–586, 1989.
29. Johnson, V. A. and R. E. Byrington, Infectivity assay, p. 71–76 in A. Aldovini and B. D. Walker (ed), techniques in HIV Research, Stockton Press, New York, 1990.
30. Harada, S., Koyanagi, Y., and N. Yamamoto, Infection of HTLV-III/LAV in HTLV-I carrying cells MT-2 and MT-4 and application in a plaque assay, Science 229:563–566, 1985.
31. (a) Behun, J. D.; Levine, R. J. Org. Chem. 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. Tetrahedron Lett., 1995, 36, 6419–6422. (c) Jenneskens, L. W.; Mahy, J.; den Berg, E. M. M. de B.-v.; Van der Hoef, I.; Lugtenburg, J. Recl. Trap. Cluim. Pays-Bas 1995, 114, 97.
32. Wang, T.; Zhang, Z.; Meanwell, N. A. Benzoylation of Dianions: Preparation of mono-Benzoylated Symmetric Secondary Diamines. J. Org. Chem., 1999, 64, 7661–7662.
33. (a) Adamczyk, M.; Fino, J. R. Synthesis of procainamide metabolites. N-acetyl desethylprocainamide and desethylprocainamide. Org. Prep. Proced. Int. 1996, 28, 470474. (b) Wang, T.; Zhang, Z.; Meanwell, N. A. Regioselective mono-Benzoylation of Unsymmetrical Piperazines. J. Org. Chem., in press.
34. Masuzawa, K.; Kitagawa, M.; Uchida, H. Bull Chem. Soc. Jpn. 1967, 40, 244–245.
35. Furber, M.; Cooper, M. E.; Donald, D. K. Tetrahedron Lett. 1993, 34, 1351–1354.
36. Bartoli et al. a) Tetrahedron Lett. 1989, 30, 2129. b) J. Chem. Soc. Perkin Trans. 1 1991, 2757. c) J. Chem. Soc. Perkin Trans. II 1991, 657.

37. Chen, B. K., Saksela, K., Andino, R., and D. Baltimore. 1994. Distinct modes of human immunodeficiency type 1 proviral latency revealed by superinfection of nonproductively infected cell lines with recombinant luciferase-encoding viruses. J. Virol. 68:654–660.

SUMMARY DESCRIPTION OF THE INVENTION

It has now been surprisingly found that compounds of formula I, or pharmaceutically acceptable salts thereof, are effective antiviral agents, particularly for treating HIV, whether used alone or in combination with other antivirals, antiinfectives, immunomodulators or HIV entry inhibitors.

The present invention comprises compounds of formula I, or pharmaceutically acceptable salts thereof,

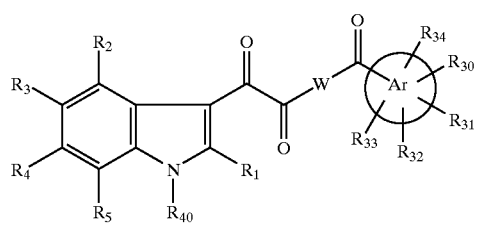

I wherein:
$R_1$, $R_2$, $R_3$, $R_4$ and $R_5$ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, halogen, CN, nitro, $COOR_6$ or $XR_7$, each of said alkyl and cycloalkyl being optionally substituted with one to three same or different halogen, amino, OH, CN or $NO_2$;

$R_6$ is H, $C_1$–$C_6$ alkyl, or $C_3$–$C_6$ cycloalkyl, benzyl, each of said alkyl, cycloalkyl and benzyl being optionally substituted with one to three same or different halogen, amino, OH, CN or $NO_2$;

X is O, S or $NR_6R_7$;

$R_7$ is H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl or $C(O)R_8$, each of said alkyl and cycloalkyl being optionally substituted with one to three same or different halogen, OH, amino, CN or $NO_2$;

$R_8$ is H, $C_1$–$C_6$ alkyl or $C_3$–$C_6$ cycloalkyl;

—W— is

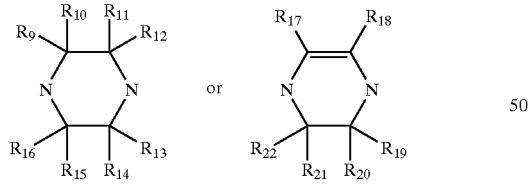

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, $CR_{23}R_{24}OR_{25}$, $COR_{26}$, $COOR_{27}$ or $C(O)NR_{28}R_{29}$, each of said alkyl and cycloalkyl being optionally substituted with one to three same or different halogen, amino, OH, CN or $NO_2$;

$R_{23}$, $R_{24}$, $R_{25}$, $R_{26}$, $R_{27}$, $R_{28}$, $R_{29}$ are each independently H, $C_1$–$C_6$ alkyl, $C_3$–$C_6$ cycloalkyl, $C_2$–$C_6$ alkenyl, $C_3$–$C_6$ cycloalkenyl or $C_2$–$C_6$ alkynyl;

Ar is a 4–7 membered aromatic ring which may contain one to five heteroatoms independently selected from the group consisting of O, S, N or $NR_6$, wherein said aromatic ring is optionally fused to group B;

B is an aromatic group selected from the group consisting of phenyl, 1-naphthyl, 2-naphthyl, indenyl, azulenyl, fluorenyl, and anthracenyl; or a heteroaryl group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimnidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

B and said 4–7 membered aromatic ring may each independently contain one to five substituents which are each independently selected from $R_{30}$ $R_{31}$, $R_{32}$, $R_{33}$ or $R_{34}$;

$R_a$ and $R_b$ are each independently H, $C_{1-6}$ alkyl or phenyl;

Z is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and p is 0–2;

$R_{30}$ $R_{31}$, $R_{32}$, $R_{33}$, and $R_{34}$ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, halogen, CN, nitro, C(O) $R_{35}$, $COXR_{36}$, hydroxyl, $COOR_6$, hydroxymethyl, trifluoromethyl, trifluoromethoxy, O—[($C_1$–$C_4$)-straight or branched alkyl], O-benzyl, O-phenyl, 1,2-methylenedioxy, $OC(O)C_{1-6}$ alkyl, $SC(O)C_{1-6}$ alkyl, $S(O)_m$ $C_{1-6}$ alkyl, $S(O)_2$ $NR_aR_b$, amino, carboxyl, O-Z, $CH_2$—$(CH_2)_p$-Z, O—$(CH_2)_p$-Z, $(CH_2)_p$—O-Z, CH=CH-Z or $XR_{37}$, each of said alkyl and cycloalkyl being optionally substituted with one to three same or different halogen, amino, OH, CN or $NO_2$;

m is 0–2;

$R_{35}$ and $R_{36}$ are each independently H, $C_1$–$C_6$ alkyl or $C_3$–$C_6$ cycloalkyl;

$R_{37}$ is H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, C(O) $R_{38}$ or $C(O)OR_{39}$, each of said alkyl and cycloalkyl being optionally substituted with one to three same or different halogen, amino, OH, CN or $NO_2$;

$R_{38}$, $R_{39}$ are each independently H, $C_1$–$C_6$ alkyl or $C_3$–$C_6$ cycloalkyl, each of said alkyl and cycloalkyl being optionally substituted with one to three same or different halogen, amino, OH, CN or $NO_2$; provided $R_{39}$ is not H;

$R_{40}$ is $(CH_2)_n$—Y, where n is 0–6;

Y is selected from:
(1) H, $C_{1-6}$ alkyl, $C_{3-6}$ cycloalkyl, $C_{2-6}$ alkenyl, $C_{3-6}$ cycloalkenyl, $C_{2-6}$ alkynyl, halogen, CN, nitro, Ar, $COOR_6$, COOAr, —$CONR_aR_b$, $TR_6$, $NR_aR_b$, —$NC(O)NR_aR_b$, —$OC(O)R_6$, —$C[N(R_a)_2]$=N-T-$R_b$, $XR_6$, —$C(O)R_6$, —C(O)Ar, —$S(O)R_a$ or —$S(O)_2R_a$, provided when Y is —$S(O)R_a$ or —$S(O)_2R_a$ then $R_a$ is not H; and
(2) a 4–7 membered heterocyclic ring, optionally substituted with $R_6$, which may contain 1–3 heteroatoms selected from the group consisting of O, S, SO, $SO_2$, N, and $NR_{41}$, wherein $R_{41}$ is selected from the group consisting of hydrogen, $(C_1-C_4)$-straight or branched alkyl, $(C_2-C_4)$-straight or branched alkenyl or alkynyl;

T is S or O;

provided $R_1-R_5$, $R_9-R_{16}$ and $R_{30}-R_{34}$ are not all H at the same time and Ar is phenyl; and provided $R_1-R_5$, $R_9-R_{16}$ and $R_{30}-R_{34}$ are not all H at the same time and Ar is 2-furyl.

Another embodiment of the invention is a pharmaceutical formulation which comprises an antiviral effective amount of a compound of formula I.

Another embodiment of the invention is a pharmaceutical formulation useful for treating infection of HIV which additionally comprises an antiviral effective amount of an AIDS treatment agent selected from the group consisting of:

(a) an AIDS antiviral agent;

(b) an anti-infective agent;

(c) an immunomodulator; and (d) HIV entry inhibitors.

Another embodiment of the invention is a method for treating mammals infected with a virus (e.g. HIV), comprising administering to said mammal an antiviral effective amount of a compound of formula II, or pharmaceutically acceptable salts thereof,

II wherein:

$R_1$, $R_2$, $R_3$, $R_4$ and $R_5$ are each independently H, $C_1-C_6$ alkyl, $C_3-C_6$ cycloalkyl, $C_2-C_6$ alkenyl, $C_3-C_6$ cycloalkenyl, $C_2-C_6$ alkynyl, halogen, CN, nitro, $COOR_6$ or $XR_7$, each of said alkyl and cycloalkyl being optionally substituted with one to three same or different halogen, amino, OH, CN or $NO_2$;

$R_6$ is H, $C_1-C_6$ alkyl, or $C_3-C_6$ cycloalkyl, benzyl, each of said alkyl, cycloalkyl and benzyl being optionally substituted with one to three same or different halogen, amino, OH, CN or $NO_2$;

X is O, S or $NR_6R_7$;

$R_7$ is H, $C_1-C_6$ alkyl, $C_3-C_6$ cycloalkyl, $C_2-C_6$ alkenyl, $C_3-C_6$ cycloalkenyl, $C_2-C_6$ alkynyl or $C(O)R_8$, each of said alkyl and cycloalkyl being optionally substituted with one to three same or different halogen, OH, amino, CN or $NO_2$;

$R_8$ is H, $C_1-C_6$ alkyl or $C_3-C_6$ cycloalkyl;

—W— is $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ are each independently H, $C_1-C_6$ alkyl, $C_3-C_6$ cycloalkyl, $C_2-C_6$ alkenyl, $C_3-C_6$ cycloalkenyl, $C_2-C_6$ alkynyl, $CR_{23}R_{24}OR_{25}$, $COR_{26}$, $COOR_{27}$ or $C(O)NR_{28}R_{29}$, each of said alkyl and cycloalkyl being optionally substituted with one to three same or different halogen, amino, OH, CN or $NO_2$;

$R_{23}$, $R_{24}$, $R_{25}$, $R_{26}$, $R_{27}$, $R_{28}$, $R_{29}$ are each independently H, $C_1-C_6$ alkyl, $C_3-C_6$ cycloalkyl, $C_2-C_6$ alkenyl, $C_3-C_6$ cycloalkenyl or $C_2-C_6$ alkynyl;

Ar is a 4–7 membered aromatic ring which may contain one to five heteroatoms independently selected from the group consisting of O, S, N or $NR_6$, wherein said aromatic ring is optionally fused to group B;

B is an aromatic group selected from the group consisting of phenyl, 1-naphthyl, 2-naphthyl, indenyl, azulenyl, fluorenyl, and anthracenyl; or a heteroaryl group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

B and said 4–7 membered aromatic ring may each independently contain one to five substituents which are each independently selected from $R_{30}$ $R_{31}$, $R_{32}$, $R_{33}$ or $R_{34}$;

$R_a$ and $R_b$ are each independently H, $C_{1-6}$ alkyl or phenyl;

Z is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and p is 0–2;

$R_{30}$ $R_{31}$, $R_{32}$, $R_{33}$, and $R_{34}$ are each independently H, $C_1-C_6$ alkyl, $C_3-C_6$ cycloalkyl, $C_2-C_6$ alkenyl, $C_3-C_6$ cycloalkenyl, $C_2-C_6$ alkynyl, halogen, CN, nitro, $C(O)R_{35}$, $COXR_{36}$, hydroxyl, $COOR_6$, hydroxymethyl, trifluoromethyl, trifluoromethoxy, $O-[(C_1-C_4)$-straight or branched alkyl], O-benzyl, O-phenyl, 1,2-methylenedioxy, $OC(O)C_{1-6}$ alkyl, $SC(O)C_{1-6}$ alkyl, $S(O)_m$ $C_{1-6}$ alkyl, $S(O)_2$ $NR_aR_b$, amino, carboxyl, O-Z, $CH_2—(CH_2)_p$-Z, $O-(CH_2)_p$-Z, $(CH_2)_p$-O-Z, CH=CH-Z or $XR_{37}$, each of said alkyl and cycloalkyl being optionally substituted with one to three same or different halogen, amino, OH, CN or $NO_2$;

m is 0–2;

$R_{35}$ and $R_{36}$ are each independently H, $C_1-C_6$ alkyl or $C_3-C_6$ cycloalkyl;

$R_{37}$ is H, $C_1-C_6$ alkyl, $C_3-C_6$ cycloalkyl, $C_2-C_6$ alkenyl, $C_3-C_6$ cydloalkenyl, $C_2-C_6$ alkynyl, $C(O)R_{38}$ or $C(O)OR_{39}$, each of said alkyl and cycloalkyl being optionally substituted with one to three same or different halogen, amino, OH, CN or $NO_2$;

$R_{38}$, $R_{39}$ are each independently H, $C_1-C_6$ alkyl or $C_3-C_6$ cycloalkyl, each of said alkyl and cycloalkyl being optionally substituted with one to three same or different halogen, amino, OH, CN or $NO_2$; provided $R_{39}$ is not H;

$R_{40}$ is $(CH_2)_n$—Y, where n is 0–6;

Y is selected from:

(1) H, $C_{1-6}$alkyl, $C_{3-6}$ cycloalkyl, $C_{2-6}$ alkenyl, $C_{3-6}$ cycloalkenyl, $C_{2-6}$ alkynyl, halogen, CN, nitro, Ar, $COOR_6$, COOAr, —$CONR_aR_b$, $TR_6$, $NR_aR_b$, —$NC(O)NR_aR_b$, —$OC(O)R_6$, —$C[N(R_a)_2]$=N-T-$R_b$, $XR_6$, —$C(O)R_6$, —$C(O)Ar$, —$S(O)R_a$ or $S(O)_2R_a$, provided when Y is —$S(O)R_a$ or —$S(O)_2R_a$ then $R_a$ is not H; and (2) a 4–7 membered heterocyclic ring, optionally substituted with $R_6$, which may contain 1–3 heteroatoms selected from the group consisting of O, S, SO, $SO_2$, N, and $NR_{41}$, wherein $R_{41}$ is selected from the group consisting of hydrogen, $(C_1-C_4)$-straight or branched alkyl, $(C_2-C_4)$-straight or branched alkenyl or alkynyl; and T is S or O.

In a preferred embodiment, compounds of formula I and II include those where Ar is phenyl, furyl, isoxazolyl, thiophenyl, pyrazolyl, pyridyl, benzofuryl, benzothiophenyl, indolyl, pyrazinyl, thiazolyl, imidazolyl, thiadiazolyl.

Also preferred are compounds of formulas I and II wherein W is

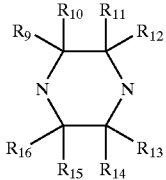

$R_9$, $R_{10}$, $R_{11}$, $R_{12}$, $R_{13}$, $R_{14}$, and $R_{15}$ are each H; and $R_{16}$ is methyl.

Also preferred are compounds of formulas I and II wherein $R_2$ is H, fluoro or methoxy.

Also preferred are compounds of formulas I and II wherein $R_1$, $R_3$ and $R_4$ are each H.

DETAILED DESCRIPTION OF THE INVENTION

The synthesis procedures and anti-HIV-1 activities of the novel indoleoxoacetyl piperazine analogs of formula I are summarized below.

Chemistry

The present invention comprises compounds of formula I, their pharmaceutical formulations, and their use in patients suffering from or susceptible to HIV. The compounds of formula I which include pharmaceutically acceptable salts thereof,

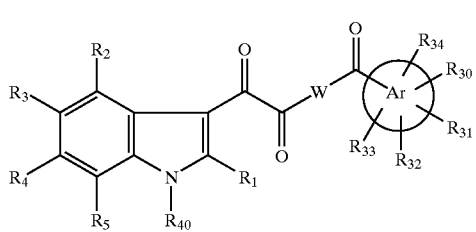

I

The term "$C_{1-6}$ alkyl" as used herein and in the claims (unless the context indicates otherwise) mean straight or branched chain alkyl groups such as methyl, ethyl, propyl, isopropyl, butyl, isobutyl, t-butyl, amyl, hexyl and the like. Similarly, "$C_{2-6}$ alkenyl" and "$C_{2-6}$ alkynyl" include straight or branched chain groups.

The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like.

"Halogen" refers to chlorine, bromine, iodine or fluorine.

In the method of the present invention, the term "antiviral effective amount" means the total amount of each active component of the method that is sufficient to show a meaningful patient benefit, i.e., healing of acute conditions characterized by inhibition of antiviral infection, including HIV infection. When applied to an individual active ingredient, administered alone, the term refers to that ingredient alone. When applied to a combination, the term refers to combined amounts of the active ingredients that result in the desired antiviral effect, whether administered in combination, serially or simultaneously. The terms "treat, treating, treatment" as used herein and in the claims means preventing or ameliorating diseases associated with viral infection, including HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals,

| ANTIVIRALS | | |
|---|---|---|
| Drug Name | Manufacturer | Indication |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |

-continued

ANTIVIRALS

| Drug Name | Manufacturer | Indication |
|---|---|---|
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycyfidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (-)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-440690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony | Schering-Plough | AIDS, combination |

IMMUNOMODULATORS (continued)

| Drug Name | Manufacturer | Indication |
|---|---|---|
| Stimulating Factor | | w/AZT |
| HIV Core Particle Immunostimulant | Rorer | Seropositive HIV |
| IL-2 Interleukin-2 | Cetus | AIDS, in combination w/AZT |
| JL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-LaRoche | Kaposi's sarcoma AIDS, ARC, in combination w/AZT |
| SK & F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |

ANTI-INFECTIVES (continued)

| Drug Name | Manufacturer | Indication |
|---|---|---|
| Spiramycin | Rhone-Poulenc | Cryptosporidial diarrhea |
| Intraconazole-R51211 | Janssen-Pharm. | Histoplasmosis; cryptococcal Meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT Therapy |
| Recombinant Human Growth Hormone | Serono | AIDS-related wasting, cachexia |
| Megestrol Acetate | Bristol-Myers Squibb | Treatment of Anorexia assoc. W/AIDS |
| Testosterone | Alza, Smith Kline | AIDS-related wasting |
| Total Enteral Nutrition | Norwich Eaton Pharmaceuticals | Diarrhea and malabsorption Related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355–1362; CELL, Vol. 9, pp. 243–246, Oct. 29, 1999; and DRUG DISCOVERY TODAY, Vol. 5, No. 5, May 2000, pp. 183–194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Procedures for making compounds of formula I are shown in Schemes 1–13, and further exemplified in Tables 5–8.

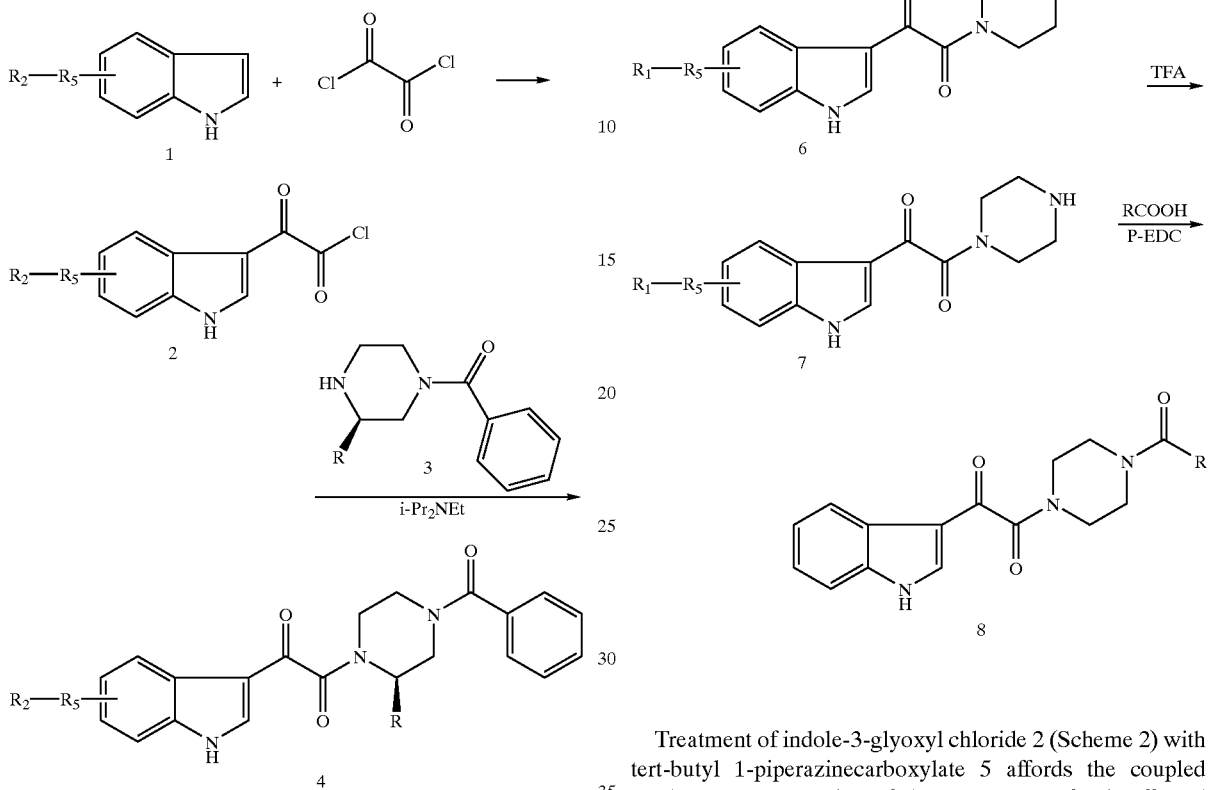

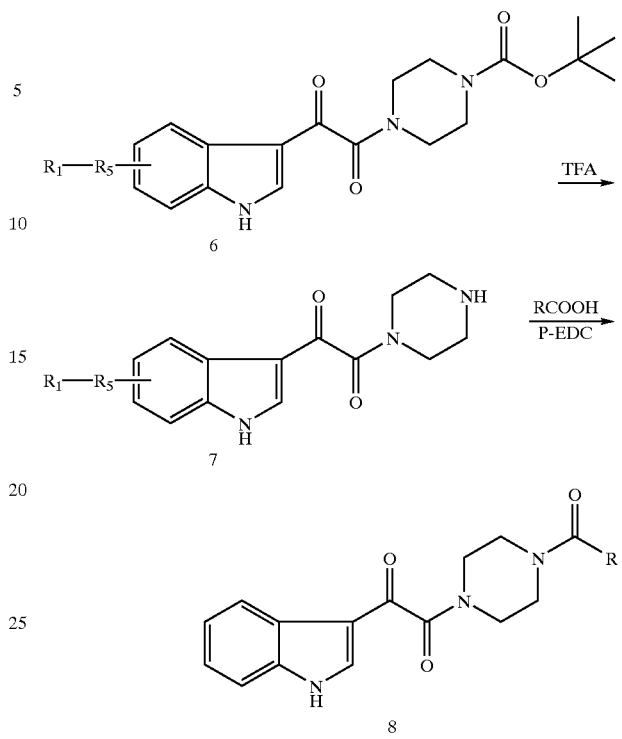

Starting indoles 1 (Scheme 1) are known or are readily prepared according to literature procedures, such as those described in Cribble, G. (Ref. 24) or Bantoli et al (Ref. 36). The indoles 1 are treated with oxalyl chloride in either THF (tetrahydrofuran) or ether to afford the desired glyoxyl chlorides 2 according to literature procedures (Lingens, F. et al, Ref. 25). The intermediate glyoxyl chlorides 2 are then coupled with benzoyl piperazine 3 (Desai, M. et al, Ref. 26) under basic conditions to afford 4.

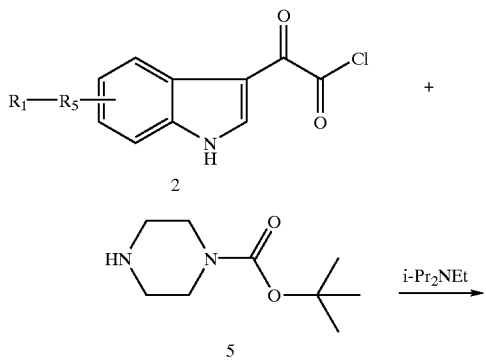

Treatment of indole-3-glyoxyl chloride 2 (Scheme 2) with tert-butyl 1-piperazinecarboxylate 5 affords the coupled product 6. Deprotection of the Boc group of 6 is effected with 20% (trifluoroacetic acid) TFA/CH$_2$Cl$_2$ to yield 7. This product is then coupled with carboxylic acid in the presence of polymer supported 1-(3-Dimethylaminopropyl)-3-ethylcarbodiimide (P-EDC) to afford products 8.

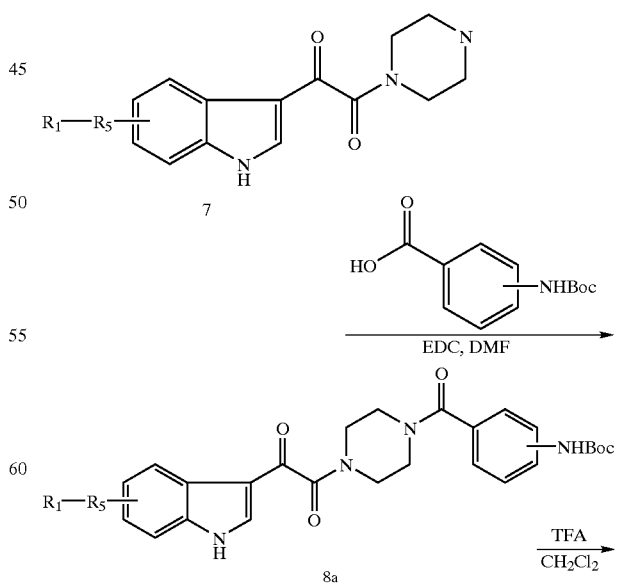

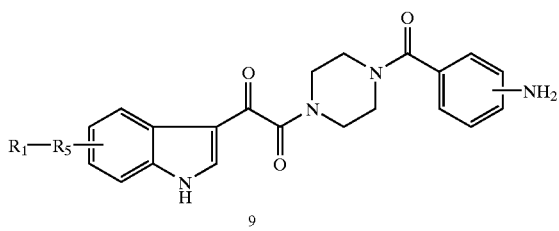

For Examples 58–81, piperazine 7 (Scheme 3) was treated with Boc-protected aminobenzoic acid in the presence of EDC to afford 8a. A portion of the resulting product was separated and subjected to TFA in order to remove the Boc group, thus yielding amino derivatives 9.

Scheme 4

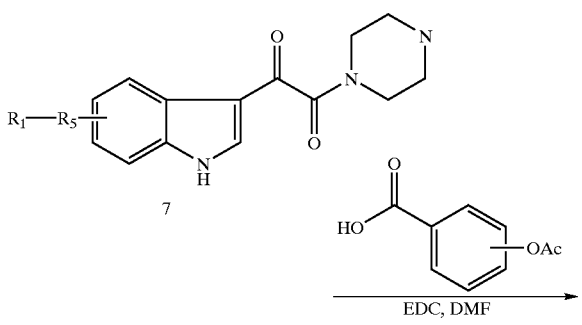

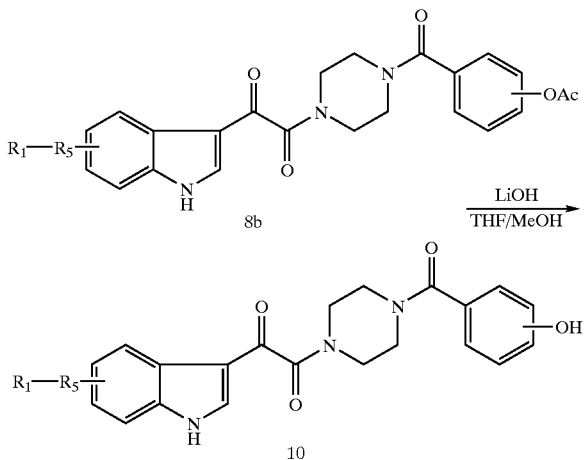

For Examples 82–89, piperazine 7 (Scheme 4) was treated with acetoxybenzoic acid in the presence of EDC to afford 8b. A portion of the resulting product was separated and subjected to LiOM hydrolysis in order to remove the acetate group, thus yielding hydroxy derivatives 10.

Examples containing substituted piperazines are prepared using the general procedures outlined in Schemes 5–13.

Substituted piperazines are either commercially available from Aldrich, Co. or prepared according to literature procedures (Behun et al, Ref. 31(a), Scheme 5, eq. 01). Hydrogenation of alkyl substituted pyrazines under 40 to 50 psi pressure in ethanol afforded substituted piperazines. When the substituent was an ester or amide, the pyrazine systems could be partially reduced to the tetrahydropyrazine (Rossen et al, Ref. 31(b), Scheme 5, eq. 02). The carbonyl substituted piperazines could be obtained under the same conditions described above by using commercially available dibenzyl piperazines (Scheme 5, eq. 03).

Scheme 5

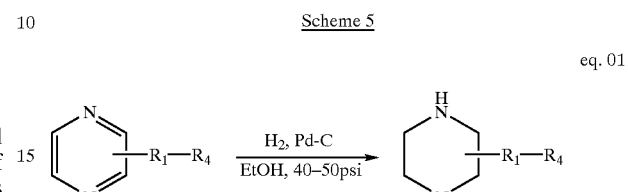

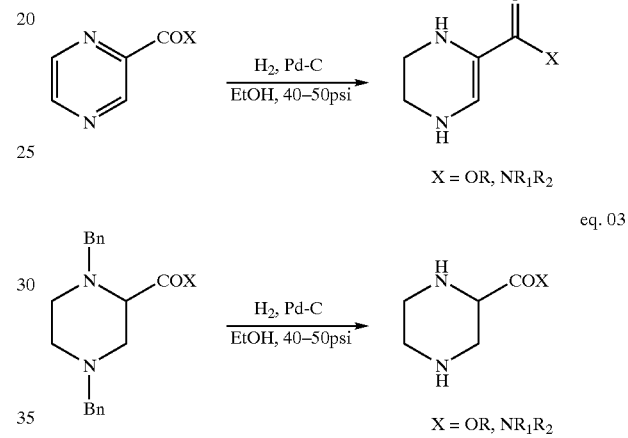

2-Trifluoromethylpiperazine (Jenneskens et al., Ref. 31c) was prepared through a four step route (Scheme 6). Using Lewis acid $TiCl_4$, N,N'-dibenzylethylenediamine 11 reacted with trifluoropyruvates 12 to afford hemiacetal 13, which was reduced at room temperature by $Et_3SiH$ in $CF_3COOH$ to lactam 14. $LiAlH_4$ treatment then reduced lactam 14 to 1,4-dibenzyl-2-trifluoromethylpiperazine 15. Finally, hydrogenation of compound 15 in HOAc gave the desired product 2-trifluoromethylpiperazine 16.

Scheme 6

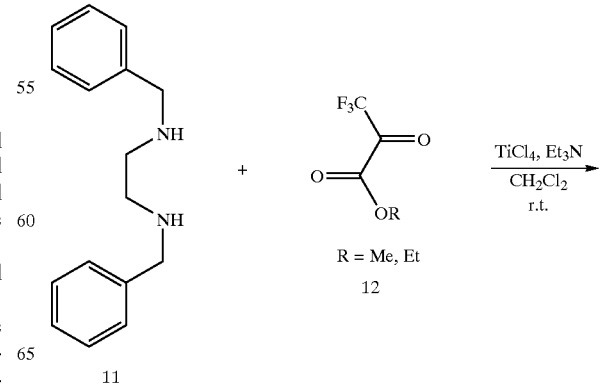

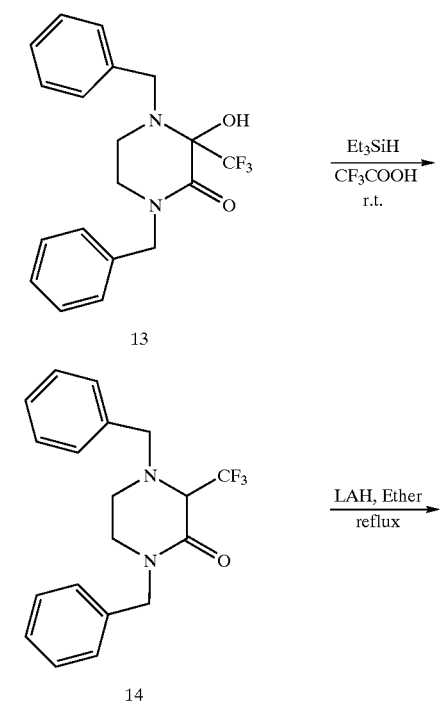

Mono-benzoylation of symmetric substituted piperazines could be achieved by using one of the following procedures (Scheme 7). (a) Treatment of a solution of piperazine in acetic acid with acetyl chloride afforded the desired mon-benzoylated piperazine (Desai et al. Ref. 26, Scheme 7, eq. 04). (b) Symmetric piperazines were treated with 2 equivalents of n-butyllithium, followed by the addition of benzoyl chloride at room temperature (Wang et al, Ref. 32, Scheme 7, eq. 05).

Mono-benzoylation of unsymmetric substituted piperazines could be achieved by using one of the following procedures (Scheme 8), in which all the methods were exemplified by mono-alkyl substituted piperazines. (a) Unsymmetric piperazines were treated with 2 equivalents of n-butyllithium, followed by the addition of benzoyl chloride at room temperature to afford a mixture of two regioisomers, which could be separated by chromatography (Wang et al, Ref. 32 and 33(b), Scheme 8 eq. 06); (b) Benzoic acid was converted to its pentafluorophenyl ester, and then further reaction with 2-alkylpiperazine to provide the mono-benzoylpiperazines with the benzoyl group at the less hindered nitrogen (Adamczyk et al, Ref. 33(a), Scheme 8, eq. 07); (c) A mixture of piperazine and methyl benzoate was treated with dialkylaluminum chloride in methylene chloride for 2–4 days to yield the mono-benzoylpiperazine with the benzoyl group at the less hindered nitrogen (Scheme 8, eq. 08); (d) Unsymmetric piperazines were treated with 2 equivalents of n-butyllithium, followed by subsequent addition of triethylsilyl chloride and benzoyl chloride in THF at room temperature to afford mono-benzoylpiperazines with the benzoyl group at the more hindered nitrogen (Wang et al, Ref. 33(b), Scheme 8, eq. 09). When the substituent at position 2 was a ester or amide, the mono-benzoylation with benzoyl chloride occurred at the less hindered nitrogen of the piperazine with triethylamine as base in THF (Scheme 8, eq. 10).

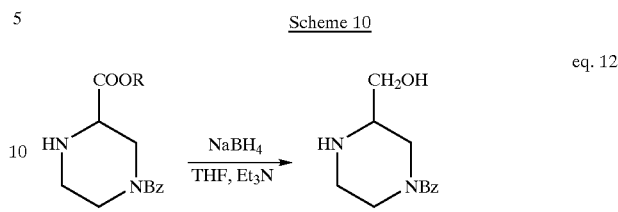

Furthermore, the ester group can be selectively reduced by NaBH$_4$ in the presence of the benzamide (Masuzawa et al, Ref. 34), which is shown in Scheme 10.

Scheme 10

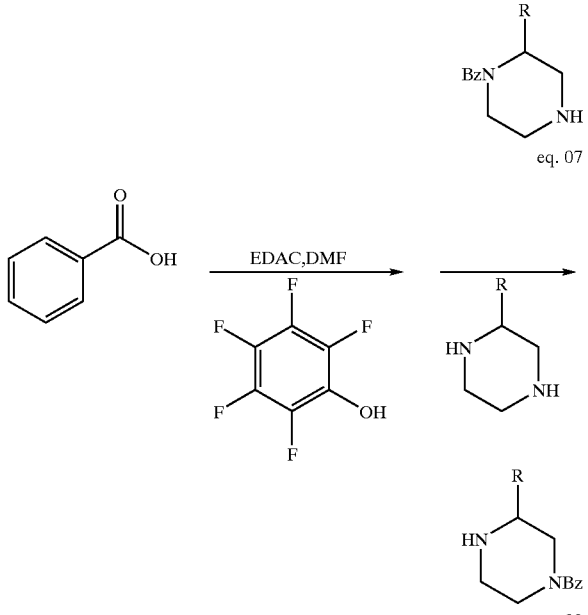

eq. 12

Hydrolysis of Ester Group to Acid:

The ester groups on either the piperazine linkers or on the indole nucleus could be hydrolyzed to the corresponding acid under basic conditions such as K$_2$CO$_3$ (Scheme 11, eq. 13) or NaOMe (Scheme 11, eq. 14) as bases in MeOH and water.

Scheme 11

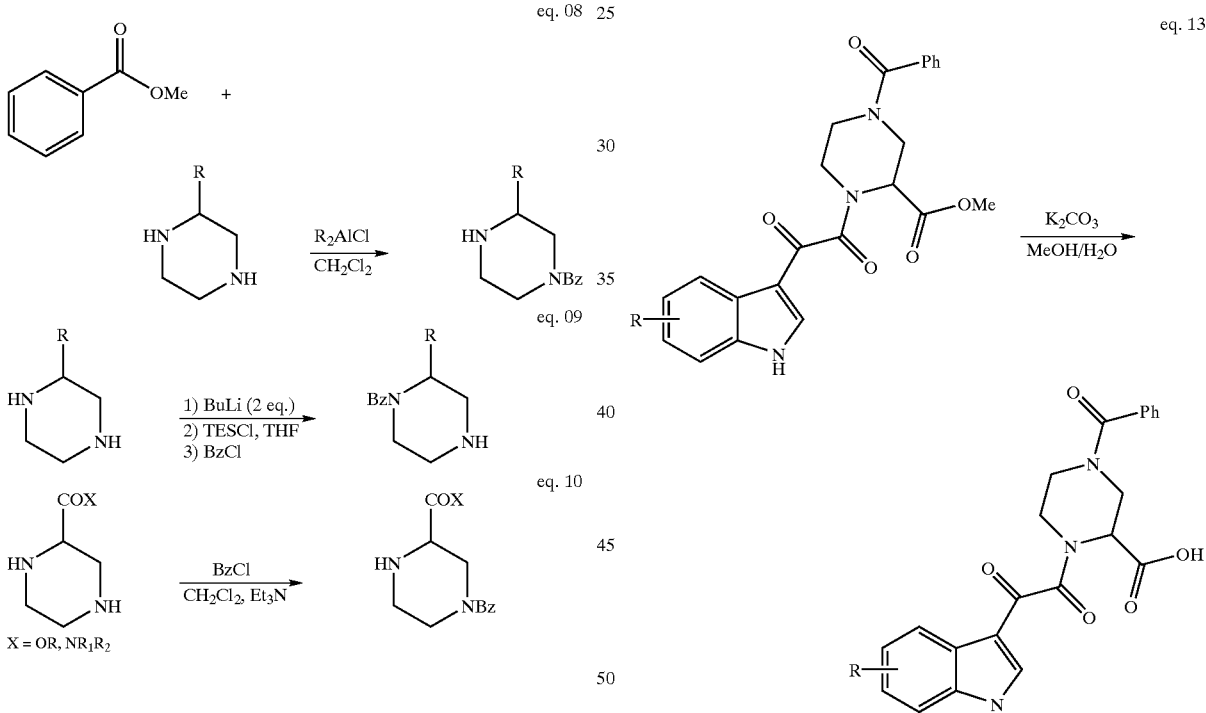

eq. 13

In the case of tetrahydropyrazines (Scheme 9, eq. 11), mono-benzoylation occurred at the more hindered nitrogen under the same conditions as those in equation 10 of Scheme 8, in the well precedented manner. (Rossen et al, Ref. 31(b)).

Scheme 9

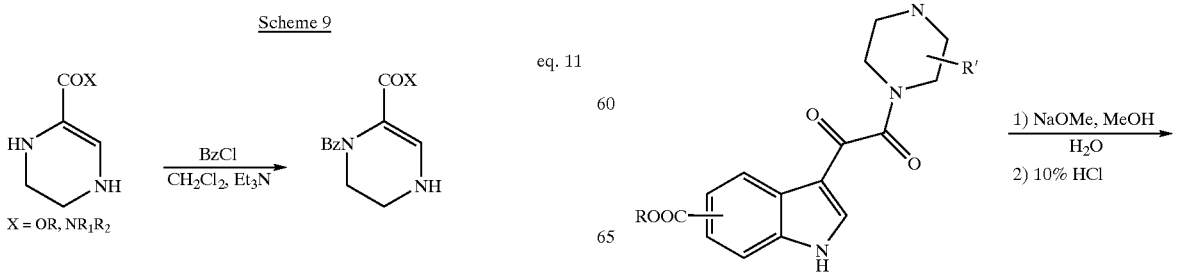

eq. 14

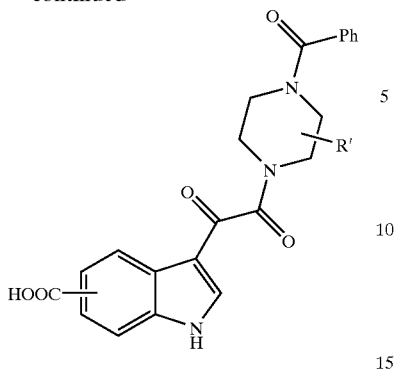

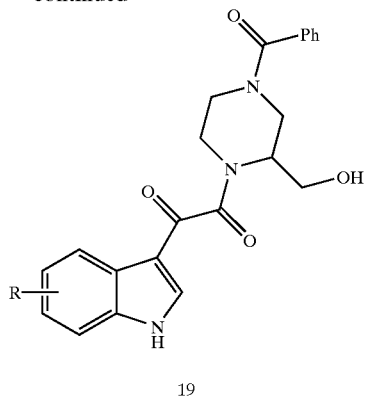

Coupling Reaction:

Scheme 12

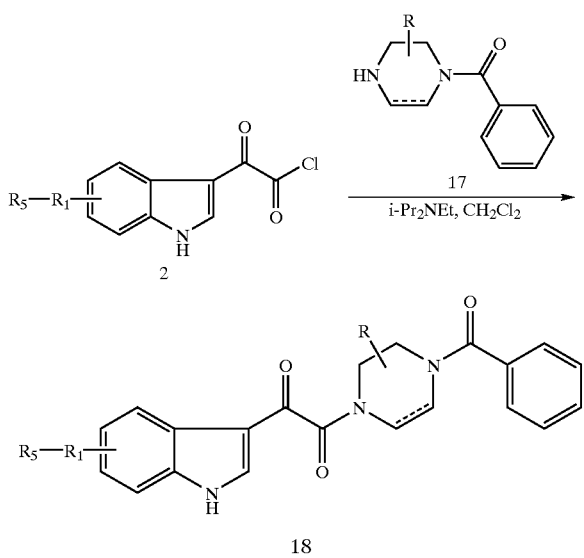

Reaction of glyoxyl chloride 2 with substituted benzoyl piperazines or tetrahydropyrazines (17) in CH2Cl2 using i-Pr2NEt as base afforded the desired products 18.

In the case of coupling reactions using 3-hydroxylmethylbenzoylpiperazine, the hydroxyl group was temporarily protected as its TMS (trimethylsilyl) ether with BSTFA (N,O-bistrimethylsilyl)fluoroacetamide) (Furber et al, Ref. 35). The unprotected nitrogen atom was then reacted with glyoxyl chlorides 2 to form the desired diamides. During workup, the TMS masking group was removed to give free hydroxylmethylpiperazine diamides 19 (Scheme 13).

Scheme 13

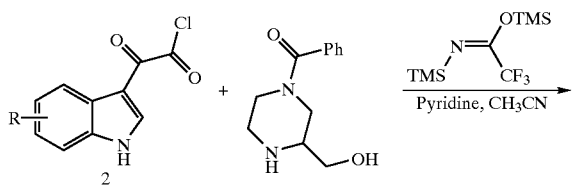

Antiviral Activity

The antiviral activity of the compounds of Examples 1–34 was determined in MT-2 cells (a CD4 positive T-lymphocytic cell line) acutely infected by the BRU strain of HIV-1 in the presence of 10 μM compound. The virus yields were quantitated 6 days after infection using a reverse transcriptase assay (Potts, Ref. 27). The anti-viral results are summarized in Table 1, shown below. Cytotoxicity was determined by incubating cells in the presence of serially diluted compound and cell viability determined using an XTT dye reduction assay (Weislow, Ref. 28). The 50% cytotoxicity concentrations of all compounds were significantly higher than 10 μM, indicating that the compounds are relatively non-toxic.

The antiviral activity of the compounds of Examples 35–215 was determined in HeLa CD4 CCR$_5$ cells infected by single-round infectious HIV-1 reporter virus in the presence of compound at concentrations ≦10 μM. The virus infection was quantified 3 days after infection by measuring luciferase expression from integrated viral DNA in the infected cells (Chen et al, Ref. 41). The percent inhibition for each compound was calculated by quantifying the level of luciferase expression in cells infected in the presence of each compound as a percentage of that observed for cells infected in the absence of compound and subtracting such a determined value from 100. Compounds exhibiting anti-viral activity without appreciable toxicity at concentrations ≦10 μM are presented in Tables 1–4 and 9–13.

TABLE 1

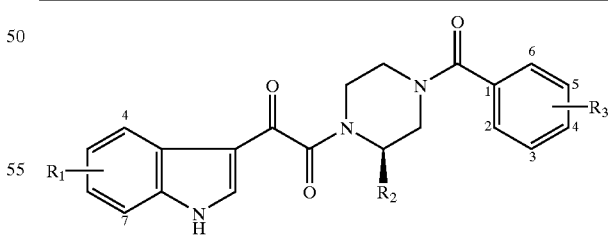

| Example # | $R_1$ | $R_2$ | $R_3$ | % Inhibition @ 10 uM |
|---|---|---|---|---|
| 1 | H | H | H | >98 |
| 2 | H | H | 2,6-Difluoro- | 66.8 |
| 3 | H | H | 2,4-Difluoro- | 28.5 |
| 4 | H | H | 2-Fluoro-3-chloro- | 91.2 |
| 5 | H | H | 2-Fluoro- | >98 |

TABLE 1-continued

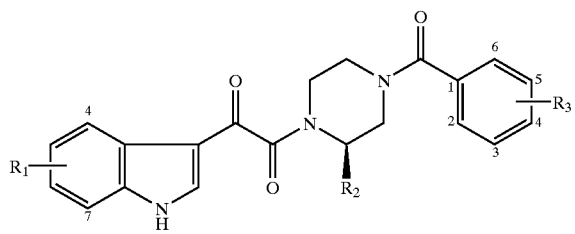

| Example # | R₁ | R₂ | R₃ | % Inhibition @ 10 uM |
|---|---|---|---|---|
| 6 | H | H | 2-Acetoxy- | 65.4 |
| 7 | H | H | 2-Hydroxy- | 88 |
| 8 | H | H | 3-Chloro-4-fluoro- | 46 |
| 9 | H | H | 3-Fluoro-4-methyl- | 23.4 |
| 10 | H | H | 3,4-Difluoro- | 32.7 |
| 11 | H | H | 3-Fluoro- | 92.5 |
| 12 | H | H | 3-Bromo- | 88.4 |
| 13 | H | H | 4-Hydroxy- | 87.7 |
| 14 | H | H | 4-Fluoro- | 73.6 |
| 15 | H | H | 4-Methyl- | 61.8 |
| 16 | H | H | 4-tertButyl- | 47.9 |
| 17 | H | H | 4-Acetoxy- | 91.5 |
| 18 | 2-Methyl- | H | H | 54.9 |
| 19 | 4-Fluoro- | H | H | >98 |
| 20 | 4-Chloro- | H | H | >98 |
| 21 | 4-Nitro- | H | H | 88.3 |
| 22 | 5,6-Diacetoxy- | H | H | 34 |
| 23 | 5-Fluoro- | H | H | 94.6 |
| 24 | 5-Acetoxy- | H | H | 75.8 |
| 25 | 5-Methyl- | H | H | 49.5 |
| 26 | 5-Bromo- | H | H | >98 |
| 27 | 5-Chloro- | H | H | 95.8 |
| 28 | 6-Fluoro- | H | H | >98 |
| 29 | 6-Chloro- | H | H | 95.6 |
| 30 | 6-Methoxy- | H | H | 96.4 |
| 31 | 7-Chloro- | H | H | >98 |
| 32 | 7-Carboethoxy- | H | H | >98 |
| 33 | 7-Ethyl- | H | H | >98 |
| 34 | 7-Methyl- | H | H | >98 |
| 35 | 7-Bromo- | H | H | >98 |
| 36 | 7-Methoxy- | H | H | >98 |
| 37 | 6-Trifluoromethyl- | H | H | 38 |
| 38 | 7-Fluoro- | H | H | >98 |
| 39 | 4,7-Dimethoxy- | H | H | >98 |
| 40 | 5,6-Dichloro- | H | H | >98 |
| 41 | 4-Bromo- | H | H | >98 |
| 42 | 4,6-Difluoro- | H | H | >98 |
| 43 | 5-Fluoro-6-chloro- | H | H | 60 |
| 44 | 5,6-Difluoro- | H | H | 63 |
| 45 | 4,5,6,7-tetrafluoro- | H | H | >98 |
| 46 | 4,7-Difluoro- | H | H | >98 |
| 47 | 4-Methoxy- | H | H | >98 |
| 48 | 5-Fluoro-7-bromo- | H | H | 75 |
| 49 | 4-Fluoro-7-methyl- | H | H | >98 |
| 50 | 4,6-Difluoro-5-Bromo- | H | H | 97 |
| 51 | 4-Fluoro-7-trifluoroethoxy- | H | H | >98 |
| 52 | 4-Methoxy-7-chloro- | H | H | >98 |
| 53 | 4-ethoxy- | H | H | >98 |
| 54 | 4-methoxy-7-bromo- | H | H | >98 |
| 55 | 4-Bromo-7-fluoro- | H | H | 97 |
| 56 | 4-Fluoro-7-methoxy- | H | H | >98 |
| 57 | 4-Trifluoromethoxy-7-bromo- | H | H | >98 |
| 58 | 4-Fluoro- | H | 4-NHC(O)OBu-t | 95 |
| 59 | 4-Chloro- | H | 2-NHC(O)OBu-t | 51 |
| 60 | 4-Chloro- | H | 3-NHC(O)OBu-t | 97 |

TABLE 1-continued

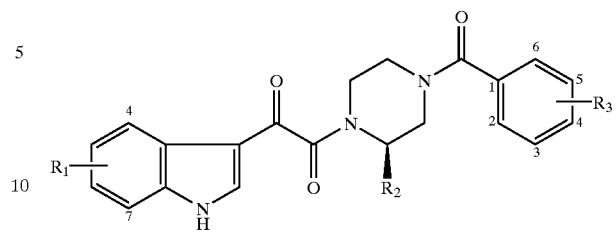

| Example # | R₁ | R₂ | R₃ | % Inhibition @ 10 uM |
|---|---|---|---|---|
| 61 | 4-Chloro | H | 4-NHC(O)OBu-t | 93 |
| 62 | 4-Fluoro | H | 2-NHC(O)OBu-t | 51 |
| 63 | 4-Fluoro | H | 3-NHC(O)OBu-t | 98 |
| 64 | 4-Methoxy | Me | 3-NHC(O)OBu-t | 95 |
| 65 | 4-Fluoro | H | 2-Amino | 84 |
| 66 | 4-Fluoro | H | 3-Amino | >98 |
| 67 | 4-Fluoro | H | 4-Amino | >98 |
| 68 | 4-Chloro | H | 2-Amino | 75 |
| 69 | 4-Chloro | H | 3-Amino | >98 |
| 70 | 4-Chloro | H | 4-Amino | 98 |
| 71 | H | H | 2-Amino | 36 |
| 72 | H | H | 3-Amino | 87 |
| 73 | 4,7-Difluoro | H | 3-Amino | >98 |
| 74 | 4,7-Difluoro | Me | 3-Amino | >98 |
| 75 | 4,7-Difluoro | Me | 4-Amino | >98 |
| 76 | 4-Fluoro | Me | 3-Amino | >98 |
| 77 | 4-Methoxy-7-Chloro | Me | 3-Amino | >98 |
| 78 | 4-Methoxy-7- | Me | 4-Amino | >98 |
| 79 | 4-Methoxy | Me | 3-Amino | >98 |
| 80 | 4-Fluoro-7-Methoxy | Me | 3-Amino | >98 |
| 81 | 4-Fluoro-7-Methoxy | Me | 4-Amino | >98 |
| 82 | 4-Fluoro | H | 2-Acetoxy | 91 |
| 83 | 4-Fluoro | H | 3-Acetoxy | >98 |
| 84 | 4-Fluoro | H | 4-Acetoxy | 98 |
| 85 | 4-Chloro | H | 4-Acetoxy | 93 |
| 86 | 4-Chloro | H | 3-Acetoxy | >98 |
| 87 | 4-Fluoro | H | 2-OH | 86 |
| 88 | 4-Fluoro | H | 3-OH | >98 |
| 89 | 4-Fluoro | H | 4-OH | 95 |
| 90 | 4-Fluoro-7-carboxaldehyde | H | H | >98 |

TABLE 2

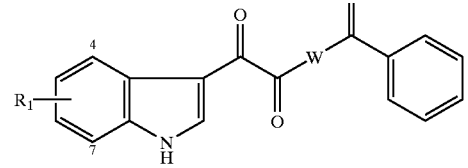

| Example # | R₁ | W | % Inhibition @ 10 uM |
|---|---|---|---|
| 91 | 4-Fluoro |  | >98 |

TABLE 2-continued
| Example # | R₁ | W | % Inhibition @ 10 uM |
|---|---|---|---|
| 92 | 4-Fluoro |  | 94 |
| 93 | 4-Fluoro | 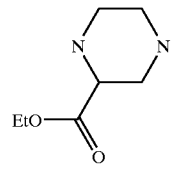 | >98 |
| 94 | 4-Fluoro | 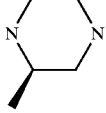 | >98 |
| 95 | 4-Fluoro | 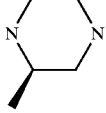 | >98 |
| 96 | 4-Fluoro | 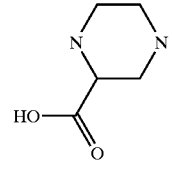 | >98 |
| 97 | 4-Fluoro | 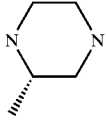 | 97 |
| 98 | 4-COOMe | 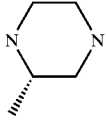 | 84 |
| 99 | 4-Fluoro | 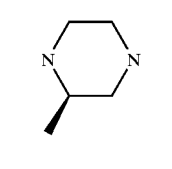 | 89 |
| 100 | 7-COOMe |  | 86 |
| 101 | 4-Fluoro |  | 74 |
| 102 | 7-COOMe | 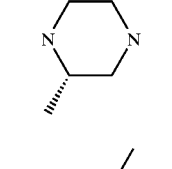 | >98 |
| 103 | 7-COOMe | 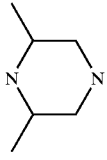 | >98 |
| 104 | 7-COOMe | 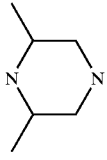 | >98 |
| 105 | 7-OMe | 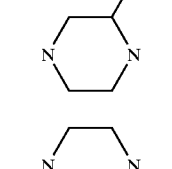 | >98 |
| 106 | 4,7-Difluoro | 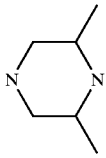 | >98 |
| 107 | 4,5,6,7-tetrafluoro | 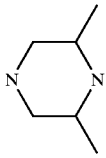 | >98 |
| 108 | 4,5,6,7-tetrafluoro | 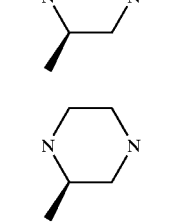 | >98 |

TABLE 2-continued

| Example # | R₁ | W | % Inhibition @ 10 uM |
|---|---|---|---|
| 109 | 7-Nitro | (2-methylpiperazine) | >98 |
| 110 | 7-Ethyl | (2-methylpiperazine) | >98 |
| 111 | 7-OMe | (2-methylpiperazine) | >98 |
| 112 | 7-Nitro | (2-methylpiperazine) | 84 |
| 113 | 6-Chloro | (2-methylpiperazine) | 81 |
| 114 | 5,6-Dichloro | (2-methylpiperazine) | 89 |
| 115 | 4-Chloro | (2-methylpiperazine) | 79 |
| 116 | 4-Chloro | (2-methylpiperazine) | 77 |
| 117 | 5,6-dichloro | (2-methylpiperazine) | 89 |
| 118 | 5-Fluoro | (2-methylpiperazine) | 69 |
| 119 | 7-Ethyl | (2-methylpiperazine) | 72 |
| 120 | 4-Bromo | (2-methylpiperazine) | 58 |
| 121 | 7-COOMe | (methyl pyrazine-2-carboxylate) | 92 |
| 122 | 4-Br | (2-methylpiperazine) | 40 |
| 123 | 5-Fluoro | (2-methylpiperazine) | 95 |
| 124 | 6-Chloro | (2-methylpiperazine) | >98 |
| 125 | 7-COOMe | (2-ethylpiperazine) | >98 |

TABLE 2-continued
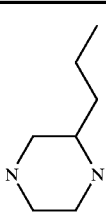
| Example # | R₁ | W | % Inhibition @ 10 uM |
|---|---|---|---|
| 126 | 7-COOMe | 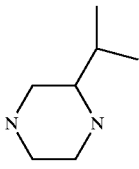 | >98 |
| 127 | 7-COOMe | 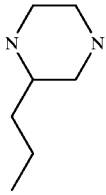 | 95 |
| 128 | 7-COOMe | 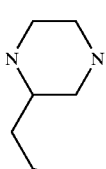 | 95 |
| 129 | 7-COOMe | 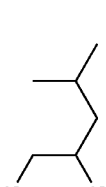 | 81 |
| 130 | 7-COOMe | 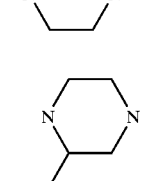 | 77 |
| 131 | 7-COOMe | 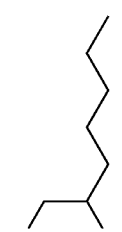 | 63 |
| 132 | 7-COOMe | 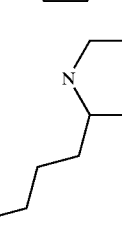 | 59 |
| 133 | 7-COOMe | 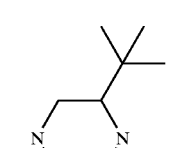 | 92 |
| 134 | 7-COOMe | 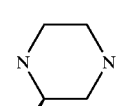 | 87 |
| 135 | 4-OMe | 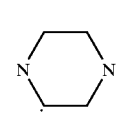 | >98 |
| 136 | 4-OMe | 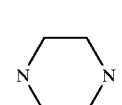 | >98 |
| 137 | 7-COOH | 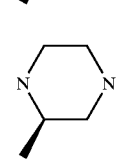 | >98 |
| 138 | 4-Fluoro-7-methyl | | >98 |

TABLE 2-continued

| Example # | R₁ | W | % Inhibition @ 10 uM |
|---|---|---|---|
| 139 | 7-COOMe | piperazine with CH₂ substituent | >98 |
| 140 | 7-Fluoro | methyl-piperazine | >98 |
| 141 | 7-Fluoro | methyl-piperazine | 96 |
| 142 | 7-COOMe | F₃C-piperazine | >98 |
| 143 | 4-Fluoro | F₃C-piperazine | 91 |
| 144 | 4-fluoro-7-bromo | methyl-piperazine | >98 |
| 145 | 4-Fluoro-7-COOMe | methyl-piperazine | >98 |
| 146 | 4-Fluoro-7-COOH | methyl-piperazine | >98 |
| 147 | 4-Fluoro-7-OMe | methyl-piperazine | >98 |

TABLE 3

| Entry | R | Ar | % Inhibition at 10 μM |
|---|---|---|---|
| 148 | 4-Fluoro | 3-Thiophenyl | >98 |
| 149 | 4-Fluoro | 1,2,3-Thiadiazolyl | 88 |
| 150 | 4-Fluoro | 2-(4-Methoxy)-thiophenyl | 81 |
| 151 | 4-Fluoro | 2-(5-Methylthio)-thiophenyl | 75 |
| 152 | 4-Fluoro | 2-(3-Bromo)-thiophenyl | 97 |
| 153 | 4-Fluoro | 2-(5-Bromo)-thiophenyl | >98 |
| 154 | 4-Fluoro | 2-Pyrazinyl | 80 |
| 155 | 4-Fluoro | 2-(5-Methyl)-thiophenyl | >98 |
| 156 | 4-Fluoro | 2-(5-Chloro)-thiophenyl | >98 |
| 157 | 4-Fluoro | 2-Indolyl | 70 |
| 158 | 4-Fluoro | 4-(2-Methyl)-thiazolyl | 92 |
| 159 | 4-Fluoro | 4-Thiazolyl | >98 |
| 160 | 4-Fluoro | 4-Pyridyl | 98 |
| 161 | 4-Fluoro | 3-(6-Methyl)-pyridyl | 94 |
| 162 | 4-Fluoro | 3-Pyridyl | 97 |
| 163 | 4-Fluoro | 5-Isoxazolyl | 90 |
| 164 | 4-Fluoro | 2-Furanyl | >98 |
| 165 | 4-Fluoro | 3-Pyrazolyl | 92 |
| 166 | 4-Fluoro | 2-Pyridyl | >98 |
| 167 | 4-Fluoro | 3-Furanyl | >98 |
| 168 | 4-Fluoro | 2-Thiophenyl | >98 |
| 169 | 4-Fluoro | 2-Benzofuranyl | 80 |
| 170 | 4-Fluoro | 2-(5-Bromo)-furanyl | >98 |
| 171 | 4-Fluoro | 2-(3-Methyl)-furanyl | >98 |
| 172 | 4-Fluoro | 2-(3-Chloro)-thiophenyl | >98 |
| 173 | 4-Fluoro | 3-(5-Chloro-4-methoxy)-thiophenyl | >98 |
| 174 | 4-Fluoro | 2-(5-Chloro)-furanyl | >98 |
| 175 | 4-Chloro | 3-Thiophenyl | >98 |
| 176 | 4-Chloro | 2-[5-(Pyrid-2-yl)]-thiophenyl | 86 |
| 177 | 4-Chloro | 2-Thieno[3,2-B]-thiophenyl | >98 |
| 178 | 4-Chloro | 2-(5-Methylthio)-thiophenyl | 93 |
| 179 | 4-Chloro | 2-(5-Bromo)-thiophenyl | >98 |
| 180 | 4-Chloro | 2-Pyrazinyl | 76 |
| 181 | 4-Chloro | 2-Pyridyl | 96 |
| 182 | 4-Chloro | 2-Benzothiophenyl | 89 |
| 183 | 4-Chloro | 2-(5-Chloro)-thiophenyl | >98 |
| 184 | 4-Chloro | 2-(3-Chloro)-thiophenyl | 94 |
| 185 | 4-Chloro | 2-Indolyl | 85 |
| 186 | 4-Chloro | 4-(2-Methyl)-thiazolyl | 91 |
| 187 | 4-Chloro | 4-Thiazolyl | 98 |
| 188 | 4,7-Difluoro | 2-(5-Chloro)- | >98 |

TABLE 3-continued

*(Structure: R-substituted indole-3-yl with glyoxyl-piperazine-carbonyl-Ar)*

| Entry | R | Ar | % Inhibition at 10 μM |
|---|---|---|---|
| 189 | 4,7-Difluoro | 2-(5-Bromo)-furanyl | >98 |
| 190 | 4,7-Difluoro | 2-furanyl | >98 |
| 191 | 4,7-Difluoro | 2-Pyridyl | 95 |
| 192 | 4,7-Difluoro | 2-(3,4-Dichloro)-furanyl | >98 |
| 193 | 4,7-Difluoro | 2-(5-Trifluoromethyl)-furanyl | >98 |
| 194 | 4,7-Difluoro | 2-(4,5-Dimethyl)-furanyl | >98 |
| 195 | 4-Fluoro | 2-Imidazolyl | 71 |

TABLE 4

*(Structure: R-substituted indole-3-yl with glyoxyl-(methyl-piperazine)-carbonyl-Ar)*

| Entry | R | Ar | % Inhibition @ 10 μM |
|---|---|---|---|
| 196 | 4,7-difluoro | 2-Pyridyl | >98 |
| 197 | 4-Fluoro-7-methyl | 2-Pyridyl | 93 |
| 198 | 4,7-Difluoro | 2-(5-Bromo)-furanyl | >98 |
| 199 | 4,7-Dimethoxy | 2-(5-Bromo)-furanyl | >98 |
| 200 | 7-COOMe | 2-(5-Bromo)-furanyl | >98 |
| 201 | 4,7-Difluoro | 2-Pyridyl | >98 |
| 202 | 4-Fluoro | 2-Pyridyl | >98 |
| 203 | 4-Chloro | 2-Pyridyl | 80 |
| 204 | 4-Bromo | 2-Pyridyl | 50 |
| 205 | 5-Fluoro | 2-Pyridyl | 61 |
| 206 | 6-Chloro | 2-Pyridyl | 88 |
| 207 | 7-Fluoro | 2-Pyridyl | >98 |
| 208 | 7-Methoxy | 2-Pyridyl | >98 |
| 209 | 7-Methyl | 2-Pyridyl | >98 |
| 210 | 7-Ethyl | 2-Pyridyl | 88 |
| 211 | 4-methoxy-7-chloro | 2-Pyridyl | >98 |
| 212 | 7-cyano | 2-Pyridyl | >98 |
| 213 | 4-Methoxy | 2-Pyridyl | >98 |
| 214 | 4-Methoxy-7-Bromo | 2-Pyridyl | >98 |

TABLE 4-continued

| Entry | R | Ar | % Inhibition @ 10 μM |
|---|---|---|---|
| 215 | 4-Fluoro-7-Methoxy | 2-Pyridyl | >98 |

EXPERIMENTAL PROCEDURES

Biology

Abbreviations

"μM" means micromolar;

"μci" means microcurie;

"ml" means milliliter;

"μl" means microliter;

"μg" means microgram;

"M" means molar;

"μm" means micromolar;

"mM" means millimolar;

"a" refers to percent inhibition data as representing the mean values of at least two experiments with duplicate determinations in each experiment.

"RT" refers to reverse transcriptase.

The materials and experimental procedures used to obtain the anti-viral results for Examples 1–34 are described below.

Cells—MT-2 T cell lines propagated in Roswell Park Memorial Institute (RPMI) 1640 medium (Life Technologies, Gaithersburg, Md.) containing 10% fetal Bovine serum (FBS, Sigma, St. Louis, Mo.).

Virus—The laboratory HIV-1 strain BRU was titrated using an infectivity assay (johnson, V. A. and R. E. Byrington, 1990).

Experiment

1. MT-2 cells (Harada, et al, Ref. 30) were infected by HIV-1 BRU at a multiplicity of infection (MOI) of 0.005 in RPMI 1640 medium containing 10% fetal Bovine serum at a concentration of $1 \times 10^5$ cells/ml.

2. Compound was added to 100 μl RPMI 1640 media containing 10% fetal Bovine serum per well in a 96 well plate at a concentration of 20 μM.

3. 100 μl of $1 \times 10^5$/ml infected MT-2 cells were added to each well in such plates, resulting in a final cell concentration of $5 \times 10^4$ cells/ml and a final compound concentration of 10 μM.

4. Samples were incubated at 37° C. and harvested 6 days after infection.

5. HIV-1 replication was quantified by measuring the HIV-1 reverse transcriptase (RT) activity present in cell-free supernatants (Potts, et al, Ref. 27). For each sample, 20 μl of cell-free supernatant was added to 40 μl RT cocktail [42 μM Tris(hydroxymethyl) aminomethane pH 7.8 (Sigma, St. Louis, Mo.), 63 μM potassium chloride (Mallinckrodt, Paris Ky.), 2 μM dithiothreitol (Sigma, St. Louis, Mo.), 4

μM magnesium chloride (Mallinckrodt, Paris Ky.), 4 μg/ml polyadenylic acid (Pharmacia, Piscataway, N.J.), 1.3 μg/ml oligonucleotide deoxythymidinel 2–18 (Pharmacia, Piscataway, N.J.), 0.04% (octylphenoxy)-polyethoxyethanol (Nonidet P40, Sigma, St. Louis, Mo.), and 17 μCi/ml 3H-deoxythymidine 5'-triphosphate (NEN, Boston, Mass.)]. Assays were incubated for 1 hour at 37° C. and then 1 μl portions of each reaction were spotted on diethylaminoethyl cellulose (DE-81) filter paper (Whatman, Hillsboro, Oreg.), allowed to dry, washed four times with 0.3 M sodium chloride (Fisher Scientific, Pittsburgh, Pa.), 30 mM sodium citrate pH 7.0 (Sigma, St. Louis, Mo.), followed by two washes in 95% ethanol. Bound radioactivity was quantified by scintillation counting.

6. The percent inhibition for each compound was calculated by quantifying the level of HIV-1 replication in the presence of each compound as a percentage of the no compound control and subtracting such a determined value from 100.

7. To determine the cytotoxicity of compounds, uninfected cells were incubated with a series of concentrations of each compound for 3–6 days. Cell viability was determined by the XTT {2,3-bis(2-methoxy-4-nitro-5-sulfophenyl)-5-[(phenylamino)carbonyl]-2H-tetrazolium hydroxide} dye reduction method (Weislow et al, Ref. 28). The percentage of living cells in compound containing wells compared to untreated controls was determined. The 50% cytotoxic concentration was calculated as the concentration of drug that decreased the percentage of living cells to 50% of those in untreated cells.

The materials and methods for determination of anti-viral activity for examples 35–215 are described below:

Cells:
  Virus production—Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).
  Virus infection—Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis, Mo.) and supplemented with 0.2 mg/ml Geneticin (Life Technologies, Gaithersburg, Md.) and 0.4 mg/ml Zeocin (Invitrogen, Carlsbad, Calif.).
  Virus-Replication defective reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen, 1994). Transfections were performed using lipofectAMINE PLUS reagent as described by the manufacturer (Life Technologies, Gaithersburg, Md.).

Experiment
1. Compound was added to HeLa CD4 $CCR_5$ cells plated in 96 well plates at a cell density of $5\times10^4$ cells per well in 100 ul Dulbecco's Modified Eagle Medium containing 10% fetal Bovine serum at a concentration of <20 uM.
2. 100 ul of replication defective reporter virus in Dulbecco's Modified Eagle Medium was then added to the plated cells and compound at a multiplicity of infection (MOI) of 0.01, resulting in a final volume of 200 ul per well and a final compound concentration of <10 uM.
3. Samples were harvested 72 hours after infection.
4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 ul of Dulbecco's Modified Eagle Medium (without phenol red) and 50 ul of luciferase assay reagent reconstituted as described by the manufacturer (Roche Molecular Biochemicals, Indianapolis, Ind.) was added per well. Luciferase activity was then quantified by measuring luminescence using a Wallac microbeta scintillation counter.
5. The percent inhibition for each compound was calculated by quantifying the level of luciferase expression in cells infected in the presence of each compound as a percentage of that observed for cells infected in the absence of compound and subtracting such a determined value from 100.

References
Chen, B. K., Saksela, K., Andino, R., and D. Baltimore. 1994. Distinct modes of human immunodeficiency type 1 proviral latency revealed by superinfection of nonproductively infected celllines with recombinant luciferase-encoding viruses. J. Virol. 68:654–660 (Ref. 37).

Chemistry
  General: Unless otherwise noted, solvents and reagents were used directly as obtained from commercial sources, and reactions were performed under the nitrogen atmosphere. Flash chromatography was conducted on Silica gel 60 (0.040–0.063 particle size; EM Science supply). $^1$H NMR spectra were recorded at 500 MHz, unless otherwise noted, and the chemical shifts are reported relative to residual solvent signals. The following standard acronyms were employed to describe the multiplicity patterns: s (singlet), d (doublet), t (triplet), q (quartet), m (multiplet), b (broad), app (apparent). The coupling constant (J) is in hertz.

All Liquid Chromatography (LC) data were recorded on a Shimadzu LC-10AS liquid chromotograph using a SPD-10AV UV-Vis detector and Mass Spectrometry (MS) data were determined with a Micromass Platform for LC in electrospray mode.

LC/MS Method (i.e., Compound Identification)
  Unless otherwise noted, all compounds were analyzed using the following conditions:
  Column: YMC ODS S7 3.0×50 mm column
  Gradient: 100% Solvent A/0% Solvent B to 0% Solvent A/100% Solvent B
  Gradient time: 2 minutes
  Hold time: 1 minute
  Flow rate: 5 mL/min
  Detector Wavelength: 220 nm
  Solvent A: 10% MeOH/90% $H_2O$/0.1% Trifluoroacetic Acid
  Solvent B: 10% $H_2O$/90% MEOH/0.1% Trifluoroacetic Acid When noted, the following conditions were used for HPLC analysis:
  Method A: Column YMC ODS-A C18 S7 3.0×50 min Start%B=0/Finish%B=100
  Method B: Column YMC ODS-A C18 S7 3.0×50 min Start%B=30/Finish%B=100
  Method C: Column PHX-LUNA C18 4.6×30 mm Start%B=0/Finish%B=100

Compounds purified by preparative HPLC were diluted in methanol (1.2 mL) and purified using the following methods on a Shimadzu LC-10A automated preparative HPLC system.

Preparative HPLC Method (i.e., Compound Purification)

Purification Method: Initial gradient (40% B, 60% A) ramp to final gradient (100% B, 0% A) over 20 minutes, hold for 3 minutes (100% B, 0% A)

Solvent A: 10% MeOH/90% $H_2O$/0.1% Trifluoroacetic Acid

Solvent B: 10% $H_2O$/90% MeOH/0.1% Trifluoroacetic Acid

Column: YMC C18 S5 20×100 mm column

Detector Wavelength: 220 nm

Indoles were either commercially available, or were prepared using known chemistry such as the method of Bartoli (Ref. 36) or as described by Gribble (Ref. 24)

Representative indole syntheses are shown below.

Preparation of 4-Fluoro-7-methyl Indole

Step A

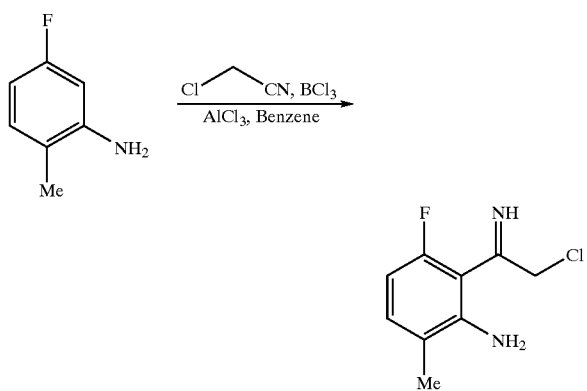

A flame dried 50 ml three neck flask was charged with BCl3 (44 mmol, 44 ml, 1 M in benzene) and 10 mL dry benzene at rt. under N2. The mixture was cooled down to 0° C. followed by dropwise addition of 5-fluoro-2-methylaniline(5 g, 40 mmol) in 10 ml dry benzene over 10 min, chloroacetonitrile (2.18 g, 48 mmol) over 2 min and AlCl3 in one portion. After stirring at 0° C. for 5 min, the ice-bath was removed and the mixture was refluxed for 6 hr under N2. The resulted mixture was cooled down to rt. and poured into EtOAc/1N HCl (300 mL, 50:50 v:v with ice). After separation, the aqueous phase was extracted with EtOAc (2×100 mL). The combined organic layers were washed with water (100 mL), brine (2×100 mL), and dried with MgSO4. The solvent was removed in vacuo, and the crude intermediate was used directly in next step without further purification.

Step B

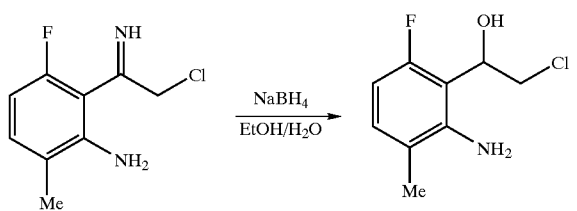

The above residue was dissolved in 100 mL ETOH. Then the mixture was cooled down to 0° C., followed by dropwise addition of NaBH4 in 2 ml H2O. After stirring at 0° C. for 1 hr, the reaction was quenched with H2O (10 ml). The solvent was removed in vacuo and the residue was dissolved in EtOAc (150 ml), and washed with brine (2×50 ml). The organic layer was dried with MgSO4, the solvent was removed, and the expected reduced intermediate was used directly in next cyclization step.

Step C:

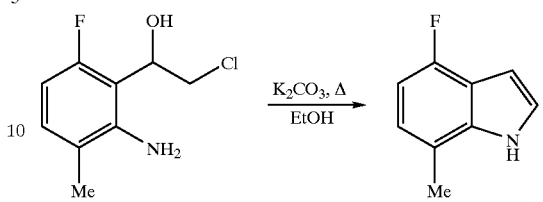

The above intermediate, a yellow oil, was dissolved in 100 ml EtOH, followed by addition of K2CO3 (11.0 g, 80 mmol). The mixture was refluxed under N2 for 2 hr, and cooled down to rt. The solids were removed by filtering through celite, and the resulted solution was concentrated in vacuo. The residue was dissolved in EtOAc (200 mL), washed with brine (2×50 ml) and dried over MgSO4. The solvent was removed in vacuo and gave a brown oil which was purified by flash chromotography (12% EtOAc in hexanes), to yield 2.3 g (39% overall yield) of pure product. M+H, 150.0; Retention time, 1.297 min.

Synthesis of 4-Ethoxyindole

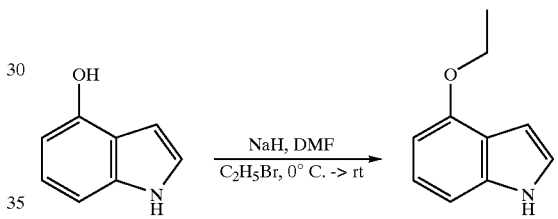

An oven dried two neck flask was charged with 5 ml DMF and NaH (66 mg, 60% in oil, 1.65 mmol). The mixture was cooled down to 0° C., followed by dropwise addition of 4-hydroxy indole (200 mg, 1.5 mmol) in 5 ml DMF over 10 second. After stirring for 30 min under N2, bromoethane in 2 ml DMF was added dropwise, and the reaction was allowed to warm to rt. with continued stirring for 2 hr. Removal of the solvent in vacuo, followed by aqueous work up afforded crude 4-ethoxyindole which was purified by prep. HPLC to afford 201 mg (83%) of pure 4-ethxyindole; HPLC retention time, 1.190 min.

Synthesis of 4-Fluoro-7-carbomethoxy Indole

Step A:

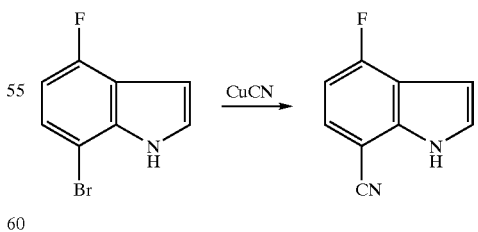

A mixture of 4-fluoro-7-bromoindole (600 mg, 2.8 mmol) and CuCN (1.004 g, 11.2 mmol) in DMF (4 ml) was refluxed for 16 hours. After cooling to room temperature, the reaction mixture was poured into a solution of ammonia in MeOH (30 ml, sat.) and the residue removed by filtration. The filtrate was added to a mixture of water (20 ml)/ammonia (20 ml, sat. aq.) and extracted with EtOAc/Ether (1/1) until TLC analysis showed no product in the aqueous phase. The combined organic extracts were washed with brine (2×200 ml) and water (200 ml), dried (MgSO₄); evaporation in zacuo gave 4-fluoro-7-cyanoindole as a tan yellow solid (310 mg, 69%).
Step B

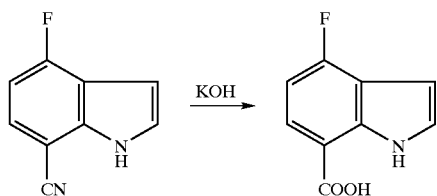

To a solution of KOH (13.04 g, 0.232 mol) in 14% H₂O/EtOH (50 ml) was added 4-fluoro-7-cyanoindole (900 mg, 5.60 mmol). The resulting mixture was refluxed for 12 hours, slowly cooled to room temperature, and concentrated in vacuo to about 30 ml. The residue was acidified to pH 2 with HCl (~5.5 N aq.). The precipitate was filtered, washed with excess of water, and dried under high vacuum to afford 4-fluoro-7-carboxyindole as a white solid (100% conversion). The material was used without further purification.
Step C

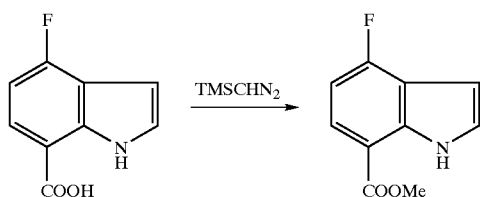

To a suspension of 4-fluoro-7-carboxyindole in a mixture of MeOH (18 ml)/PhH (62 ml) was added (trimethylsilyl) diazomethane (8.8 ml, 17.6 mmol, 2 M in hexane). The resulting mixture was stirred at room temperature for 30 min., quenched with excess acetic acid and evaporated in vacuo. The crude oily material was purified by flash chromatography using a gradient elution (Hexane to 10% EtOAc/Hexane) to afford methyl (4-fluoro)indole-7-carboxylate as a white solid (1.04 g, 83% two steps)

Preparation of 4-Fluoroindole-7-carboxaldehyde

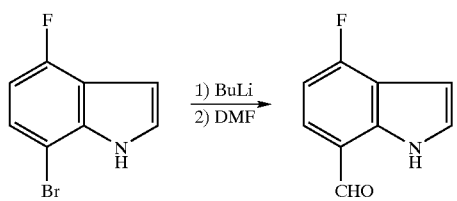

To a solution of 4-fluoro-7-bromoindole (1.0 g, 4.7 mmol) in THF (5 mL) at −78° C. was added n-BuLi (5.6 mL, 2.5M in hexanes) dropwise. The mixture was stirred for 15 min at −78° C., was allowed to warm to 5° C. for 30 min and was then re-cooled to −78° C. DMF (1.8 mL) was then added and the mixture was allowed to warm to room temperature slowly. The reaction was quenched with water and was extracted with ether. The organic phase was dried over MgSO4, filtered and concentrated to afford 4-fluoroindole-7-carboxaldehyde.

General Procedure for Preparation of Examples 1–17 in Table 5
Step A

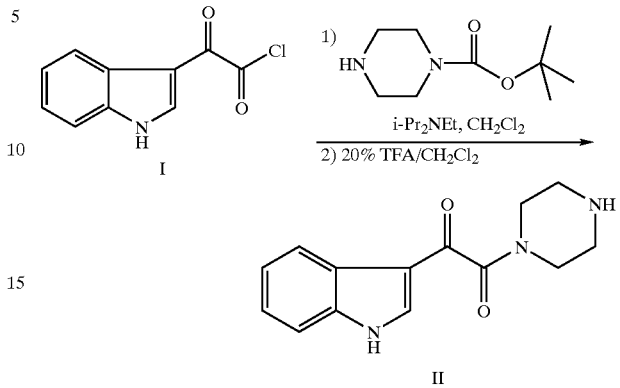

To commercially available indole-3-glyoxylyl chloride I (3 gram, 14.45 mmol) in CH₂Cl₂ at room temperature was added tert-butyl 1-piperazinecarboxylate (2.7 gram, 14.45 mmol) and diisopropylethylamine (2.76 ml, 15.9 mmol). The light-brown color solution was stirred for 2 hr at room temperature after which time LC/MS analysis indicated the completion of the reaction. The solvent was removed in vacuo and the resulting residue was diluted with ethyl acetate (250 ml) and diethylether (250 ml). The organic solution was then washed with water (100 ml×3) and brine (50 ml), dried over MgSO₄, filtered and concentrated. To the light-yellow solid was then added 30 ml of 20% trifluoroacetic acid in CH₂Cl₂. The solution was concentrated and the light-brown solid was dried in vacuo to give 3.5 g (95%) of product II. LC/MS analysis indicated this product was 100% pure and it was used for the next reaction without further purification.
Step B

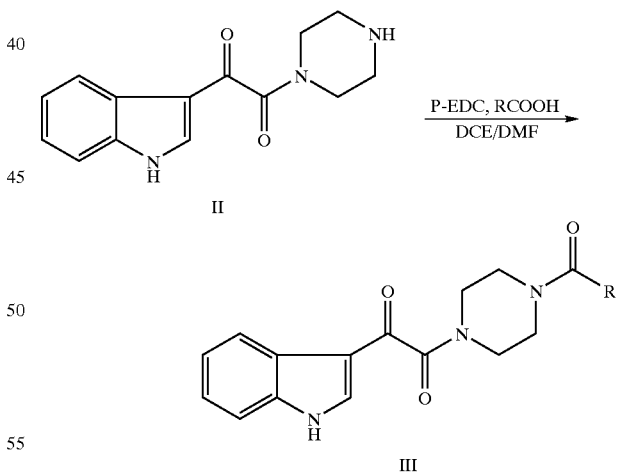

To piperazine indole-3-glyoxylamide II (0.03 mmol) was added resin-bound 1-(3-dimethylaminopropyl)-3-ethylcarbodiimide (P-EDC) (0.21 mmol) and carboxylic acid (RCOOH) (0.06 mmol) in dichloroethane (DCE) (1 mL) or DMF (dimethylformamide) (1 mL) in cases where the carboxylic acids are not soluble in DCE. The reaction was shaken for 12 hr at room temperature. The product III was filtered and concentrated. Products with purity less than 70% were diluted in methanol and purified using a Shimadzu automated preparative HPLC System.

2) General Procedure for Preparation of Examples 18–56 in Table 5

Step A.

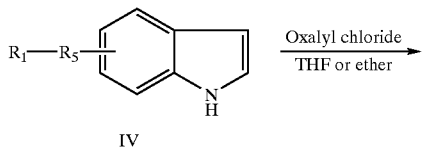

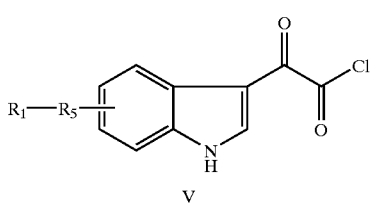

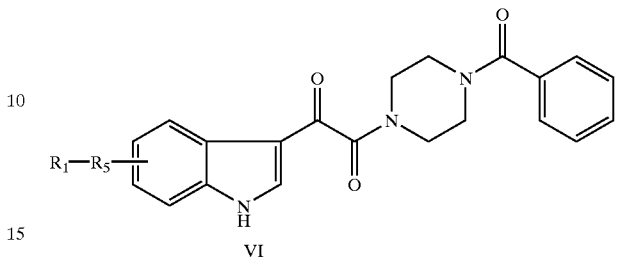

To a solution of indole glyoxyl chloride V (1 eq) in dry THF was added benzoylpiperazine (1 eq) at room temperature. Then the mixture was cooled down to 0° C., followed by dropwise addition of diisopropylamine (1.3 eq). After 5 min., the reaction mixture was warmed to room temperature and was shaken for 3 hr. The resulting crude products VI were purified by preparative HPLC and characterized as shown in Table 5.

To a solution of substituted indole IV (1 eq) in dry Et$_2$O was dropwise added oxalylchloride (1.2 eq) at 0° C. After 5 min., the reaction mixture was warmed to room temperature, or heated to 35° C. overnight if necessary. The intermediate substituted-indole-3-glyoxylyl chloride V, 10 which was formed as a solid, was filtered and washed with dry ether (2×1 ml) to remove excessive oxalyl chloride. The product was then dried under vacuum to give desired glyoxyl chlorides V.

In cases where reaction in Et$_2$O was unsuccessful, the following procedure was adopted: To a solution of substituted indole IV (1 eq) in dry THF (tetrahydrofuran) solvent was dropwise added oxalyl chloride (1.2 eq) at 0° C. After 5 min., the reaction was warmed to room temperature, or heated to ~70° C. under nitrogen if necessary. After concentration in vacuo, the resulting crude intermediate V was submitted to next step without further treatment.

General Procedure for Preparation of Examples 58–63 in Table 5

Step A

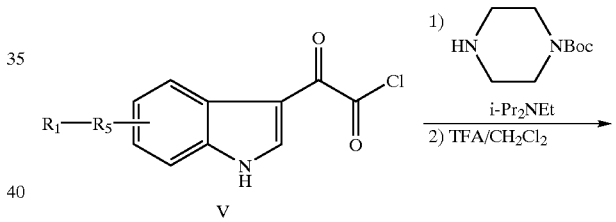

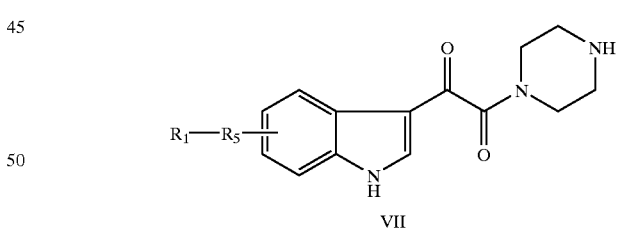

Step B

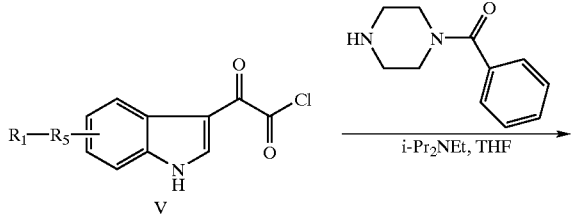

To glyoxyl chloride V (1 equiv.) in CH$_2$Cl$_2$ at room temperature was added tert-butyl 1-piperazinecarboxylate (1 equiv) and diisopropylethylamine (1.2 equiv). The solution was stirred for 2 hr at room temperature after which time LC/MS analysis indicated the completion of the reaction. The solvent was removed in vacuo and the resulting residue was diluted with ethyl acetate and diethylether. The organic solution was then washed with water (100 ml×3) and brine (50 ml), dried over MgSO$_4$, filtered and concentrated. To the solid was then added 30 ml of 20% trifluoroacetic acid in CH$_2$Cl$_2$. The solution was concentrated and the light-brown solid was dried in vacuo to give glyoxamide VII.

Step B

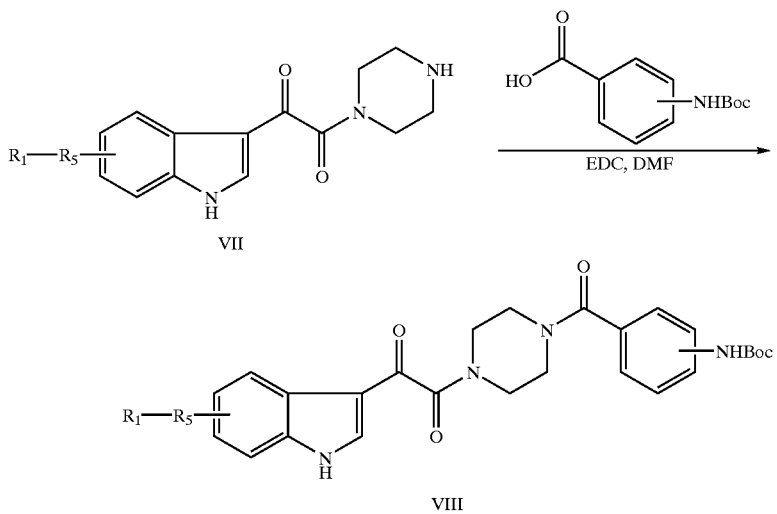

To piperazine glyoxamide VII (0.1 mmol, 1 eq) in DMF (1 mL) at room temperature was added EDC (1.5 eq) and Boc-aminobenzoic acid (1.5 eq). The reaction mixture was stirred at room temperature for 16 hours. The crude product was then purified by preparative HPLC to afford product VIII.

General Procedure for Preparation of Examples 65–73 in Table 5

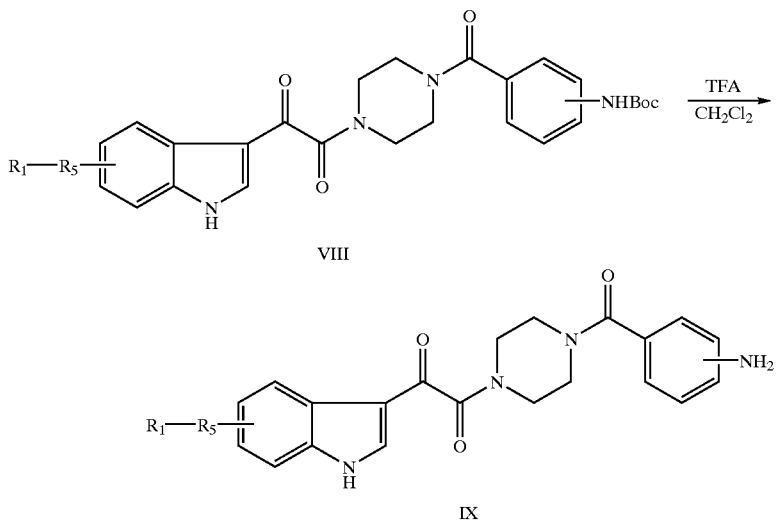

To Boc-protected derivative VIII (0.03 mmol) was added 50% TFA/CH$_2$Cl$_2$ (1.5 mL). The reaction mixture was stirred at room temperature for 16 hours. The product was then concentrated in vacuo to afford product IX as its TFA salt. The purity of IX was sufficient that no further purification was necessary.

General Procedure for Preparation of Examples 82–86 in Table 5

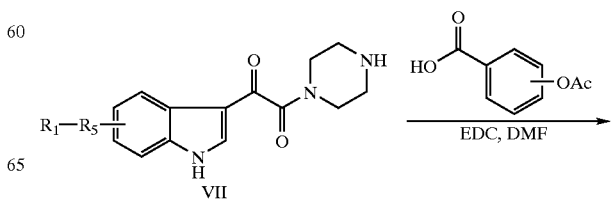

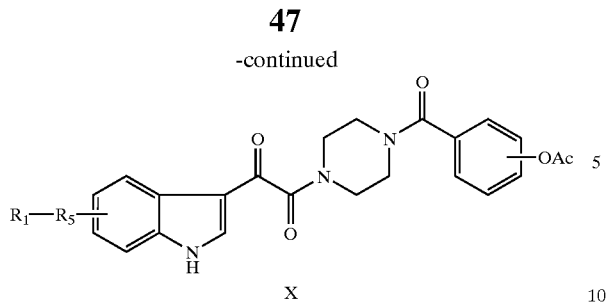

X

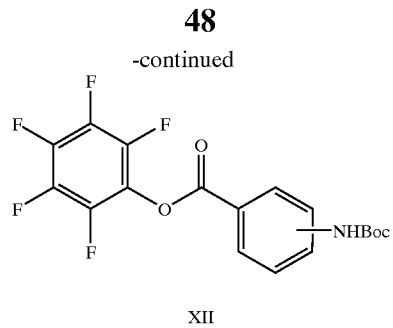

XII

To piperazine glyoxamide VII (0.1 mmol, 1 eq) in DMF (1 mL) at room temperature was added EDC (1.5 eq) and acetoxybenzoic acid (1.5 eq). The reaction mixture was stirred at room temperature for 16 hours. The crude product was then purified by preparative HPLC to afford product X.

General Procedure for Preparation of Examples 87–89 in Table 5

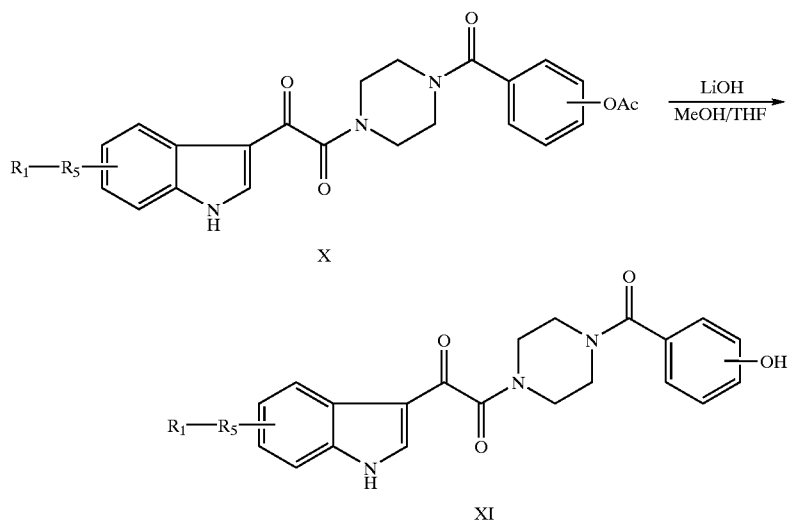

To acetate-protected derivative X (0.03 mmol, 1 eq) was added aqueous LiOH (3 eq) in THF/MeOH (1.5 mL, 1:1). The reaction mixture was stirred at room temperature for 16 hours. The crude product was then purified by preparative HPLC to afford product XI.

General Procedure for Preparation of Examples 64 and 74–81 in Table 5

Step A

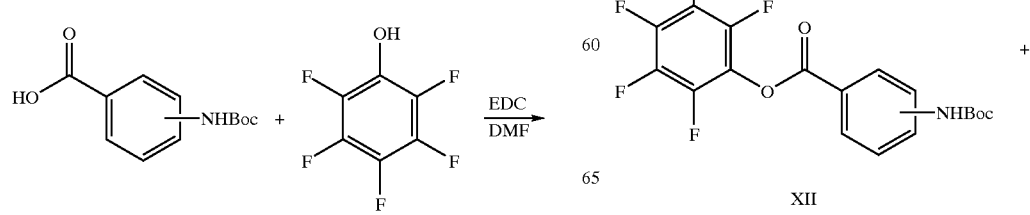

XII

To a solution of Boc-protected amino benzoic acid (5 mmol) in DMF (10 mL) at room temperature was added pentafluorophenol (5 mmol) followed by EDC (5 mmol). The reaction mixture was stirred at room temperature for 3 h. The crude product was diluted with CH2Cl2 and was washed with water, 0.1 M HCl and brine. The organic phase was dried over MgSO4, filetered and concentrated. The pentafluorophenyl ester XII was used in the following reaction without further purification.

Step B

-continued

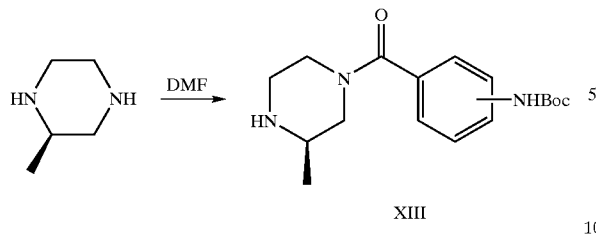

XIII

To a stirred solution (R)-2-methylpiperazine in DMF (15 mL) at room temperature was added a solution of pentafluorophenyl ester XII in DMF (2 mL) dropwise. The reaction mixture was stirred at room temperature for 16 hours. The crude product was diluted with CH2Cl2 and was washed with Na2CO3 (sat) and brine. The organic phase was dried over MgSO4, filtered and concentrated. The crude product was purified by flash chromatography (50% EtOAc/Hexane—10% MeOH/EtOAc) to afford product XIII.

Step C

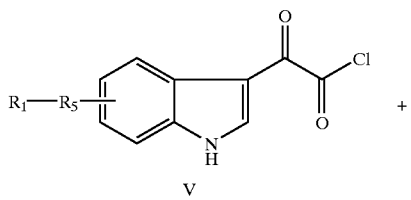

V

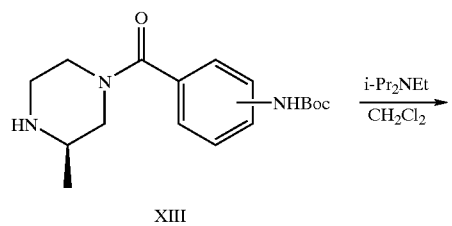

XIII

-continued

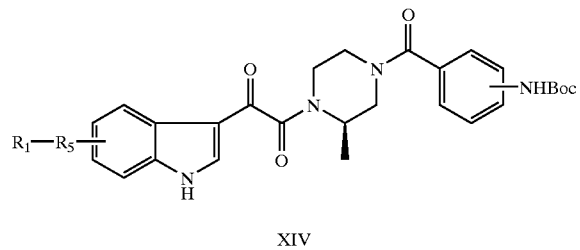

XIV

To indole-3-glyoxyl chloride V (1 eq.) in CH2Cl2 was added acylpiperazine XII followed by i-Pr$_2$NEt (3 eq.). The reaction mixture was stirred at room temperature for 5 hours, was then diluted with methanol and product XIV was purified by preparative HPLC.

Step D

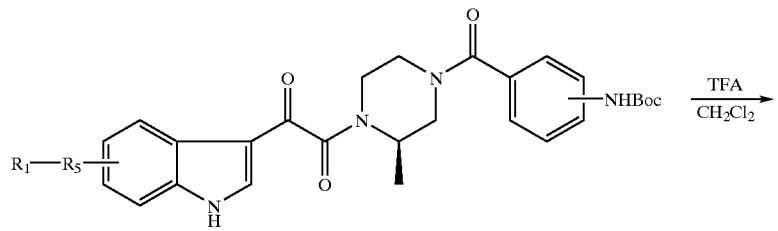

XIV

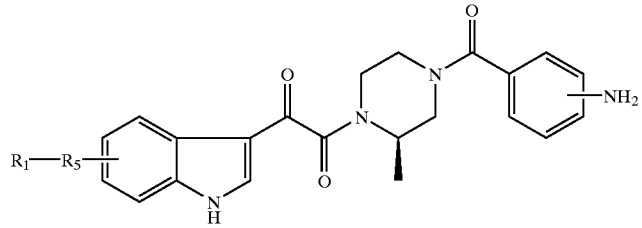

XV

To Boc-protected derivative XIV (~0.03 mmol) was added 50% TFA/CH$_2$Cl$_2$ (1.5 mL). The reaction mixture was stirred at room temperature for 16 hours. The product was then concentrated in vacuo to afford product XV. The purity of XV was sufficient that no further purification was necessary.

Procedure for the Synthesis of Examples 57 and 90 in Table 5.

Step A

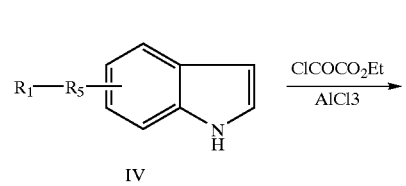

IV

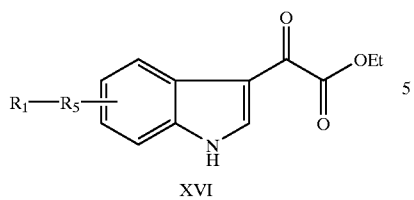

XVI

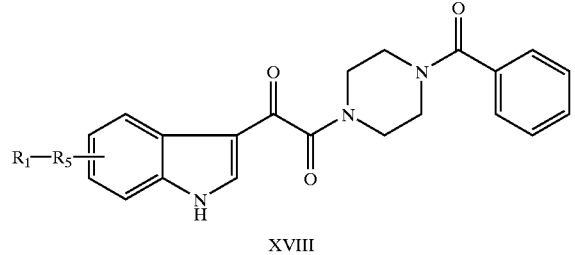

XVIII

To substituted indole IV (1 equiv) in CH₂Cl₂ at 0° C. was added ethyl chloroxalate (2 equiv) dropwise followed by addition of AlCl₃ (2 equiv). The reaction was stirred at 0° C. and was then allowed to warm to room temperature overnight. The reaction was quenched by dropwise addition of HCl (1N). The crude material was extracted with EtOAc and was washed with water, dried over MgSO4, filtered and concentrated. The crude product was then recrystallised from EtOAc/Hexanes to afford ester XVI.

To acid XVII (1 equiv) in DMF was added benzoyl pierazine (1.2 equiv) followed by DEPBT (1.2 equiv) and i-Pr2NEt (2 equiv). The reaction mixture was stirred at room temperature for 2 h. It was then diluted with EtOAc, was washed with water and brine, dried over MgSO4, filtered and concentrated. The crude product was then purified by flash chromatography (EtOAc/MeOH, 95:5) to afford the desired product XVIII.

Step B

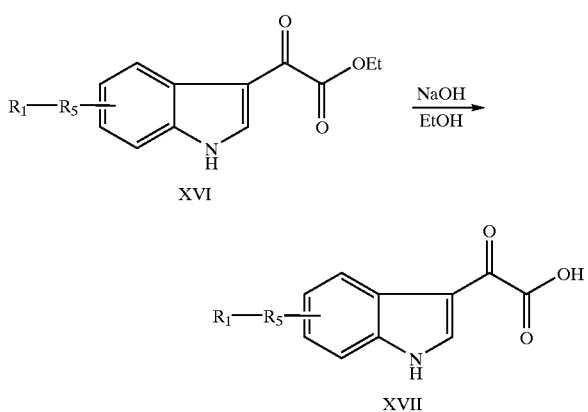

To ester XVI (1 equiv) in EtOH was added NaOH (2.5 equiv, 10N) dropwise. The reaction mixture was stirred at rt for 30 min and was then heated to 45° C. for an additional 90 min. The product was concentrated in vacuo. The resulting residue was partitioned between EtOAc and water. The organic layer was separated and was washed with water, dried over MgSO4, filtered and concentrated to afford acid XVII.

Step C

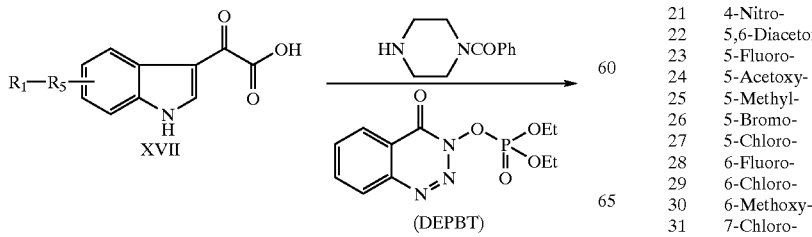

TABLE 5

| Example # | R₁ | R₂ | R₃ | HPLC Retention Time (min) | MS Data (M + H)⁺ |
|---|---|---|---|---|---|
| 1 | H | H | H | 1.13 | 362 |
| 2 | H | H | 2,6-Difluoro- | 1.36 | 398 |
| 3 | H | H | 2,4-Difluoro | 1.43 | 398 |
| 4 | H | H | 2-Fluoro-3-chloro- | 1.54 | 415 |
| 5 | H | H | 2-Fluoro- | 1.42 | 380 |
| 6 | H | H | 2-Acetoxy- | 1.63 | 378 |
| 7 | H | H | 2-Hydroxy- | 1.25 | 378 |
| 8 | H | H | 3-Chloro-4-fluoro- | 1.56 | 415 |
| 9 | H | H | 3-Fluoro-4-methyl- | 1.54 | 394 |
| 10 | H | H | 3,4-Difluoro | 1.45 | 398 |
| 11 | H | H | 3-Fluoro- | 1.44 | 380 |
| 12 | H | H | 3-Bromo- | 1.56 | 442 |
| 13 | H | H | 4-Hydroxy- | 1.17 | 378 |
| 14 | H | H | 4-Fluoro- | 1.43 | 380 |
| 15 | H | H | 4-Methyl- | 1.34 | 376 |
| 16 | H | H | 4-tertButyl- | 1.76 | 419 |
| 17 | H | H | 4-Acetoxy- | 1.58 | 420 |
| 18 | 2-Methyl- | H | H | 1.86 | 376 |
| 19 | 4-Fluoro- | H | H | 1.21 | 380 |
| 20 | 4-Chloro- | H | H | 1.35 | 397 |
| 21 | 4-Nitro- | H | H | 1.16 | 407 |
| 22 | 5,6-Diacetoxy- | H | H | 1.78 | 478 |
| 23 | 5-Fluoro- | H | H | 1.69 | 380 |
| 24 | 5-Acetoxy- | H | H | 1.76 | 420 |
| 25 | 5-Methyl- | H | H | 1.37 | 376 |
| 26 | 5-Bromo- | H | H | 1.51 | 442 |
| 27 | 5-Chloro- | H | H | 1.58 | 396 |
| 28 | 6-Fluoro- | H | H | 1.80 | 380 |
| 29 | 6-Chloro- | H | H | 2.01 | 396 |
| 30 | 6-Methoxy- | H | H | 1.28 | 392 |
| 31 | 7-Chloro- | H | H | 1.50 | 397 |

TABLE 5-continued

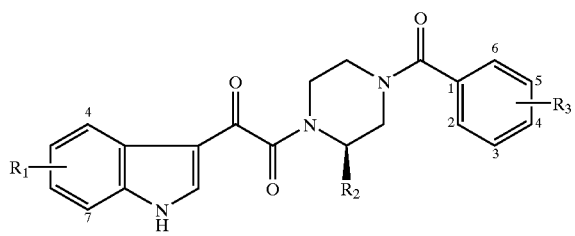

| Example # | R₁ | R₂ | R₃ | HPLC Retention Time (min) | MS Data (M + H)⁺ |
|---|---|---|---|---|---|
| 32 | 7-Carboethoxy- | H | H | 1.41 | 380 |
| 33 | 7-Ethyl- | H | H | 1.57 | 390 |
| 34 | 7-Methyl- | H | H | 1.47 | 376 |
| 35 | 7-Bromo | H | H | 1.54 | 442 |
| 36 | 7-Methoxy | H | H | 1.37 | 392 |
| 37 | 6-Trifluoromethyl | H | H | ND | 430 |
| 38 | 7-Fluoro | H | H | 1.59 | 380 |
| 39 | 4,7-Dimethoxy | H | H | 1.30 | 422 |
| 40 | 5,6-Dichloro | H | H | 1.86 | 432 |
| 41 | 4-Bromo | H | H | 1.62 | 440 |
| 42 | 4,6-Difluoro | H | H | 1.44 | 398 |
| 43 | 5-Fluoro-6-chloro | H | H | 1.52 | 414 |
| 44 | 5,6-Difluoro | H | H | ND | 398 |
| 45 | 4,5,6,7-tetrafluoro | H | H | 1.54 | 434 |
| 46 | 4,7-Difluoro | H | H | 1.30 | 398 |
| 47 | 4-Methoxy | H | H | 1.23 | 392 |
| 48 | 5-Fluoro-7-bromo | H | H | ND | ND |
| 49 | 4-Fluoro-7-methyl | H | H | 1.34 | 394 |
| 50 | 4,6-Difluoro-5-Bromo | H | H | 1.63 | 477 |
| 51 | 4-Fluoro-7-trifluoroethoxy | H | H | 1.44 | 478 |
| 52 | 4-Methoxy-7-chloro | H | H | 1.36 | 426 |
| 53 | 4-ethoxy | H | H | 1.28 | 406 |
| 54 | 4-methoxy-7-bromo | H | H | 1.35 | 471 |
| 55 | 4-Bromo-7-fluoro | H | H | 1.45 | 458 |
| 56 | 4-Fluoro-7-methoxy | H | H | 1.29 | 410 |
| 57 | 4-Trifluoromethoxy-7-bromo | H | H | ND | 525 |
| 58 | 4-Fluoro | H | 4-NHC(O)OBu-t | 1.43 | 495 |
| 59 | 4-Chloro | H | 2-NHC(O)OBu-t | 1.56 | 511 |
| 60 | 4-Chloro | H | 3-NHC(O)OBu-t | 1.55 | 511 |
| 61 | 4-Chloro | H | 4-NHC(O)OBu-t | 1.54 | 511 |
| 62 | 4-Fluoro | H | 2-NHC(O)OBu-t | 1.42 | 495 |
| 63 | 4-Fluoro | H | 3-NHC(O)OBu-t | 1.44 | 495 |
| 64 | 4-Methoxy | Me | 3-NHC(O)OBu-t | 1.46 | 522 |
| 65 | 4-Fluoro | H | 2-Amino | 1.07 | 395 |
| 66 | 4-Fluoro | H | 3-Amino | 0.91 | 395 |
| 67 | 4-Fluoro | H | 4-Amino | 0.86 | 395 |
| 68 | 4-Chloro | H | 2-Amino | 1.21 | 411 |
| 69 | 4-Chloro | H | 3-Amino | 1.06 | 411 |
| 70 | 4-Chloro | H | 4-Amino | 1.03 | 411 |
| 71 | H | H | 2-Amino | 1.12 | 377 |
| 72 | H | H | 3-Amino | 0.93 | 377 |
| 73 | 4,7-Difluoro | H | 3-Amino | 0.98 | 413 |
| 74 | 4,7-Difluoro | Me | 3-Amino | 1.02 | 427 |
| 75 | 4,7-Difluoro | Me | 4-Amino | 1.01 | 427 |
| 76 | 4-Fluoro | Me | 3-Amino | 0.97 | 409 |
| 77 | 4-Methoxy-7-Chloro | Me | 3-Amino | 1.11 | 455 |
| 78 | 4-Methoxy-7-Chloro | Me | 4-Amino | 1.11 | 455 |
| 79 | 4-Methoxy | Me | 3-Amino | 0.93 | 421 |
| 80 | 4-Fluoro-7-Methoxy | Me | 3-Amino | 1.05 | 439 |
| 81 | 4-Fluoro-7-Methoxy | Me | 4-Amino | 1.04 | 439 |
| 82 | 4-Fluoro | H | 2-Acetoxy | 1.18 | 438 |
| 83 | 4-Fluoro | H | 3-Acetoxy | 1.17 | 438 |
| 84 | 4-Fluoro | H | 4-Acetoxy | 1.16 | 438 |
| 85 | 4-Chloro | H | 4-Acetoxy | 1.28 | 454 |
| 86 | 4-Chloro | H | 3-Acetoxy | 1.29 | 454 |
| 87 | 4-Fluoro | H | 2-OH | 1.17 | 396 |
| 88 | 4-Fluoro | H | 3-OH | 1.13 | 396 |
| 89 | 4-Fluoro | H | 4-OH | 1.09 | 396 |
| 90 | 4-Fluoro-7-carboxaldehyde | H | H | 0.79 | 408 |

(M + H)⁺ refers to the molecular ion peak in positive ionization mode.
ND means not determined.

Procedure for Synthesis of Compounds in Table 6

A. Preparation of Substituted Piperazines:

Preparation of 2-Alkylpiperazines

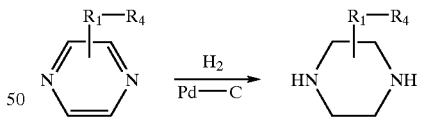

5 g of 2-alkyl pyrazine (46.3 mmol, from Pyrazine Specialties, Inc.) was dissolved in 200 ml of 95% ethanol with 500 mg 10% palladium on active carbon. The reaction mixture was hydrogenated under pressure (40–50 psi) for 2 days. The solid was filtered and removed. The filtrate was concentrated to afford 2-alkyl piperazine, which did not require further purification.

2-ethylpiperazine XIX: ¹H NMR (500 MHz, CD₃OD) δ 2.89 (t, J=15.05 Hz, 1H), 2.85 (d, J=15.11 Hz, 2H), 2.75 (t, J=11.80 Hz, 1H), 2.65 (t, J=11.90 Hz, 1H), 2.48 (m, 1H), 2.28 (t, J=6.12 Hz, 1H), 1.35 (m, 2H), 0.93 (t, J=7.55 Hz, 3H).

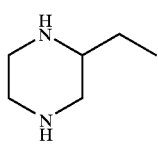
XIX 2-propylpiperazine XX: ¹H NMR (300 MHz, CDCl₃) δ 3.00–2.60 (m, 6H), 2.65 (t, J=10.20 Hz, 1H), 1.70 (m, 2H), 1.30 (m, 2H), 0.92 (t, J=6.9 Hz, 3H).

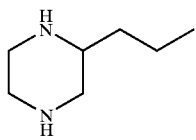
XX 2-iso-propylpiperazine XXI: ¹H NMR (300 MHz, CDCl₃) δ 3.03–2.30 (m, 7H), 1.50 (m, 1H), 0.91 (dd, J=6.60 & 6.60 Hz, 3H).

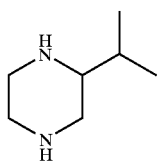
XXI 2-iso-butylpiperazine XXII: ¹H NMR (500 MHz, CD₃OD) δ 3.00–2.62 (m, 6H), 2.28 (t, J=10.55 Hz, 1H), 1.68 (m, 1H), 1.38 (m, 2H), 0.92 (dd, J=6.65 & 6.55 Hz, 3H).

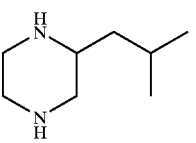
XXII 2-tert-butylpiperaine XXIII: ¹H NMR (500 MHz, CD₃OD) δ 2.96 (d, J=11.85 Hz, 2H), 2.80 (d, J=12.05 Hz, 1H), 2.74 (t, J=11.75 Hz, 1H), 2.63 (t, J=11.95 Hz, 1H), 2.41 (t, J=11.85 Hz, 1H), 2.31 (d, J=13.91 Hz, 1H), 0.92 (s, 9H).

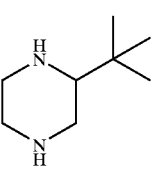
XXIII 2-pentylpiperazine XXIV:: ¹H NMR (500 MHz, CD₃OD) δ 2.89 (m, 2H), 2.83 (d, J=11.95 Hz, 1H), 2.75 (t, J=11.80 Hz, 1H), 2.65 (t, J=11.85 Hz, 1H), 2.56 (m, 1H), 2.28 (t, J=12.3 Hz, 1H), 1.35 (m, 8H), 0.90 (t, J=7.15 Hz, 3H).

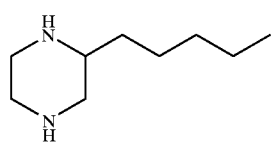
XXIV

Preparation of 2-Methoxycarbonyltetrahydropyrazine XXV

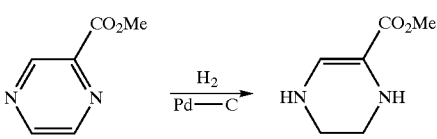
XXV 5 g of pyrazine carboxylic acid methyl ester (36.2 mmol, from Lancaster, Inc.) was dissolved in 200 ml of 95% ethanol with 500mg 10% palladium on active carbon. The reaction mixture was hydrogenated under pressure (40–50 psi) for 2 days. The solid was filtered and removed. The filtrate was concentrated to afford methoxycarbonyltetrahydropyrazine XXV, which was sufficiently pure enough for subsequent reactions.

2-Methoxycarbonyltetrahydropyrazine XXV: ¹H NMR (300 MHz, CD₃OD) δ 7.10(s, 1H), 4.84 (b, 2H), 3.66 (s, 3H), 3.29 (t, J=6.0 Hz, 2H), 3.08 (t, J=6.0 Hz, 2H); ¹³C NMR (75 MHz, CD₃OD) δ 166.1, 130.8, 105.4, 48.4, 40.6, 40.0; MS m/z: (M+H)⁺ calcd for C₆H₁₁N₂O₂: 143.08, found 143.09. HPLC retention time 0.11 (Method C).

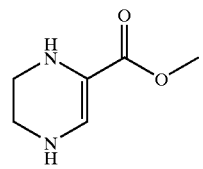
XXV

Preparation of 2-Ethoxycarbonylpiperazine XXVI

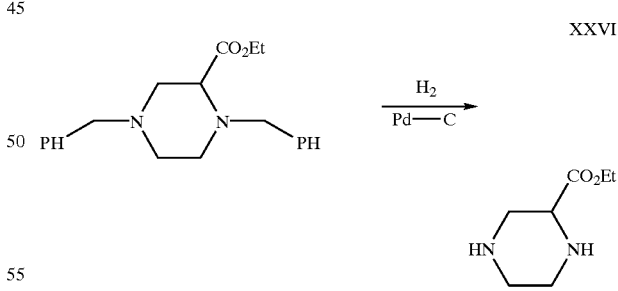
XXVI 5 g of N,N'-dibenzylpiperazine carbhoxylic acid ethyl ester (14.8 mmol, from Maybridge Chemical Company Ltd.) was dissolved in 200 ml of 95% ethanol with 500 mg 10% palladium on active carbon. The reaction mixture was hydrogenated under pressure (40–50 psi) for 2 days. The solid was filtered and removed. The filtrate was concentrated to afford 2-ethoxycarbonylpiperazine XXVI, which was sufficiently pure for subsequent reactions.

2-Ethoxycarbonylpiperazine XXVI: ¹H NMR (300 MHz, CD₃OD) δ 4.20 (q, J=7.20 Hz, 2H), 3.46–2.60 (m, 7H), 1.27

Preparation of 2-Trifluoromethylpiperazine XXVII

Step 1:

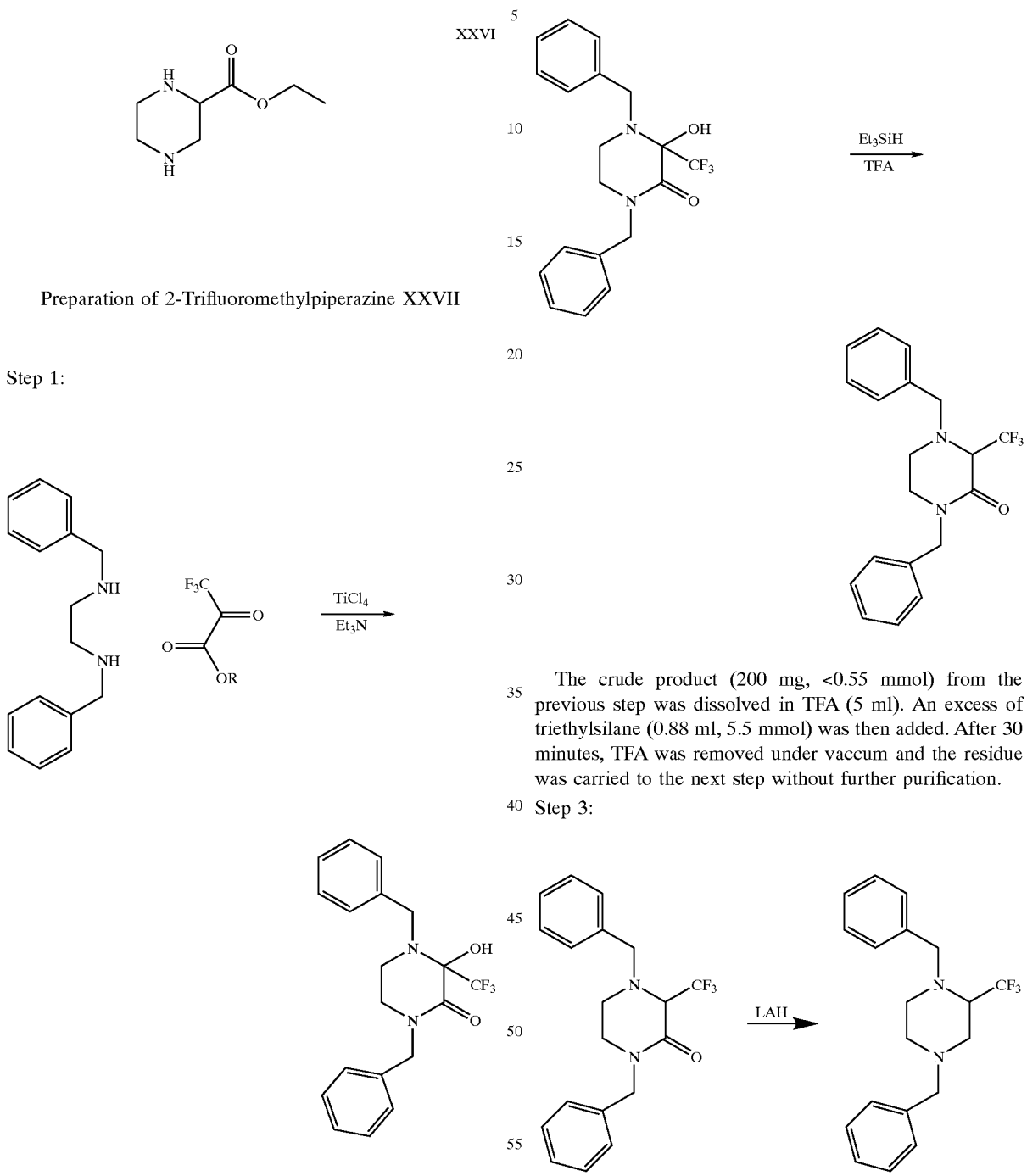

To a solution of N,N'-dibenzylethylenediamine (1.51 ml, 6.41 mmol), methyl 3,3,3-trifluoro-2-oxopropanate (1.0 g, 6.41 mmol) and triethylamine (1.78 ml, 12.8 mmol) in dichloromethane (100 ml) was added via a syringe titanium chloride (1M in CH$_2$Cl$_2$, 3.21 ml, 3.21 mmol). The reaction was stirred for 8 hours and the solvents were removed in vacuo. The residue was carried to the next step without further purification.

Step 2:

The crude product (200 mg, <0.55 mmol) from the previous step was dissolved in TFA (5 ml). An excess of triethylsilane (0.88 ml, 5.5 mmol) was then added. After 30 minutes, TFA was removed under vaccum and the residue was carried to the next step without further purification.

Step 3:

The crude product (<0.55 mmol) from step 2 was suspended in ether. LiAlH$_4$ (1M in THF, 0.55 ml, 0.55 mmol) was then added at room temperature. After stirring for 8 hours, the reaction was quenched with saturated NaHCO$_3$ solution. The aqueous layer was extracted with EtOAc. Organic layers were combined, dried over MgSO$_4$ and concentrated to give a residue, which was carried to the next step without purification.

Step 4:

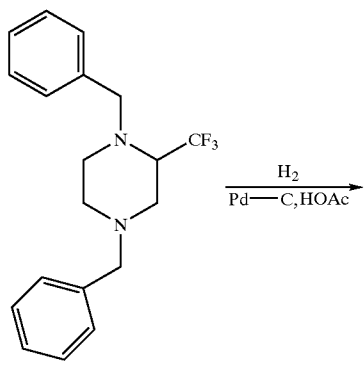

The crude product from the step 3 was dissolved in HOAc (20 ml) with 10 mg 10% palladium on active carbon. The reaction mixture was hydrogenated under pressure (40–50 psi) for 8 hours. The solid was filtered and removed. The filtrate was concentrated to afford 2-trifluoromethylpiperazine XXVII as a HOAc salt, which was pure enough for the further reactions.

2-Trifluoromethylpiperazine XXVII as its HOAc (2 equivalents) salt: $^1$H NMR (300 MHz, CD$_3$OD) δ 3.80–2.80 (m, 7H), 1.95 (s, 6H); $^{13}$C NMR (75 MHz, CD$_3$OD) δ 174.5, 53.8, 53.3, 42.7, 41.3, 40.8, 19.8; HRMS m/z: (M+H)$^+$ calcd for C$_5$H$_{10}$F$_3$N$_2$: 155.0796, found 155.0801.

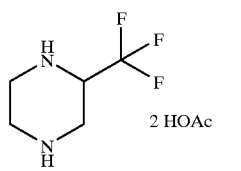

B. Mono-benzoylation of Piperazine Derivatives:

Unless otherwise started, substituted piperazine were mono-benzoylated using the following procedures:

Preparation of Benzoylpiperazines XXVIII and XXIX

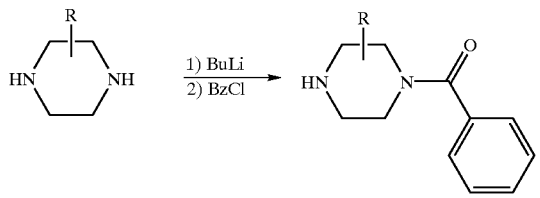

To a stirred solution of substituted piperazine (1.0 g, 11.6 mmol) in dry THF (50 ml) under argon was added 2.5M n-BuLi in THF (10.23 ml, 25.5 mmol) at room temperature. After stirring for 1 hour at room temperature, benzoyl chloride (1.27 ml, 11.0 mmol) was added to the solution of dianion and the reaction mixture was stirred for an additional 10 minutes. The reaction mixture was quenched with MEOH, and the solvents evaporated. The residue was partitioned between EtOAc (50 ml) and sat. NaHCO$_3$. The aqueous layer was saturated with NaCl and extracted with EtOAc (2×30 ml). The organic layer was dried over MgSO$_4$ and concentrated to afford the crude product benzoylpiperazine, which was generally of sufficient purity to be used directly without further purification. Chromatography on a silica gel column (EtOAc/MeOH/Et$_3$N, 7:3:1) gave the purified product.

Preparation of Benzoylpiperazine XXXIII and XLIII

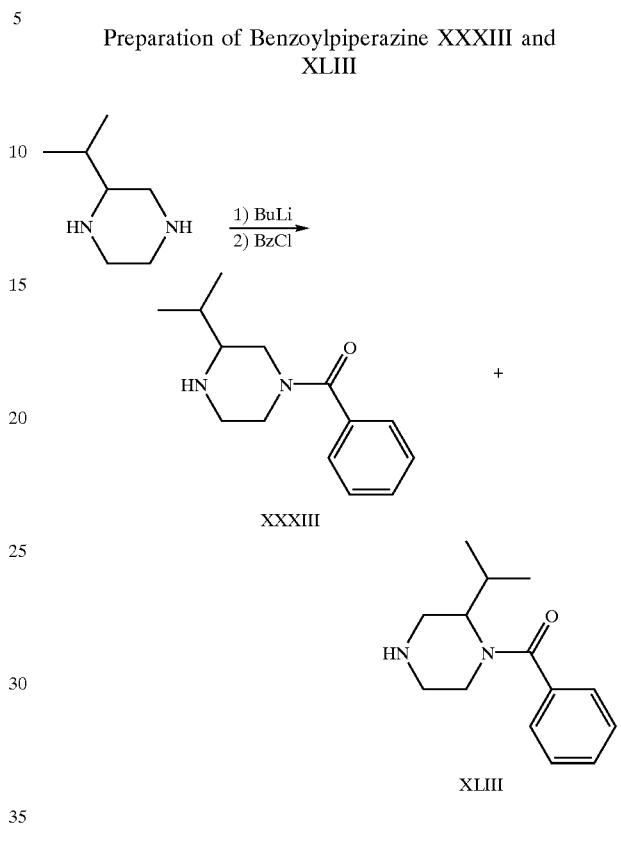

To a stirred solution of 2-isopropylpiperazine (1.0 g, 7.81 mmol) in dry THF (50 mL), maintained at room temperature under argon atmosphere, was added a solution of 2.5 M n-BuLi in THF (6.88 mL, 17.2 mmol). After stirring for 30 minutes at room temperature, benzoyl chloride (0.86 ml, 7.42 mmol) was added and the reaction mixture stirred for an additional 10 minutes. The reaction mixture was then quenched with MeOH, the solvents were evaporated in vacuo and the residue was purified by silica gel flash chromatography. Elution with a mixture of EtOAc and MeOH (1:1) afforded product XXXIII (0.62 g, 36% yield) and XLIII (0.3 g, 17% yield). Benzoyl piperazines XXXIII, XXXIV, XXXV, XXXVI, XXXVII were prepared using the same procedure as that outlined above.

Preparation of Benzoylpiperazines XXXI, XXXII, XXXVIII,

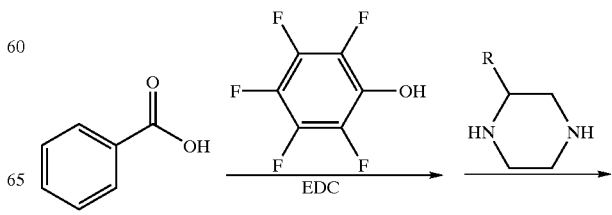

Preparation of N-Benzoyl-cis-2,6-dimethylpiperazine XLVII

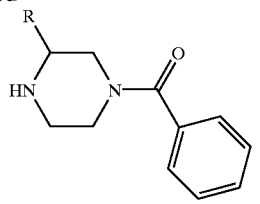 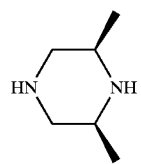 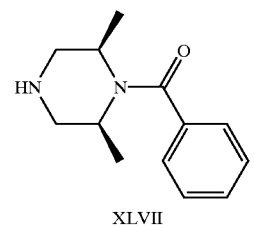

XLVII

Commercially available benzoic acid (4.8 g, 40 mmol), pentafluorophenol (7.4 g, 40 mmol) and EDAC (7.6 g, 40 mmol) were combined in 60 ml of dry DMF. The mixture was stirred at room temperature for 2 hours. To this solution, 2-methylpiperazine (4.0 g, 40 mmol) in 30 ml of DMF was added slowly and the reaction mixture was stirred at room temperature for 12 hours.

Evaporation of DMF gave a residue which was diluted with 400 ml of EtOAc and washed with water (2×100 nm). The organic phase was dried over anhydrous MgSO4 and concentrated in vacuo to provide a crude product, which was purified by column chromatography with EtOAc/MeOH (100:1) and then EtOAc/MeOH (10:1) to give 4.8 g of product XX in 60% yield.

Preparation of Benzoylpiperazine XXX

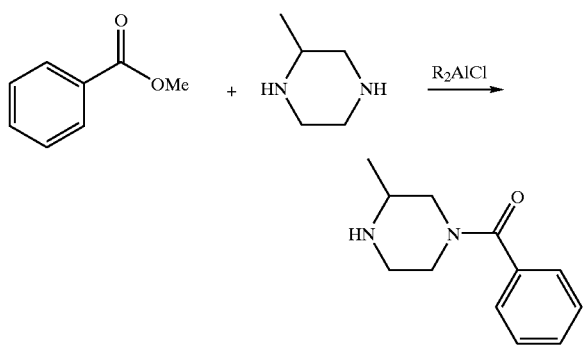

To a stirred solution of 2-methylpiperazine (10.0 g, 0.1 mol) in dry $CH_2Cl_2$ (500 ml) under argon was added a solution of 1.0 M $Me_2AlCl$ or $Et_2AlCl$ in hexanes (100 ml, 0.1 mmol) and methyl benzoate (12.4 ml, 0.1 mmol) at room temperature. The reaction mixture was then stirred for 2 days before 2N NaOH (200 ml) was added. Aqueous layer was extracted with EtOAc (3×100 ml). The combined organic layer was dried over $MgSO_4$ and concentration of solution provided 20.0 g of crude product (98%), with was pure enough for the further reactions.

To a stirred solution of 2,6-di-methylpiperazine (0.82 g, 7.2 mmol) in dry THF (50 mL), maintained at room temperature under an argon atmosphere, was added a solution of 2.5 M n-BuLi in THF (6.3 mL, 15.8 mmol). After stirring for 30 minutes at room temperature, trimethylsilyl chloride (1.0 mL, 7.9 mmol) was added and the reaction mixture stirred for one hour before the addition of benzoyl chloride (0.80 mL, 6.9 mmol). After 10 minutes, the reaction mixture was quenched with MeOH and the solvents were evaporated in vacuo. The residue was purified by silica gel flash column chromatography eluting with a mixture of EtOAc and MeOH (1:1) to provide product XLVII (1.48 g, 99% yield). Benzoyl piperazines XL, XLI, XLII, XLIII, XLIV, XLV, and XLVI were synthesised using the same procedure as outlined above.

Preparation of Benzoylpiperazine XXXIX

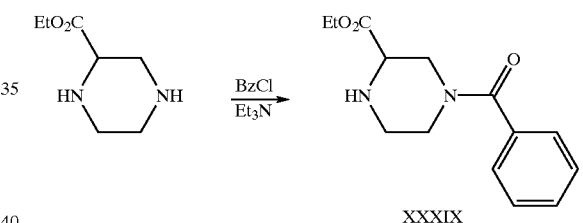

XXXIX

To a stirred solution of 2-ethoxycarbonylpiperazine (4.6 g, 29.1 mmol) in dry methylene chloride (200 mL), was added benzoyl chloride (3.55 ml, 29.1 mmol) and triethylamine (2 ml) sequentially. After stirring for 8 hours at room temperature, a saturated $NaHCO_3$ solution was added and the aqueous phase was extracted with ethyl acetate (3×200 ml). The organic layers were combined, dried over $MgSO_4$ and concentrated to give a crude mixture, which included the desired product XXXIX. The crude was then used for the further reaction without purification.

Preparation of Benzoylpiperazine XLVIII

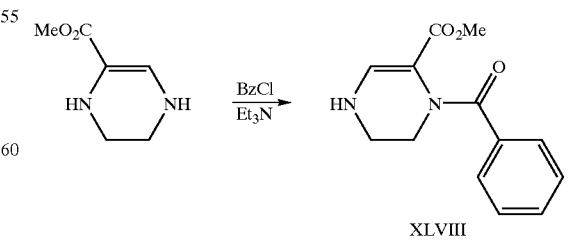

XLVIII

To a stirred solution of 2-methoxycarbonyltetrahydropyrazine (1.0 g, 7.0 mmol) in dry methylene chloride (50 ml), was added benzoyl chloride 0.76 ml, 6.7 mmol) and triethylamine (5 ml) sequentially. After stirring for 8 hours at room temperature, a saturated NaHCO$_3$ solution was added and the aqueous phase was extracted with ethyl acetate (3×20 ml). The organic layers were combined, dried over MgSO$_4$ and concentrated to give a crude mixture, which included the desired product XLVII. The crude was then used for the further reaction without purification.

Preparation of 3-Hydroxylmethyl-benzoylpiperazine XLIX

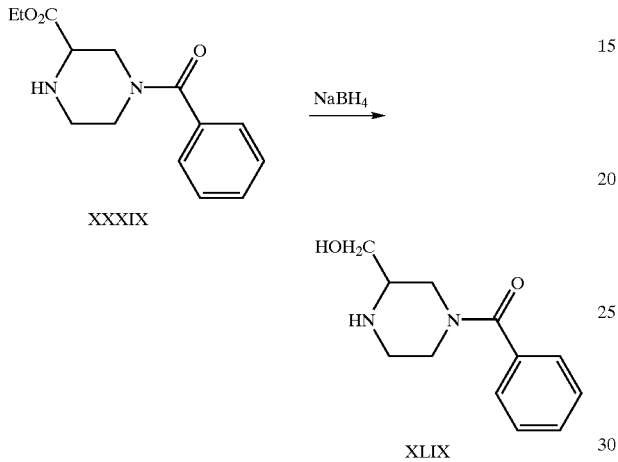

To a stirred solution of 3-ethoxycarbonyl-benzoylpiperazine XLIX (200 mg, 0.76 mmol) in THF (5 ml), was added lithium chloride (36 mg, 0.84 mmol), NaBH4 (32 mg, 0.84 mmol) and EtOH (5 ml) sequentially. After stirring for 8 hours at room temperature, a saturated NaHCO$_3$ solution was added and the aqueous phase was extracted with ethyl acetate (3×20 ml). The organic layers were combined, dried over MgSO$_4$ and concentrated to give a crude mixture, which was used for the further reaction without purification.

Characterization of Mono-Benzoylated Piperazine Derivatives

N-Benzoylpiperazine XXVIII: $^1$H NMR (300 MHz, CD$_3$OD) δ 7.37 (m, 5H), 3.73 (br s, 2H), 3.42 (br s, 2H), 2,85 (br s, 4H); $^{13}$C NMR (75 MHz, CD$_3$OD) δ 170.9, 135.0, 129.6, 128.2, 126.5, 44.5; HRMS m/z: (M+H)$^+$ calcd for C$_{11}$H$_{15}$N$_2$O 191.1184, found 191.1181.

XXVIII

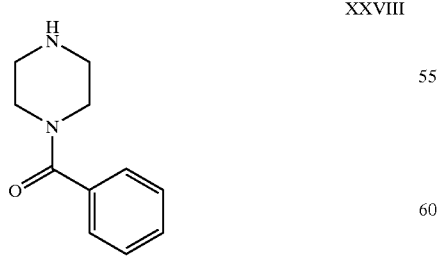

N-(Benzoyl)-trans-2,5-Dimethylpiperazine XXIX. $^1$H NMR (300 MHz, CD$_3$OD) δ 7.50–7.28 (m, 5H), 4.38 (br s, 1H), 3.70 (br s, 1H), 3.40–3.20 (m, 3H), 2.57 (dd, 1H, J=12.96, 1.98 Hz), 1,35 (d, 3H, J=6.87 Hz), 1.22 (d, 3H, J=6.78 Hz); $^{13}$C NMR (75 MHz, CD$_3$OD) δ 171.9, 135.9, 129.3, 128.3, 126.0, 47.6, 46.7, 43.8, 42.3, 14.7, 14.3; HRMS m/z: (M+H)$^+$ calcd for C$_{13}$H$_{19}$N$_2$O 219.1497, found 219.1499.

XXIX

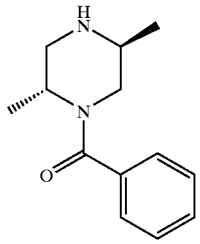

N-(Benzoyl)-3-methylpiperazine XXX. $^1$H NMR (300 MHz, CD$_3$OD) δ 7.45 (m, 5H), 4.50 (d, 1H, J=10.8 Hz), 3.60 (b, 1H), 3.33–2.60 (m, 5H), 1.16–0.98 (m, 3H); $^{13}$C NMR (75 MHz, CD$_3$OD) δ 170.9, 135.3, 129.6, 128.3, 126.5, 54.0, 50.6, 50.1, 45.0, 44.4, 41.7, 17.50; HRMS m/z: (M+H)$^+$ calcd for C$_{12}$H$_{17}$N$_2$O 205.1341, found 205.1336.

XXX

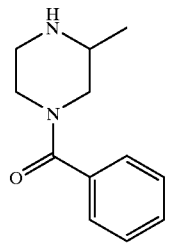

N-(Benzoyl)-3-ethylpiperazine XXXI. $^1$H NMR (300 MHz, CD$_3$OD) δ 7.47 (m, 5H), 4.55 (b, 1H), 3.64 (b, 1H), 3.36–2.59 (m, 5H), 1.51–0.82 (m, 5H); $^{13}$C NMR (75 MHz, CD$_3$OD) δ 171.5, 135.8, 130.1, 128.8, 126.9, 57.2, 56.7, 52.9, 47.1, 45.5, 42.5, 26.4, 26.0, 9.3; HRMS m/z: (M+H)$^+$ calcd for C$_{13}$H$_{19}$N$_2$O 219.1497, found 219.1495.

XXXI

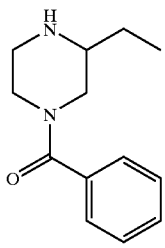

N-(Benzoyl)-3-propylpiperazine XXXII. $^1$H NMR (300 MHz, CD$_3$OD) δ 7.45 (m, 5H), 4.53 (t, 1H, J=13.44 Hz), 3.64 (b, 1H), 3.17–2.64 (m, 5H), 1.46–0.86 (m, 7H); $^{13}$C NMR (75 MHz, CD$_3$OD) δ 171.4, 135.9, 130.1, 128.8, 126.9, 55.4, 54.9, 53.2, 45.6, 45.0, 42.6, 35.8, 35.3, 18.8, 13.4; HRMS m/z: (M+H)$^+$ calcd for C$_{14}$H$_{21}$N$_2$O 233.1654, found 233.1652.

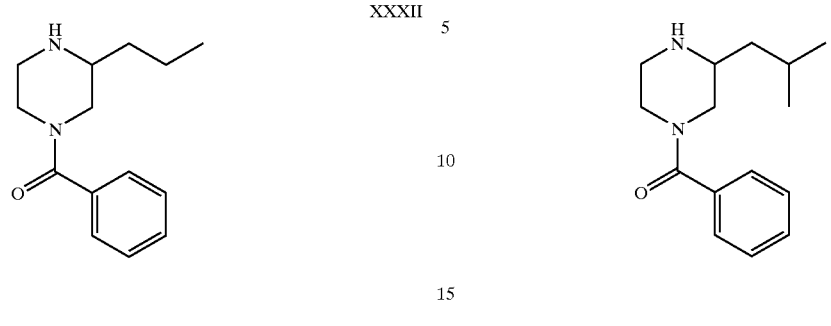

XXXII

XXXV

N-(Benzoyl)-3-iso-propylpiperazine XXXIII. $^1$H NMR (300 MHz, CD$_3$OD) δ 7.45 (m, 5H), 4.30 (m, 1H), 3.64 (m, 1H), 3.10–2.40 (m, 5H), 1.70–0.75 (m, 7H); $^{13}$C NMR (75 MHz, CD$_3$OD) δ 171.5, 135.9, 130.5, 129.3, 126.9, 61.7, 61.1, 51.2, 45.9, 45.4, 42.5, 31.2, 30.7, 18.3; HRMS m/z: (M+H)$^+$ calcd for C$_{14}$H$_{21}$N$_2$O 233.1654, found 233.1654.

N-(Benzoyl)-3-tert-butylpiperazine XXXVI. $^1$H NMR (300 MHz, CD$_3$OD) δ 7.45 (m, 5H), 4.70 (m, 1H), 3.66 (m, 1H), 3.17–2.43 (m, 5H), 1.17–0.84 (m, 9H); $^{13}$C NMR (75 MHz, CD$_3$OD) δ 171.6, 135.9, 131.0, 129.4, 126.9, 65.3, 64.6, 49.6, 46.5, 45.9, 43.7, 42.3, 32.7.25.7; HRMS m/z: (M+H)$^+$ calcd for C$_{15}$H$_{23}$N$_2$O 247.1810, found 247.1815.

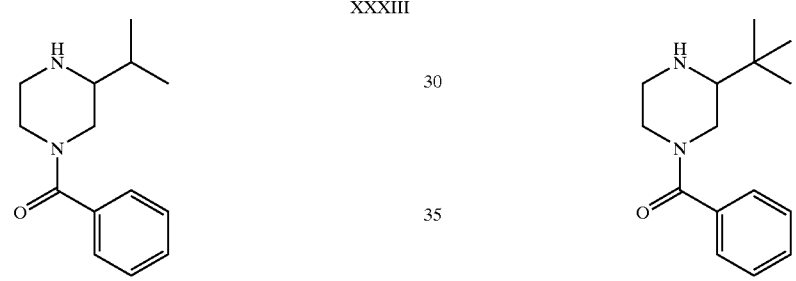

XXXIII

XXXVI

N-(Benzoyl)-3-pentylpiperazine XXXIV. $^1$H NMR (300 MHz, CD$_3$OD) δ 7.47 (m, 5H), 4.50 (t, 1H, J=17.85 Hz), 3.62 (b, 1H), 3.17–2.64 (m, 5H), 1.46–0.87 (m, 11H); $^{13}$C NMR (75 MHz, CD$_3$OD) δ 171.4, 135.9, 130.1, 129.3, 126.8, 55.6, 55.2, 53.1, 45.6, 45.0, 42.5, 33.6, 33.0, 32.0, 28.9, 25.9, 25.3, 22.6, 13.4; HRMS m/z: (M+H)$^+$ calcd for C$_{16}$H$_{25}$N$_2$O 261.1967, found 261.1969.

N-(Benzoyl)-cis-3,5-di-methylpiperazine XXXVII. $^1$H NMR (300 MHz, CD$_3$OD) δ 7.43 (m, 5H), 4.55 (d, 1H,J= 12.0 Hz), 3.55 (d, 1H, J=9.60 Hz), 2.74–2.38 (m, 5H), 1.13–0.94 (m, 6H); $^{13}$C NMR (75 MHz, CD$_3$OD) δ 170.5, 135.5, 129.6, 128.3, 126.6, 53.4, 50.9, 50.2, 17.7, 17.3; HRMS m/z: (M+H)$^+$ calcd for C$_{13}$H$_{19}$N$_2$O 219.1497, found 219.1492.

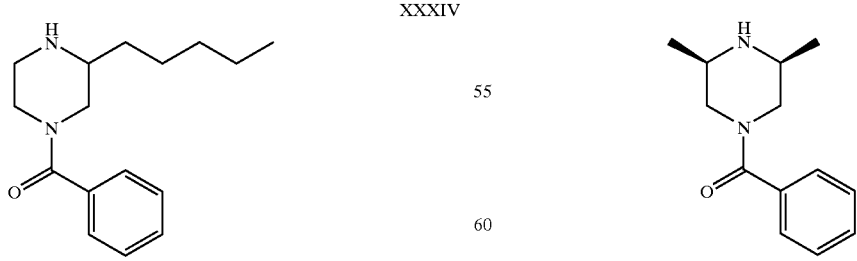

XXXIV

XXXVII

N-(Benzoyl)-3-iso-butylpiperazine XXXV. MS m/z: (M+H)$^+$ calcd for C$_{15}$H$_{23}$N$_2$O: 247.18, found 247.22. HPLC retention time: 1.04 minutes (Method C).

N-(Benzoyl)-3-trifluoromethylpiperazine XXXVIII. MS m/z: (M+H)$^+$ calcd for C$_{12}$H$_{14}$F$_3$N$_2$O: 259.11, found 259.05. HPLC retention time: 0.65 minutes (Method A).

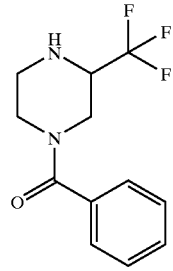

XXXVIII

N-(Benzoyl)-3-ethoxycarbonylpiperazine XXXIX. MS m/z: (M+H)$^+$ calcd for $C_{14}H_{19}N_2O_3$: 263.14, found 263.20. HPLC retention time: 0.80 minutes (Method C).

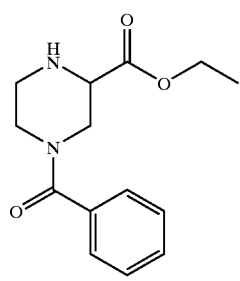

XXXIX

N-(Benzoyl)-2-methylpiperazine XL. $^1$H NMR (300 MHz, CD$_3$OD) δ 7.47 (m, 5H), 3.30–2.70 (m, 7H), 1.36 (d, 3H, J=6.90 Hz); $^{13}$C NMR (75 MHz, CD$_3$OD) δ 171.0, 135.4, 129.7, 128.5, 126.3, 48.5, 44.3, 14.5; HRMS m/z: (M+H)$^+$ calcd for $C_{12}H_{17}N_2O$ 205.1341, found 205.1341.

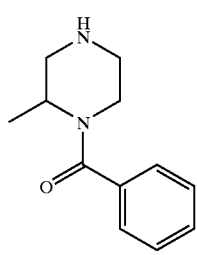

XL

N-(Benzoyl)-2-ethylpiperazine XLI. $^1$H NMR (300 MHz, CD$_3$OD) δ 7.49 (m, 5H), 3.34–2.80 (m, 7H), 2.10–1.70 (m, 2H), 0.85 (b, 3H); $^{13}$C NMR (75 MHz, CD$_3$OD) δ 171.5, 135.1, 129.8, 128.5, 126.5, 48.5, 46.0, 43.9, 21.8, 9.6; HRMS m/z: (M+H)$^+$ calcd for $C_{13}H_{19}N_2O$ 219.1497, found 219.1501.

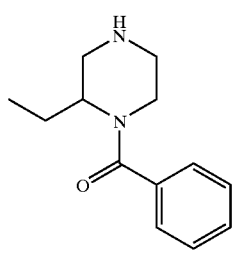

XLI

N-(Benzoyl)-2-propylpiperazine XLII. $^1$H NMR (300 MHz, CD$_3$OD) δ 7.50 (m, 5H), 3.60–2.80 (m, 7H), 2.10–0.70 (m, 7H); 13C NMR (75 MHz, CD$_3$OD) δ 172.5, 135.0, 129.9, 128.6, 126.7, 48.7, 46.2, 43.8, 30.9, 18.9, 13.1; HRMS m/z: (M+H)$^+$ calcd for $C_{14}H_{21}N_2O$ 233.1654, found 233.1650.

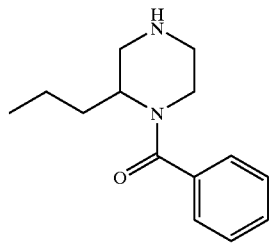

XLII

N-(Benzoyl)-2-iso-propylpiperazine XLIII. $^1$NMR (300 MHz, CD$_3$OD) δ 7.50 (b, 5H), 4.40 (m, 1H), 3.60–2.50 (m, 6H), 1.10–0.70 (m, 7H); $^{13}$C NMR (75 MHz, CD$_3$OD) δ 171.1, 135.0, 130.0, 128.7, 127.0, 60.6, 54.1, 43.9, 42.3, 25.4, 19.3, 18.4; HRMS m/z: (M+H)$^+$ calcd for $C_{14}H_{21}N_2O$ 233.1654, found 233.1653.

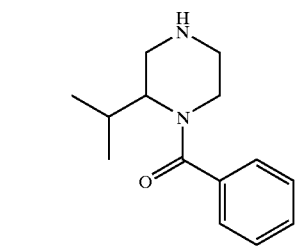

XLIII

N-(Benzoyl)-2-pentylpiperazine XLIV. $^1$H NMR (300 MHz, CD$_3$OD) δ 7.47 (b, 5H), 3.40–2.80 (m, 7H), 2.10–0.70 (m, 11H); 13C NMR (75 MHz, CD$_3$OD) δ 71.2, 135.0, 129.9, 128.6, 126.7, 48.7, 46.2, 43.8, 31.0, 28.8, 25.3, 22.2, 13.4; HRMS m/z: (M+H)$^+$ calcd for $C_{16}H_{25}N_2O$ 261.1967, found 261.1970.

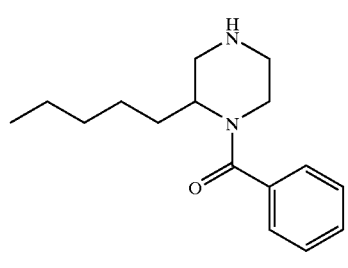

XLIV

N-(Benzoyl)-2-iso-butylpiperazine XLV. MS m/z: (M+H)$^+$ calcd for $C_{15}H_{23}N_2O$: 247.18, found 247.23. HPLC retention time: 1.06 minutes (Method C).

HPLC retention time: 0.32 minutes (Method C).

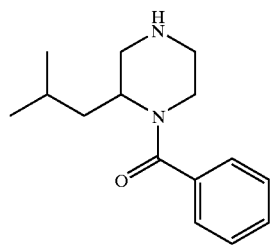

XLV

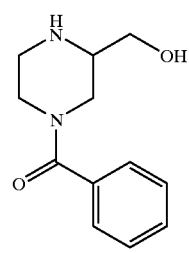

XLIX

N-(Benzoyl)-2-tert-butylpiperazine XLVI. $^1$H NMR (300 MHz, CD$_3$OD) δ 7.45 (m, 5H), 4.53 (t, 1H, J=5.70 Hz), 3.60–2.60 (m, 6H), 1.14 (s, 9H); $^{13}$C NMR (75 MHz, CD$_3$OD) δ 173.5, 136.7, 129.9, 128.9, 126.6, 55.9, 44.8, 44.5, 42.7, 36.5, 27.8; HRMS m/z: (M+H)$^+$ calcd for C$_{15}$H$_{23}$N$_2$O 247.1810, found 247.1808.

C. Coupling of Mono-benzoyl Piperazines with Glyoxyl Chlorides

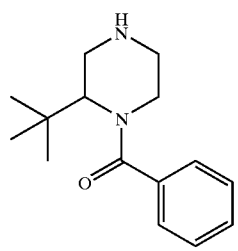

XLVI

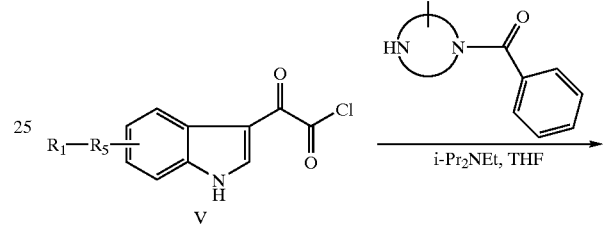

N-(Benzoyl)-cis-2,6-di-methylpiperazine XLVII. $^1$H NMR (300 MHz, CD$_3$OD) δ 7.45 (m, 5H), 4.18 (b, 2H), 2.85 (m, 4H), 1.33 (d, 6H, J=6.90 Hz); $^{13}$C NMR (75 MHz, CD$_3$OD) δ 172.0, 136.7, 128.9, 128.3, 125.8, 49.1, 47.1, 19.2; HRMS m/z: (M+H)$^+$ calcd for C$_{13}$H$_{19}$N$_2$O 219.1497, found 219.1491.

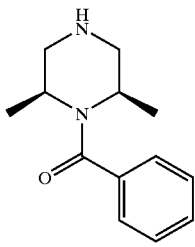

XLVII

To a solution of indole glyoxoyl chloride V (1 eq) in dry CH$_2$Cl$_2$ was added substituted benzoylpiperazine (1 eq) at room temperature. The mixture was then cooled down to 0° C., followed by dropwise addition of diisopropylamine (1.3 eq). After 5 min., the reaction mixture was warmed to room temperature and was shaken for 3 hr. The resulting crude products XL were purified by preparative HPLC and characterized as shown in Table 6.

N-(Benzoyl)-3-methoxycarbonyltetrahydropyrazine XLVIII. MS m/z: (M+H)$^+$ calcd for C$_{13}$H$_{15}$N$_2$O$_3$: 247.11, found 247.13. HPLC retention time: 1.00 minutes (Method C).

Preparation of N-(Benzoyl)-3-hydroxylmethyl-N'-[(7-methoxycarbonyl-indol-3-yl)-oxoacetyl]-piperazine Example 98

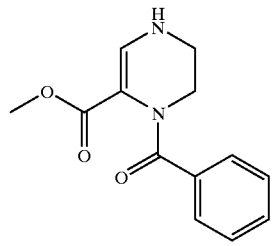

XLVIII

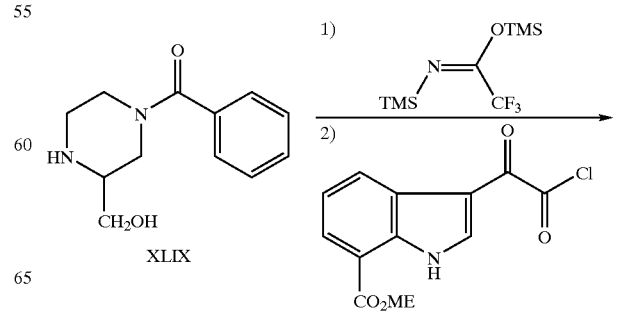

3-Hydroxylmethyl-benzoylpiperazine XLIX. MS m/z: (M+H)$^+$ calcd for C$_{12}$H$_{17}$N$_2$O$_2$: 221.13, found 221.17.

71
-continued

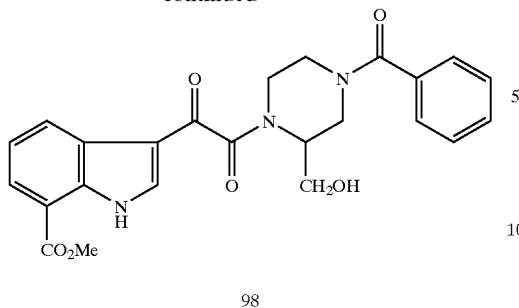

98

To a stirred solution of 3-hydroxylmethyl-benzoylpiperazine XLIX (8.0 mg, 0.036 mmol) in acetonitrile (5 ml) was added BSTFA (8.1 mg, 0.036 mmol). After stirring for 30 minutes at room temperature, (7-methoxycarbonyl-indol-3-yl)-oxoacetyl chloride (8.1 mg, 0.036 mmol) and pyridine (0.5 ml) were added. The reaction was stirred for another 2 hours at room temperature. Concentration under vaccum provided a residue, which was then purified by Shimazu HPLC purification system to give 2 mg of N-(benzoyl)-3-hydroxylmethyl-N'-[(7-methoxycarbonyl-indol-3-yl)-oxoacetyl]-piperazine (Example 98).

D. Hydrolysis of Ester Group to Acid Group:

Preparation of N-(Benzoyl)-3-hydroxycarbonyl-N'-[(4-fluoro-indol-3-yl)-oxoacetyl]-piperazine
(Example 101)

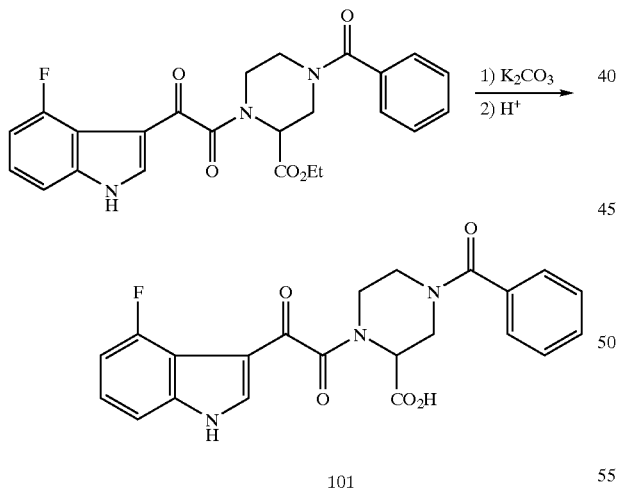

101

To a stirred solution of N-(benzoyl)-3-ethoxycarbonyl-N'-[(4-fluoro-indol-3-yl)-oxoacetyl]-piperazine (100 mg, 0.02 mmol) in methanol (1 ml) and water (1 ml), was added potassium carbonate (9 mg, 0.06 mmol). After stirring for 8 hours at room temperature, the product was concentrated in vacuo to give a residue which was purified by preparative HPLC to yield 2 mg of N-(benzoyl)-3-hydroxycarbonyl-N'-[(4-fluoro-indol-3-yl)-oxoacetyl]-piperazine (Example 101).

72

Preparation of N-(Benzoyl)-3-(R)-methyl-N'-[(7-hydroxycarbonyl-indol-3-yl)-oxoacetyl]-piperazine
(Example 137)

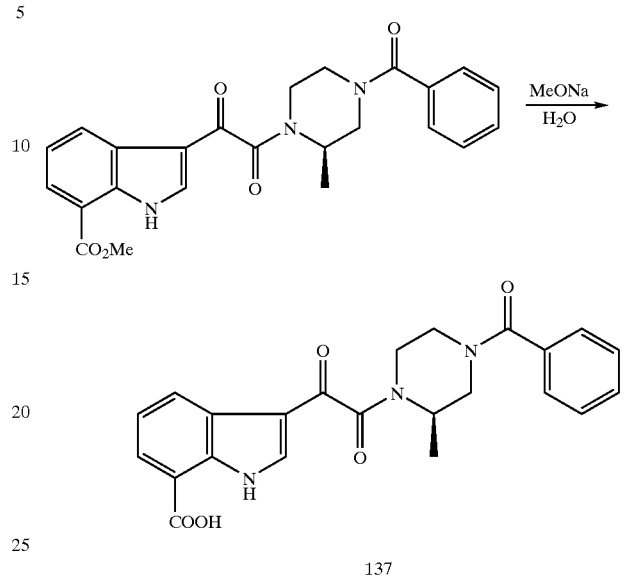

137

To a stirred solution of N-(benzoyl)-3-(R)-methyl-N'-[(7-methoxycarbonyl-indol-3-yl)-oxoacetyl]-piperazine (20 mg, 0.05 mmol) in 0.5N sodium methoxide in methanol (5 ml), was added 0.5 ml of water. After stirring for 8 hours at room temperature, 10% HCl was added to the reaction mixture to pH=6. N-(benzoyl)-3-(R)-methyl-N '-[(7-hydroxycarbonyl-indol-3-yl)-oxoacetyl]-piperazine (Example 137) precipated out from the solution, which was collected via filtration.

TABLE 6

| Example # | R1 | W | HPLC retention time (min) | MS Data (M+H)+ |
|---|---|---|---|---|
| 91 | 4-Fluoro | (3-methylpiperazine) | 1.27$^A$ | 394 |
| 92 | 4-Fluoro | (2,5-dimethylpiperazine) | 1.32$^A$ | 408 |

TABLE 6-continued

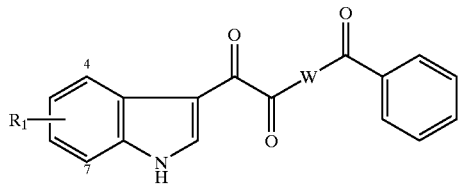

| Example # | R1 | W | HPLC retention time (min) | MS Data (M+H)+ |
|---|---|---|---|---|
| 93 | 4-Fluoro | (S)-2-methylpiperazine | 0.92[B] | 394 |
| 94 | 4-Fluoro | (R)-2-methylpiperazine | 1.32[A] | 394 |
| 95 | 4-Fluoro | 2-methylpiperazine | 1.32[A] | 394 |
| 96 | 4-Fluoro | 2,5-dimethylpiperazine | 1.29[A] | 408 |
| 97 | 4-Fluoro | 2,6-dimethylpiperazine | 1.29[A] | 408 |
| 98 | 4-COOMe | 3-(hydroxymethyl)piperazine | 1.44[A] | 450 |
| 99 | 4-Fluoro | 3-(hydroxymethyl)piperazine | 1.23[A] | 432 |
| 100 | 7-COOMe | 3-(ethoxycarbonyl)piperazine | 1.60[A] | 492 |

TABLE 6-continued

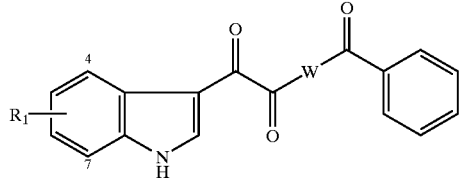

| Example # | R1 | W | HPLC retention time (min) | MS Data (M+H)+ |
|---|---|---|---|---|
| 101 | 4-Fluoro | 3-carboxypiperazine | 1.25[A] | 424 |
| 102 | 7-COOMe | (R)-2-methylpiperazine | 1.41[B] | 434 |
| 103 | 7-COOMe | (S)-2-methylpiperazine | 1.39[A] | 434 |
| 104 | 7-COOMe | 2-methylpiperazine | 1.57[A] | 434 |
| 105 | 7-OMe | (R)-2-methylpiperazine | 1.55 | 406 |
| 106 | 4,7-difluoro | (R)-2-methylpiperazine | 1.33 | 412 |
| 107 | 4,5,6,7-tetrafluoro | (R)-2-methylpiperazine | 1.57 | 448 |
| 108 | 4,5,6,7-tetrafluoro | (S)-2-methylpiperazine | 1.58 | 448 |
| 109 | 7-Nitro | (R)-2-methylpiperazine | 1.48 | 421 |

TABLE 6-continued

Structure: Indole (with R₁ substituent, positions 4-7) at 3-position connected via C(=O)-C(=O)-W-C(=O)-phenyl

| Example # | R1 | W | HPLC retention time (min) | MS Data (M+H)⁺ |
|---|---|---|---|---|
| 110 | 7-Ethyl | (S)-3-methylpiperazine | 1.58 | 404 |
| 111 | 7-OMe | (S)-3-methylpiperazine | 1.39 | 406 |
| 112 | 7-Nitro | (S)-3-methylpiperazine | 1.49 | 421 |
| 113 | 6-Chloro | (S)-3-methylpiperazine | 1.55 | 411 |
| 114 | 5,6-dichloro | (S)-3-methylpiperazine | 1.71 | 446 |
| 115 | 4-Chloro | (S)-3-methylpiperazine | 1.45 | 410 |
| 116 | 4-Chloro | (R)-3-methylpiperazine | 1.45 | 410 |
| 117 | 5,6-dichloro | (R)-3-methylpiperazine | 1.72 | 446 |
| 118 | 5-Fluoro | (S)-3-methylpiperazine | 1.43 | 394 |
| 119 | 7-Ethyl | (R)-3-methylpiperazine | 1.55 | 1.67 |
| 120 | 4-Bromo | (R)-3-methylpiperazine | 1.48 | 456 |
| 121 | 7-COOMe | methyl pyrazine-2-carboxylate | 1.62ᴬ | 476 |
| 122 | 4-Br | (S)-3-methylpiperazine | 1.48 | 456 |
| 123 | 5-Fluoro | (R)-3-methylpiperazine | 1.42 | 394 |
| 124 | 6-Chloro | (R)-3-methylpiperazine | 1.57 | 410 |
| 125 | 7-COOMe | 3-ethylpiperazine | 1.61ᴬ | 448 |
| 126 | 7-COOMe | 2-(2-ethyl)piperazine | 1.69ᴬ | 462 |

TABLE 6-continued

| Example # | R1 | W | HPLC retention time (min) | MS Data (M+H)+ |
|---|---|---|---|---|
| 127 | 7-COOMe | piperazine with isopropyl | 1.67[A] | 462 |
| 128 | 7-COOMe | piperazine with propyl | 1.69[A] | 462 |
| 129 | 7-COOMe | piperazine with isobutyl | 1.76[A] | 476 |
| 130 | 7-COOMe | piperazine with isobutyl | 1.76[A] | 476 |
| 131 | 7-COOMe | piperazine with tert-butyl | 1.71[A] | 476 |
| 132 | 7-COOMe | piperazine with pentyl | 1.84[A] | 490 |
| 133 | 7-COOMe | piperazine with pentyl | 1.85[A] | 490 |
| 134 | 7-COOMe | piperazine with tert-butyl | 1.76[A] | 476 |
| 135 | 4-OMe | piperazine with methyl | 1.24 | 406 |
| 136 | 4-OMe | piperazine with methyl | 1.24 | 406 |
| 137 | 7-COOH | piperazine with methyl | 1.43[A] | 420 |
| 138 | 4-Fluoro-7-methyl | piperazine with methyl | 1.37 | 408 |
| 139 | 7-COOMe | piperazine with ethyl | 1.62[A] | 448 |
| 140 | 7-Fluoro | piperazine with methyl | 1.74 | 394 |

TABLE 6-continued

| Example # | R1 | W | HPLC retention time (min) | MS Data (M+H)+ |
|---|---|---|---|---|
| 141 | 7-Fluoro | (piperazine, methyl) | 1.74 | 394 |
| 142 | 7-COOMe | (piperazine, CF3) | 1.65[A] | 488 |
| 143 | 4-Fluoro | (piperazine, CF3) | 1.42[A] | 488 |
| 144 | 4-fluoro-7-bromo | (piperazine, methyl) | 1.12 | N.D |
| 145 | 4-Fluoro-7-COOMe | (piperazine, methyl) | 1.51 | 452 |
| 146 | 4-Fluoro-7-COOMe | (piperazine, methyl) | 1.39 | 438 |
| 147 | 4-Fluoro-7-OMe | (piperazine, methyl) | 1.31 | 424 |

Note in Table 6, and other tables herein, in the HPLC column, numbers with superscript "A", "B," or "C" refer to the HPLC method used (i.e. Methods A, B or C, respectively).

Preparation of Examples 148 –194 in Table 7

Step A.

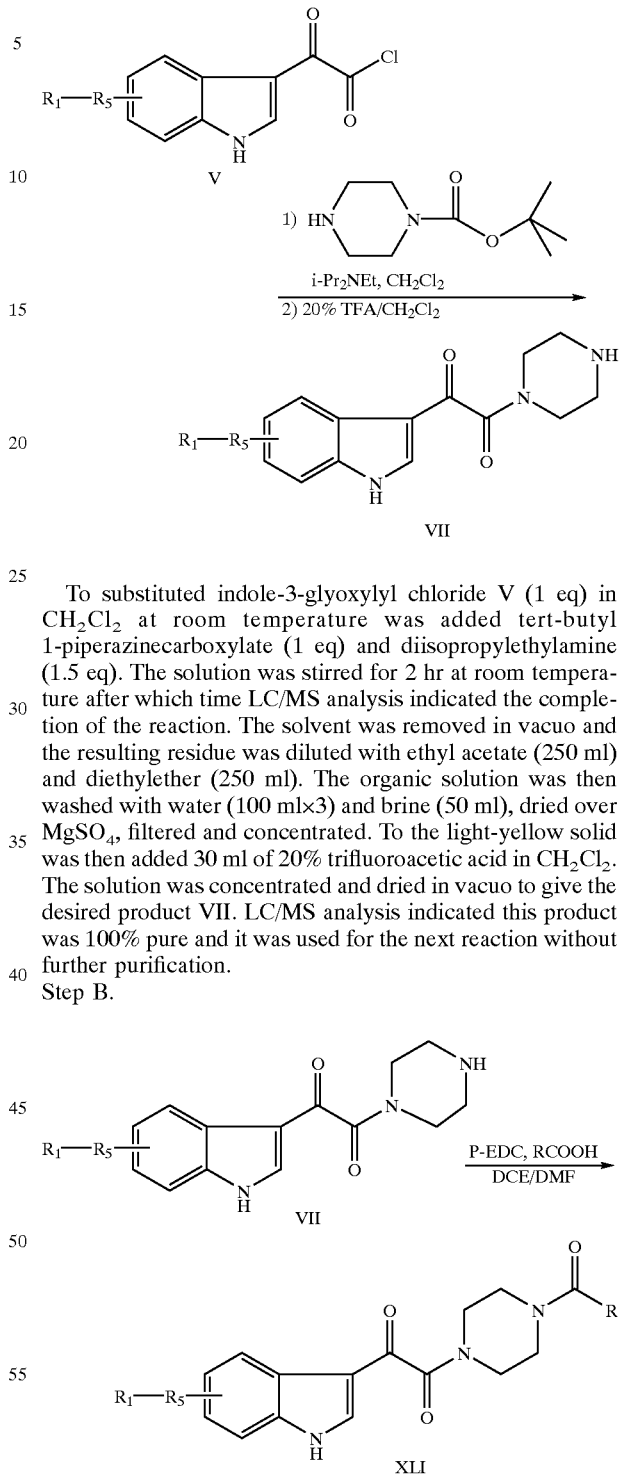

To substituted indole-3-glyoxylyl chloride V (1 eq) in $CH_2Cl_2$ at room temperature was added tert-butyl 1-piperazinecarboxylate (1 eq) and diisopropylethylamine (1.5 eq). The solution was stirred for 2 hr at room temperature after which time LC/MS analysis indicated the completion of the reaction. The solvent was removed in vacuo and the resulting residue was diluted with ethyl acetate (250 ml) and diethylether (250 ml). The organic solution was then washed with water (100 ml×3) and brine (50 ml), dried over $MgSO_4$, filtered and concentrated. To the light-yellow solid was then added 30 ml of 20% trifluoroacetic acid in $CH_2Cl_2$. The solution was concentrated and dried in vacuo to give the desired product VII. LC/MS analysis indicated this product was 100% pure and it was used for the next reaction without further purification.

Step B.

To piperazine indole-3-glyoxylamide (1 eq) was added resin-bound 1-(3-dimethylaminopropyl)-3-ethylcarbodiimide (P-EDC) (7 eq) and carboxylic acid (RCOOH) (2 eq) in dichloroethane (DCE) or DMF (dimethylformamide) in cases where the carboxylic acids are not soluble in DCE. The reaction was shaken for 12 hr at room temperature. The product XLI was filtered and concentrated. Products with purity less than 70% were diluted in methanol and purified using a Shimadzu automated preparative HPLC System.

Preparation of Example 195 in Table 7

Step A

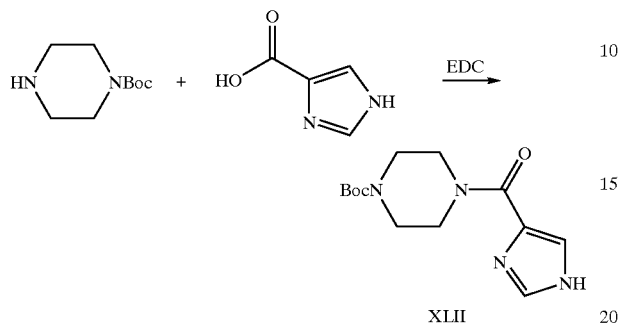

To a solution of tert-butyl-1-piperazine carboxylate (601 mg, 3.23 mmol) and 4-acetic acid imidazole (330 mg, 2.94 mmol) in dichloromethane (30 ml), were added DMAP (394 mg, 3.22 mmol) and EDC (616 mg, 3.22 mmol). The reaction mixture was stirred at room temperature for 21.5 hours. Removal of solvent in vacuo afforded a white solid, which was subjected to flash chromatography using a gradient elution (100% EtOAc, to 2% to 5% MeOH/EtOAc, to 1/5/95 NH$_3$(sat. aq.)/MeOH/EtOAc) to give XLII as a white solid.

Step B

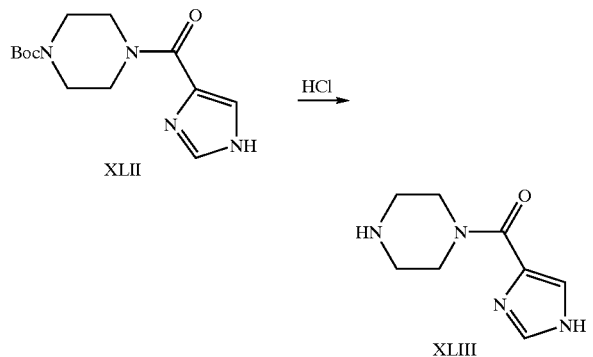

To compound XXLII (130 mg, 0.464 mmol) was added a solution of HCl in dioxane (4 M, 5 ml), and the mixture stirred at room temperature for 3 hours. Removal of the excess reagent in vacuo afforded the hydrochloride salt XLIII as a white solid (100% conversion).

Step C

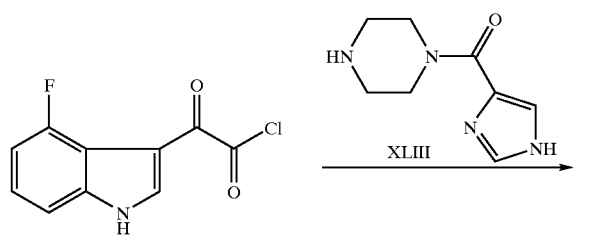

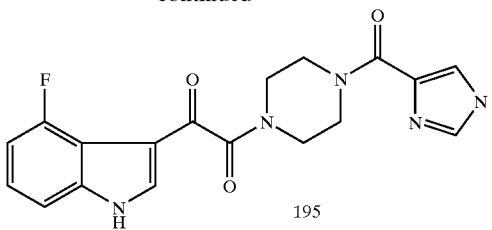

4-Fluoroindole glyoxyl chloride was coupled with XLIII as described previously.

TABLE 7

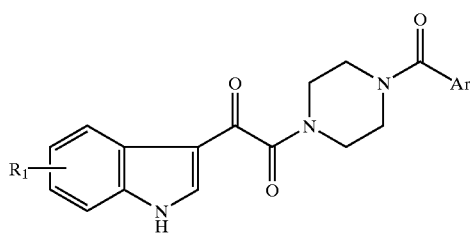

| Entry | R | Ar | HPLC Retention Time (min) | MS Data (M+H)+ |
|---|---|---|---|---|
| 148 | 4-Fluoro | 3-Thiophenyl | 1.74 | 386 |
| 149 | 4-Fluoro | 1,2,3-Thiadiazolyl | 1.52 | 388 |
| 150 | 4-Fluoro | 2-(4-Methoxy)-thiophenyl | 1.78 | 416 |
| 151 | 4-Fluoro | 2-(5-Methylthio)-thiophenyl | 2.28 | 432 |
| 152 | 4-Fluoro | 2-(3-Bromo)-thiophenyl | 2.22 | 465 |
| 153 | 4-Fluoro | 2-(5-Bromo)-thiophenyl | 2.29 | 465 |
| 154 | 4-Fluoro | 2-Pyrazinyl | 1.76 | 382 |
| 155 | 4-Fluoro | 2-(5-Methyl)-thiophenyl | 2.24 | 400 |
| 156 | 4-Fluoro | 2-(5-Chloro)-thiophenyl | 2.08 | 421 |
| 157 | 4-Fluoro | 2-Indolyl | 2.07 | 419 |
| 158 | 4-Fluoro | 4-(2-Methyl)-thiazolyl | 2.00 | 401 |
| 159 | 4-Fluoro | 4-Thiazolyl | 1.05 | 387 |
| 160 | 4-Fluoro | 4-Pyridyl | 0.84 | 381 |
| 161 | 4-Fluoro | 3-(6-Methyl)-pyridyl | 0.87 | 395 |
| 162 | 4-Fluoro | 3-Pyridyl | 0.93 | 381 |
| 163 | 4-Fluoro | 5-Isoxazolyl | 1.08 | 371 |
| 164 | 4-Fluoro | 2-Furanyl | 1.17 | 370 |
| 165 | 4-Fluoro | 3-Pyrazolyl | 1.03 | 370 |
| 166 | 4-Fluoro | 2-Pyridyl | 1.08 | 381 |
| 167 | 4-Fluoro | 3-Furanyl | 1.14 | 370 |
| 168 | 4-Fluoro | 2-Thiophenyl | 1.24 | 386 |
| 169 | 4-Fluoro | 2-Benzofuranyl | 1.48 | 420 |
| 170 | 4-Fluoro | 2-(5-Bromo)-furanyl | 1.37 | 449 |
| 171 | 4-Fluoro | 2-(3-Methyl)-furanyl | 1.30 | 384 |
| 172 | 4-Fluoro | 2-(3-Chloro)-thiophenyl | 1.34 | 420 |
| 173 | 4-Fluoro | 3-(5-Chloro-4-methoxy)-thiophenyl | 1.45 | 451 |
| 174 | 4-Fluoro | 2-(5-Chloro)-furanyl | 1.32 | 404 |
| 175 | 4-Chloro | 3-Thiophenyl | 2.02 | 403 |
| 176 | 4-Chloro | 2-[5-(Pyrid-2-yl)]-thiophenyl | 2.07 | 480 |
| 177 | 4-Chloro | 2-Thieno[3,2-B]-thiophenyl | 2.33 | 459 |
| 178 | 4-Chloro | 2-(5-Methylthio)-thiophenyl | 2.33 | 449 |
| 179 | 4-Chloro | 2-(5-Bromo)- | 2.34 | 481 |

TABLE 7-continued

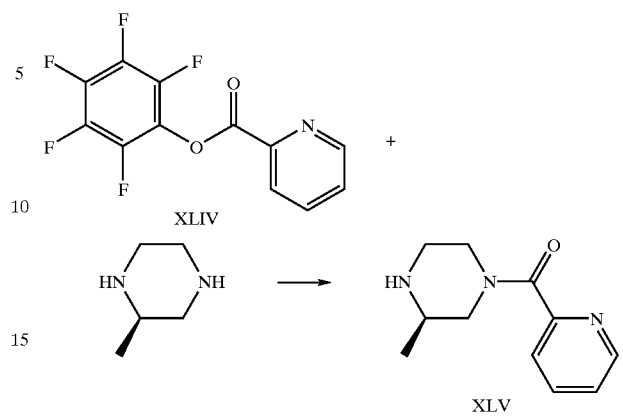

| Entry | R | Ar | HFLC Retention Time (min) | MS Data (M+H)+ |
|---|---|---|---|---|
| 180 | 4-Chloro | 2-Pyrazinyl | 1.91 | 398 |
| 181 | 4-Chloro | 2-Pyridyl | 1.92 | 397 |
| 182 | 4-Chloro | 2-Benzothiophenyl | 2.36 | 453 |
| 183 | 4-Chloro | 2-(5-Chloro)-thiophenyl | 2.33 | 437 |
| 184 | 4-Chloro | 2-(3-Chloro)-thiophenyl | 2.27 | 437 |
| 185 | 4-Chloro | 2-Indolyl | 2.33 | 436 |
| 186 | 4-Chloro | 4-(2-Methyl)-thiazolyl | 2.22 | 418 |
| 187 | 4-Chloro | 4-Thiazolyl | 1.20 | 404 |
| 188 | 4,7-Difluoro | 2-(5-Chloro)-furanyl | 1.39 | 422 |
| 189 | 4,7-Difluoro | 2-(5-Bromo)-furanyl | 1.46 | 467 |
| 190 | 4,7-Difluoro | 2-furanyl | 1.28 | 388 |
| 191 | 4,7-Difluoro | 2-Pyridyl | 1.17 | 399 |
| 192 | 4,7-Difluoro | 2-(3,4-Dichloro)-furanyl | 1.47 | 457 |
| 193 | 4,7-Difluoro | 2-(5-Trifluoromethyl)-furanyl | 1.54 | 456 |
| 194 | 4,7-Difluoro | 2-(4,5-Dimethyl)-furanyl | 1.49 | 416 |
| 195 | 4-Fluoro | 2-Imidazolyl | 0.81 | 370 |

Synthesis of Examples 195–215 in Table 8

Step A

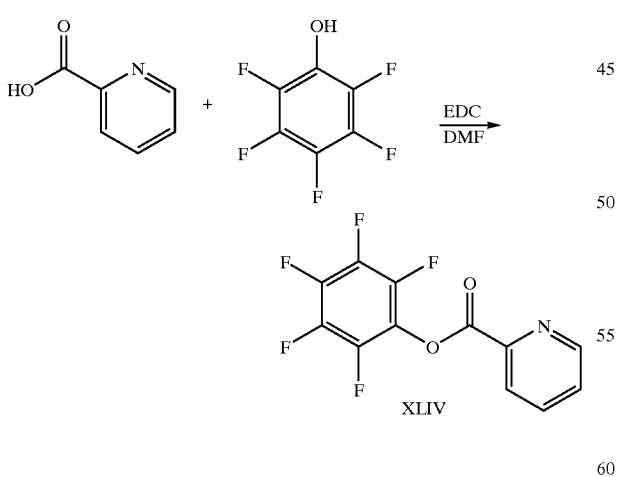

To pentafluorophenol (1.84 g, 10 mmol) in DMF (15 mL) was added picolinic acid (1.23 g, 10 mmol) and EDC (1.91 g, 10 mmol) at room temperature for 4 h. The crude product XLIV was diluted with CH$_2$Cl$_2$ and was washed with water, 0.1 M HCl and brine. The organic phase was dried over MgSO4, filtered and concentrated. The crude material was used without further purification.

Step B

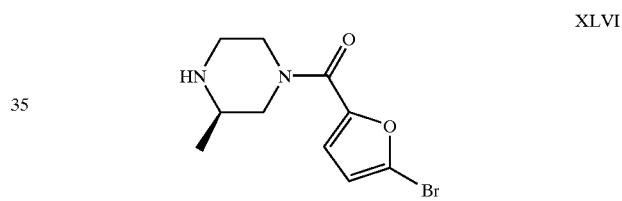

To a solution of (R)-methyl pierazine (1.0 g, 10 mmol) in DMF (20 mL) at room temperature was slowly added a solution of picolinic acid pentafluorophenylester XLIV in DMF (20 mL). The reaction mixture was stirred at room temperature for 16 h. The product was diluted with CH2Cl2 and was washed with water and brine, dried over MgSO4, filtered and concentrated. The product XLV was then purified by flash chromatography (100% EtOAc—50% MeOH/EtOAc).

Piperazine XLVI was prepared using similar methodology to that outlined in Step A and Step B above.

Step C

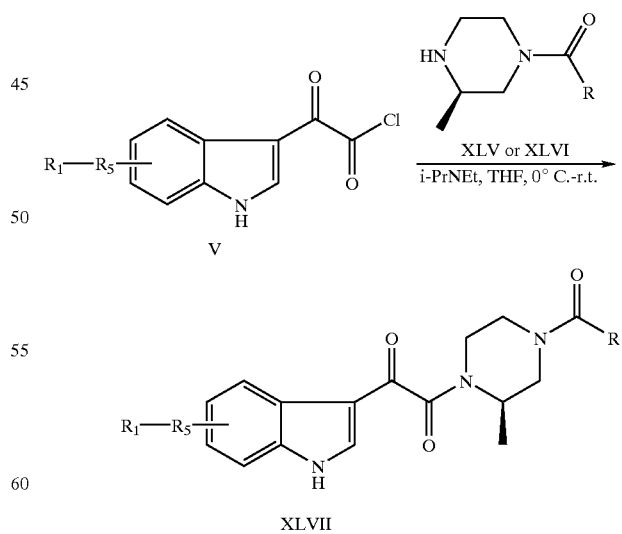

To the mixture of indole glyoxylchloride V (1 eq) and 3-(R)-methyl-1-piperazinecarboxylate XLV or XLVI (1 eq) in THF was added diisopropylethylamine (1.5 eq) dropwise at 0° C. The solution was stirred for additional 2 hr at room temperature and the resulting crude compounds were purified by preparative HPLC.

TABLE 8

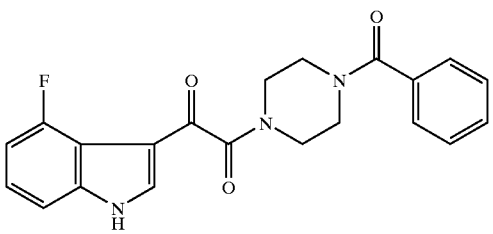

| Entry | R | Ar | HPLC Retention Time (min) | MS Data (M+H)+ |
|---|---|---|---|---|
| 196 | 4,7-difluoro | 2-Pyridyl | 1.23 | 413 |
| 197 | 4-Fluoro-7-methyl | 2-Pyridyl | 1.17 | 409 |
| 198 | 4,7-Difluoro | 2-(5-Bromo)-furanyl | 1.52 | 481 |
| 199 | 4,7-Dimethoxy | 2-(5-Bromo)-furanyl | 1.45 | 506 |
| 200 | 7-COOMe | 2-(5-Bromo)-furanyl | 1.70 | 504 |
| 201 | 4,7-Difluoro | 2-Pyridyl | 1.23 | 413 |
| 202 | 4-Fluoro | 2-Pyridyl | 1.07 | 395 |
| 203 | 4-Chloro | 2-Pyridyl | 1.22 | 411 |
| 204 | 4-Bromo | 2-Pyridyl | 1.25 | 457 |
| 205 | 5-Fluoro | 2-Pyridyl | 1.21 | 395 |
| 206 | 6-Chloro | 2-Pyridyl | 1.43 | 411 |
| 207 | 7-Fluoro | 2-Pyridyl | 1.29 | 395 |
| 208 | 7-Methoxy | 2-Pyridyl | 1.26 | 407 |
| 209 | 7-Methyl | 2-Pyridyl | 1.31 | 391 |
| 210 | 7-Ethyl | 2-Pyridyl | 1.46 | 403* |
| 211 | 4-methoxy-7-chloro | 2-Pyridyl | 1.22 | 441 |
| 212 | 7-cyano | 2-Pyridyl | 1.24 | 402 |
| 213 | 4-Methoxy | 2-Pyridyl | 1.09 | 407 |
| 214 | 4-Methoxy-7-Bromo | 2-Pyridyl | 1.28 | 487 |
| 215 | 4-Fluoro-7-Methoxy | 2-Pyridyl | 1.16 | 425 |

*(M-H) measured in negative ionization mode

Additional Analytical Data for Selected Compounds 1-(4-Methylbenzoyl)-4-[(1H-indol-3-yl)oxoacetyl]piperazine (Example 15)

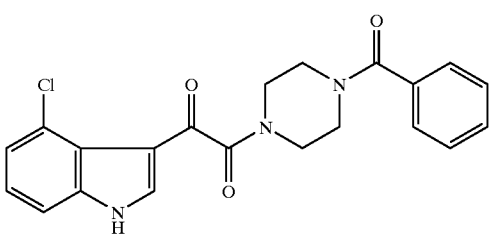

MS (ESI): 376 (M+H)+; IR (KBr): 3150, 3104, 2922, 2868, 1780, 1629, 1519, 1433, 1272, 1158, 1006, 829, 775, 753, 645 cm$^{-1}$; $^1$H NMR (CDCl$_3$) δ 2.40 (s, 3H), 3.60–3.79 (m, 8H), 7.23–7.45 (m, 7H), 7.99 (d, J=3.1 Hz, 1H), 8.34 (m, 1H), 9.10 (s, 1H).

1-(Benzoyl)-4-[(1H-4-fluoroindol-3-yl)oxoacetyl]piperazine (Example 19)

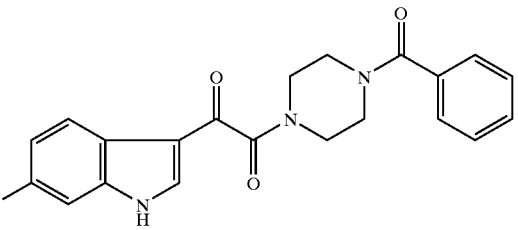

MS (ESI): 380 (M+H)+ HRMS calcd for C$_{21}$H$_{18}$FN$_3$O$_3$ [(M+H)]+, 380.14105; found, 380.1412. $^1$H-NMR (DMF-d7) δ 12.71(s, 1H), 8.02 (s, 1H), 7.46–7.56 (m, 6H), 7.31 (ddd, J=4.71, 7.99 Hz, 1H), 7.03 (dd, J=7.84, 10.98 Hz, 1H), 3.77 (br. s, 4H), 3.57 (br. s, 4H).

1-(Benzoyl)-4-[(1H-4-chloroindol-3-yl)oxoacetyl]piperazine (Example 20)

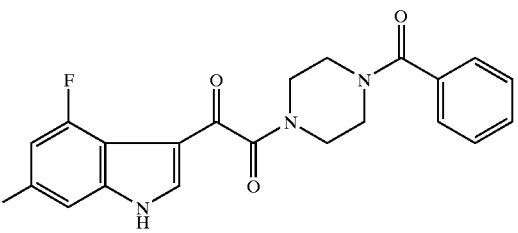

MS (ESI): 396 (M+H)+ HRMS calcd for C$_{21}$H$_{18}$ClN$_3$O$_3$ [(M+H)]+, 396.11150; found, 396.1105. 1H NMR (DMF-d7) δ 12.74 (br. s, 1H), 8.03 (s,1H), 7.57–7.65 (m, 1H), 7.50 (s, 5H), 7.28–7.38 (m, 1H), 3.42–3.83 (m, 8H).

1-(Benzoyl)-4-[(1H-6-fluoroindol-3-yl)oxoacetyl]piperazine (Example 28)

MS (ESI): 380 (M+H)+ HRMS calcd for C$_{21}$H$_{18}$FN$_3$O$_3$ [(M+H)]+, 380.14105; found, 380.1414. 1H NMR (DMF-d7) δ 12.09 (s, 1H), 7.81 (dd, J=5.64, 8.46 Hz, 1H), 7.62(s, 1H), 7.08 (s, 5H), 7.01 (dd, J=2.28, 9.61 Hz, 1H), 2.86–3.52 (m, 8H). Anal. Calcd for C$_{21}$H$_{18}$FN$_3$O$_3$: C, 66.48; H, 4.78, N, 11.08. Found: C, 66.09, H, 4.78, N, 10.94.

1-(Benzoyl)-4[(1H-4,6-difluoroindol-3-yl)oxoacetyl]piperazine (Example 42)

$^1$H NMR (DMSO-d$_6$) δ 3.40 (br s, 4H), 3.65 (br s, 4H), 7.06 (t, 1H), 7.20 (d, J=8.49 Hz, 1H), 8.27 (s, 1H), 12.65 (br s, 1 H). Anal. Calcd for $C_{21}H_{17}F_2N_3.O_30.322$ $H_2O$: C, 62.57; H, 4.41; N, 10.42; Found: C, 62.56; H, 4.46; N, 10.11.

1-(benzoyl)-4-[(1H-5-fluoro-7-bromoindol-3-yl)oxoacetyl] piperazine (Example 48)

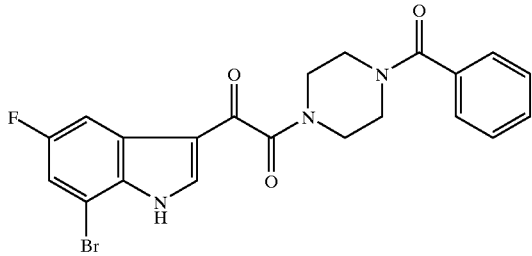

$^1$H NMR (DMSO-d$_6$) δ 3.40 (br s, 4H), 3.67 (br s, 4H), 7.43 (br s, 5H), 7.54 (dd, J=2.25, 8.97 Hz, 1H), 7.83 (d, J=8.4 Hz, 1H), 8.29 (s, 1H), 12.79 (br s, 1 H). Anal. Calcd for $C_{21}H_{17}N_3BrF_3.1.2$ $H_2O$: C, 52.56; H, 4.07; N, 8.76. Found: C, 52.33; H, 3.69; N, 8.50.

1-(benzoyl)-4-[(1H-4-fluoro-7-trifluoroethoxyindol-3-yl) oxoacetyl]piperazine (Example 51)

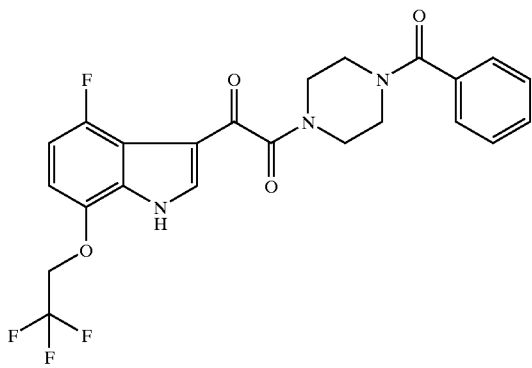

$^1$H NMR (DMSO-d$_6$) δ 3.61 (br m, 4H), 3.80 (br m, 4H), 4.52 (m, 2H), 6.68 (m, 1H), 6.91 (m, 1H), 7.45 (s, 5H), 8.07 (d, J=2.91 Hz, 1H), 9.37 (s 1H). Anal. Calcd for $C_{23}H_{19}F_4N_3O_4.0.59$ $H_2O$, 0.47 ethyl acetate C, 56.44; H, 4.56; N,=7.94; Found: C, 56.44; H, 4.16; N,=8.19.

1-(Benzoyl)-4-[(1H-4-bromo-7-fluoroindol-3-yl)oxoacetyl] piperazine (Example 55)

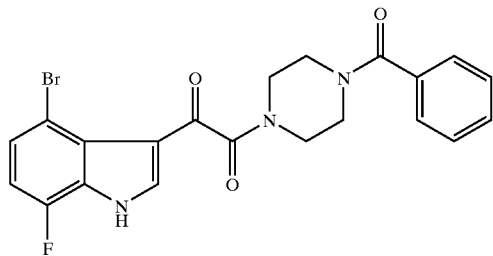

$^1$H NMR (CDCl$_3$) δ 3.6–3.9 (br m, 8H), 6.92 (t, 1H), 7.42 (br s, 6H), 8.09 (s, 1H), 9.5 (br s, 1 H). Anal. Calcd for $C_{21}H_{17}BrFN_3O_3.0.25$ $H_2O$, 0.21 ethyl acetate: C, 54.5; H, 4.02; N, 16.6; Found: C, 54.50; H, 4.09; N, 8.44. Example 90

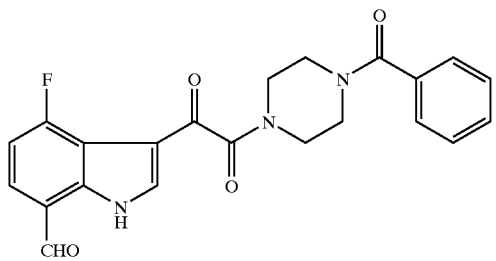

$^1$H NMR: (DMSO-d$_6$) δ 3.66 (br. s, 4H), 7.27 (t, J=8.31 Hz, 1H), 7.43 (br. s, 7H), 8.01 (m, 1H), 8.14 (s, 1H), 10.14 (s, 1H), 12.42 (br. s, 1H) MS: (M+H)$^+$ 480.00, (M–H) 406.02; IR: 1636,1592 cm$^{-1}$.

N-(Benzoyl)-(R)-3-methyl-N'-[(4-fluoro-indol-3-yl)-oxoacetyl]-piperazine (Example 93)

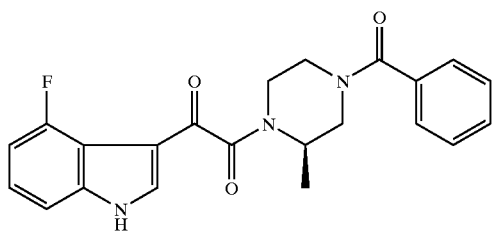

$^1$H NMR (300 MHz, CD$_3$OD) δ 8.20 (s, 0.5H), 8.15 (s, 0.5H), 7.48–6.90 (m, 8H), 5.00–3.00 (m, 7H), 1.30 (b, 3H). MS m/z: (M+H)$^+$ calcd for $C_{22}H_{21}FN_3O_3$: 394.16; found 394.23. HPLC retention time: 0.92 minutes (Method B).

N-(Benzoyl)-(S)-3-methyl-N'-[(fluoro-indol-3-yl)-oxoacetyl]-piperazine (Example 94)

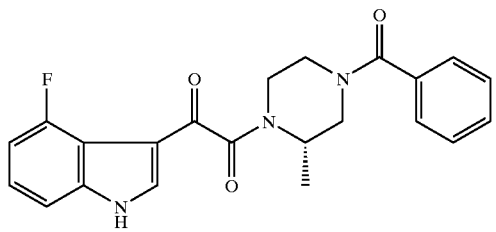

$^1$H NMR (300 MHz, CD$_3$OD) δ 8.20 (s, 0.5H), 8.13 (s, 0.5H), 7.48–6.90 (m, 8H), 5.00–3.00 (m, 7H), 1.30 (b, 3H). MS m/z: (M+H)$^+$ calcd for $C_{22}H_{21}FN_3O_3$: 394.16; found 394.25. HPLC retention time: 1.32 minutes (Method A).

N-(Benzoyl)-2-methyl-N'-[(4-fluoro-indol-3-yl)-oxoacetyl]-piperazine (Example 95)

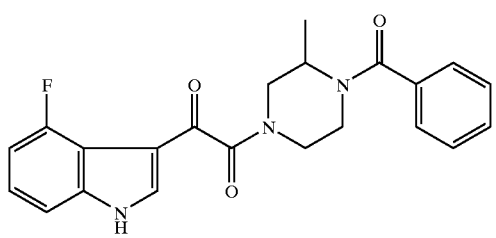

$^1$H NMR (300 MHz, CD$_3$OD) δ 8.20 (s, 0.5H), 8.13 (s, 0.5H), 7.48–6.90 (m, 8H), 5.00–3.00 (m, 7H), 1.37 (d, J=6.78 Hz, 1.5H), 1.27 (d, J=6.84 Hz, 1.5H). MS m/z: (M+H)$^+$ calcd for $C_{22}H_{21}FN_3O_3$: 394.16; found 394.23. HPLC retention time: 1.32 minutes (Method A).

N-(Benzoyl)-3-hydroxylmethyl-N'-[(4-fluoro-indol-3-yl)-oxoacetyl]-piperazine (Example 99)

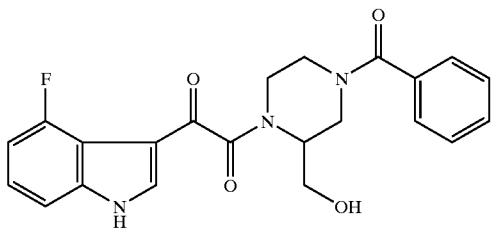

¹H NMR (300 MHz, CD₃OD) δ 7.50 (b, 5H), 7.39–6.72 (m, 4H), 5.00–2.80 (m, 9H). MS m/z: (M+Na)⁺ calcd for C₂₂H₂₀FN₃NaO₄: 432.13; found 432.19. HPLC retention time: 1.23 minutes (Method A).

N-(benzoyl)-(R)-3-methyl-N'-[(7-methoxycarbonyl-indol-3-yl)-oxoacetyl]-piperazine (Example 102)

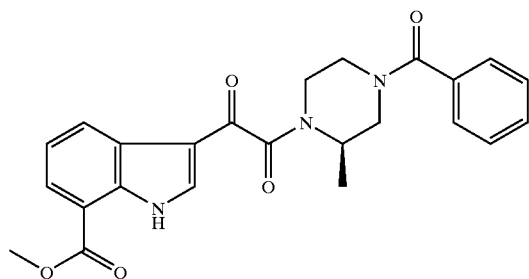

1H NMR (300 MHz, CD₃OD) 8.50 (d, J=6.48 Hz, 1H), 8.15 (s, 0.5H), 8.10 (s, 0.5H), 8.00 (d, J=7.38 Hz, 1H), 7.42 (m, 6H), 5.00–3.00 (m, 7H), 4.02 (s, 3H), 1,34 (b, 3H); ¹³C NMR (75 MHz, CD₃OD); δ 186.2, 166.9, 137.9, 135.3, 130.3, 128.8, 127.2, 126.9, 126.4, 122.7, 114.5, 114.0, 51.6, 50.7, 45.6, 15.4, 14.2. MS m/z: (M+H)⁺ calcd for C₂₄H₂₄N₃O₅: 434.17; found 434.24. HPLC retention time: 1.41 minutes (Method B).

N-(Benzoyl)-3-hydroxylmethyl-N'-[(7-methoxycarbonyl-indol-3-yl)-oxoacetyl]-piperazine (Example 98)

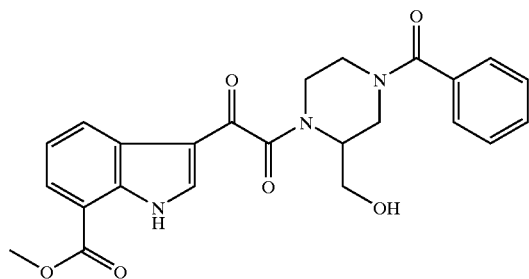

¹H NMR (300 MHz, CD₃OD) δ 8.54 (b, 1H), 8.24 (s, 0.5H), 8.16 (s, 0.5H), 8.00 (m, 1H), 7.47 (m, 6H), 5.00–3.00 (m, 9H), 4.02 (s, 3H). MS m/z: (M+H)⁺ calcd for C₂₄H₂₄N₃O₆: 450.17; found 450.24. HPLC retention time: 1.44 minutes (Method A).

N-(Benzoyl)-2-methoxycarbonyl-N'-[(7-methoxycarbonyl-indol-3-yl)-oxoacetyl]-tetrahydropyrazine (Example 121)

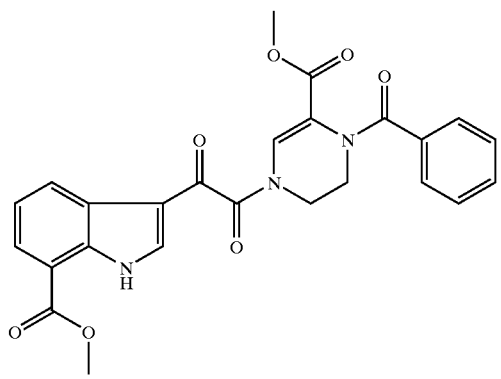

¹H NMR (500 MHz, CD₃OD) δ 8.50 (m, 1H), 8.21 (s, 1H), 7.93 (m, 1H), 7.44 (m, 7H), 4.00 (s, 6H), 4.00–3.30 (m, 4H); ¹³C NMR (125 MHz, CD₃OD) δ 184.7, 167.9, 166.1, 165.3, 165.1, 164.9, 140.2, 137.2, 132.5, 129.6, 128.3, 128.2, 127.6, 125.1, 123.9, 116.0, 115.6, 115.0, 52.8, 52.6, 47.0, 43.8. MS m/z: (M+H)⁺ calcd for C₂₅H₂₂N₃O₇: 476.15; found 476.21. HPLC retention time: 1.62 minutes (Method A).

N-(Benzoyl)-2-propyl-N'-[(7-methoxycarbonyl-indol-3-yl)-oxoacetyl]-piperazine (Example 126)

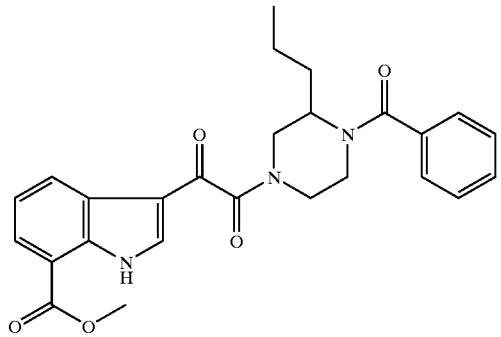

¹H NMR (300 MHz, CD₃OD) δ 8.50 (d, J=6.93 Hz, 1H), 8.17 (s, 0.5H), 8.08 (s, 0.5H), 7.98 (d, J=6.00 Hz, 1H), 7.45 (m, 6H), 5.00–2.90 (m, 7H), 4.02 (s, 3H), 1.70–0.60 (m, 7H); ¹³C NMR (75 MHz, CD₃OD) 5186.0, 167.6, 166.9, 138.0, 136.1, 135.8, 130.2, 128.9, 127.2, 126.9, 126.4, 122.7, 114.5, 114.1, 51.7, 46.2, 44.0, 41.3, 31.5, 19.2, 13.2, 12.9. MS m/z: (M+H)⁺ calcd for C₂₆H₂₈N₃O₅: 462.20; found 462.30. HPLC retention time: 1.69 minutes (Method A).

N-(Benzoyl)-(R)-3-methyl-N'-[(7-hydroxycarbonyl-indol-3-yl)-oxoacetyl]-piperazine (Example 137)

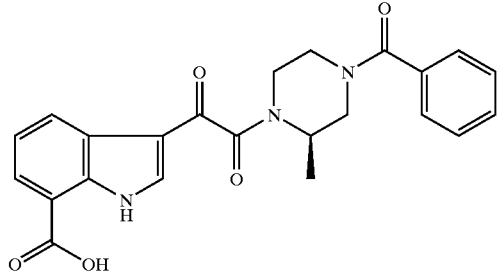

¹H NMR (300 MHz, CD₃OD) δ 8.46 (b, 1H), 8.14 (s, 0.5H), 8.09 (s, 0.5H), 8.00 (d, J=7.17 Hz, 1H), 7.43 (m, 6H), 5.00–2.90 (m, 7H), 1.32 (b, 3H); $^{13}$C NMR (75 MHz, CD$_3$OD) δ 186.3, 168.2, 167.1, 137.8, 135.3, 130.3, 128.8, 127.1, 126.9, 126.7, 122.7, 115.4, 113.9, 50.7, 45.6, 15.4, 14.2. MS m/z: (M+H)$^+$ calcd for C$_{27}$H$_{30}$N$_3$O$_5$: 420.16; found 420.16. HPLC retention time: 1.43 minutes (Method A).

N-(Benzoyl)-3-trifluoromethyl-N'-[(7-methoxycarbonyl-indol-3-yl)-oxoacetyl]-piperazine (Example 142)

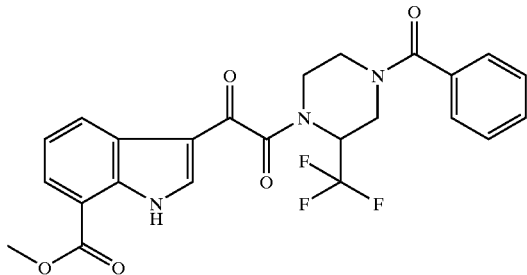

$^1$H NMR (300 MHz, CD$_3$OD) δ 8.52 (b, 1H), 8.03 (s, 1H), 8.02 (d, J=7.56 Hz, 1H), 7.45 (m, 6H), 5.00–3.00 (m, 7H), 4.03 (s, 3H). MS m/z: (M+H)$^+$ calcd for C$_{24}$H$_{21}$F$_3$N$_3$O$_5$: 488.14; found 488.15. HPLC retention time: 1.65 minutes (Method A).

N-(Benzoyl)-3-trifluoromethyl-N'-[(4-fluoro-indol-3-yl)-oxoacetyl]-piperazine (Example 143)

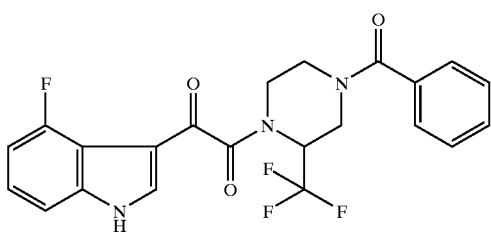

$^1$H NMR (300 MHz, CD$_3$OD) δ 8.11 (s, 1H), 7.50–6.90 (m, 9H), 5.00–3.00 (m, 7H). MS m/z: (M+H)$^+$ calcd for C$_{24}$H$_{21}$F$_3$N$_3$O$_5$: 488.14; found 488.12. HPLC retention time: 1.42 minutes (Method A).

N-(Benzoyl)-(R)-3-methyl-N'-[(4-fluoro-7-bromoindol-3-yl)-oxoacetyl]-piperazine (Example 144)

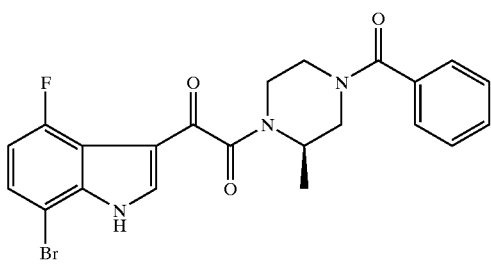

$^1$H NMR (CDCl$_3$) δ 1.31 (br. s, 3H), 3.34 (br. s, 4H), 3.59 (br. s, 3H), 6.90 (t, J=8.7 Hz, 1H), 7.38 (br. s, 6H), 8.05 (br. s, 1H), 9.46 (br. s, 1H); MS: (M+H)$^+$ 473.80, (M–H) 470.02; IR: 1634, 1579 cm$^{-1}$; Anal. calcd. for C22H19N3O3BrF. 0.6H2O C, 54.68; H, 4.21; N, 8.7. Found C, 54.46; H, 4.14; N, 8.56.

1-[(Pyrid-2-yl)oxo]-4-[(1H-4-fluoro-indol-3-yl)oxoacetyl] piperazine (Example 166)

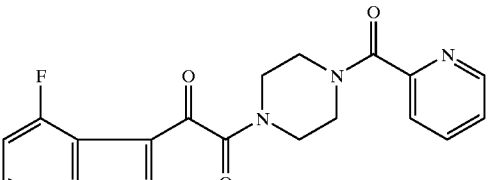

MS (ESI): 381 (M+H)$^+$; $^1$H NMR (CDCl$_3$) δ 3.56 (m, 2H), 3.66 (m, 2H), 3.82–3.94 (m, 4H), 6.97 (m, 1H), 7.33 (m, 2H), 7.57 (m, 1H), 7.70 (m, 1H), 8.01 (m, 1H), 8.20 (s, 1H), 8.66 (m, 1H).

1-[(Pyrid-2-yl)oxo]-4-[(1H-4,7-difluoro-indol-3-yl) oxoacetyl]piperazine (Example 191)

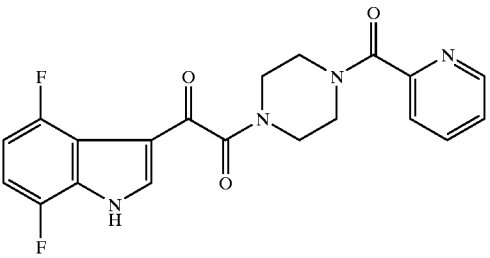

MS (ESI): 413 (M+H)$^+$; $^1$H NMR (CDCl$_3$) δ 3.54–3.65 (m, 4H), 3.76–3.93 (m, 4H), 6.95 (m, 2H), 7.52 (m, 1H), 7.66 (m, 1H), 7.96 (m, 1H), 8.20 (m, 1H), 8.60 (m, 1H). Example 195

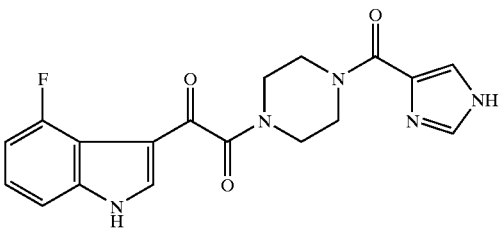

MS (ESI): 370 (M+H)$^{+1}$H NMR: (CD$_3$OD, δ=3.30 ppm) 8.82 (s, 1H), 8.21 (s,1H), 8.00 (s, 1H), 7.37–7.26 (m, 2H), 7.02–6.96 (m, 1H), 3.97(b s, 2H), 3.86 (app dd, J=6.4, 3.3, 4H), 3.64 (app dd, J=6.3, 4.0, 2H); LC/MS: (ES+) m/z (M+H)$^+$=370, Analytical HPLC (R$_t$=0.810 min) purity: 100%. Example 212

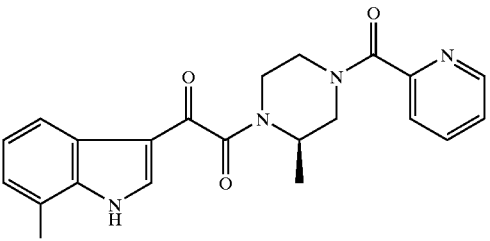

MS (ESI): 402 (M+H)$^{+1}$H NMR: (CD$_3$OD, δ=3.30 ppm) 8.65–8.51 (m, 2H), 8.24–8.19 (m, 1H), 8.02–7.94 (m, 1H), 7.73–7.68 (m, 2H), 7.56–7.39 (m, 2H), 4.63–3.09 (b m, 7H), 1.35 (m, 3H).

Procedures for making compounds of formula I are shown in Schemes 14–22, and further exemplified in Tables 14–18.

Scheme 14

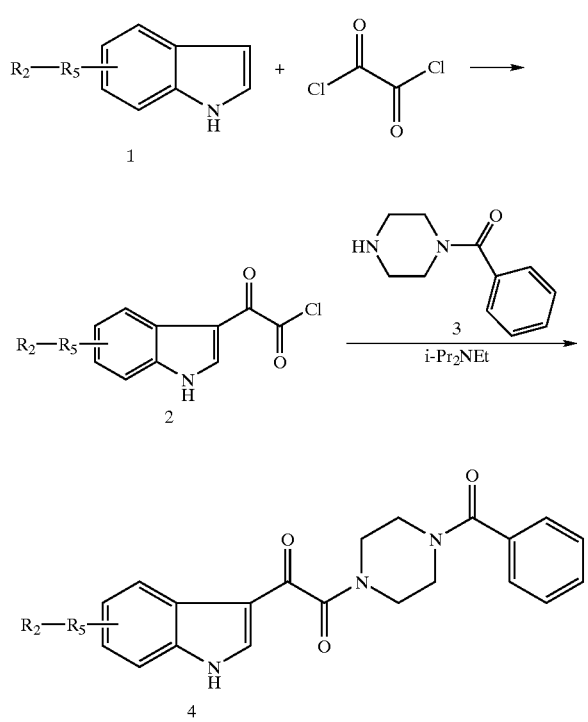

Starting indoles 1 (Scheme 14) are known or are readily prepared according to literature procedures, such as those described in Gribble, G. (Ref. 24) or Bartoli et al (Ref. 36). The indoles 1 are treated with oxalyl chloride in either THF (tetrahydrofuran) or ether to afford the desired glyoxyl chlorides 2 according to literature procedures (Lingens, F. et al, Ref. 25). The intermediate glyoxyl chlorides 2 are then coupled with benzoyl piperazine 3 (Desai, M. et al, Ref. 26) under basic conditions to afford 4.

Scheme 15

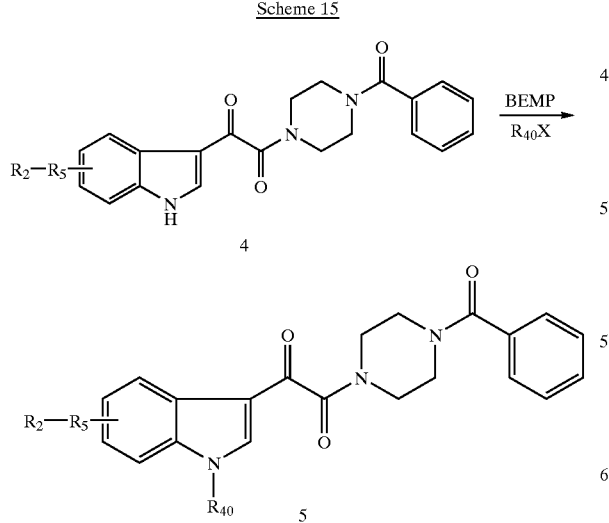

Treatment of indole glyoxamide 4 (Scheme 15) with an alkylating agent ($R_{40}X$) under basic conditions (BEMP or NaH) affords N-alkylated derivatives 5.

Scheme 16

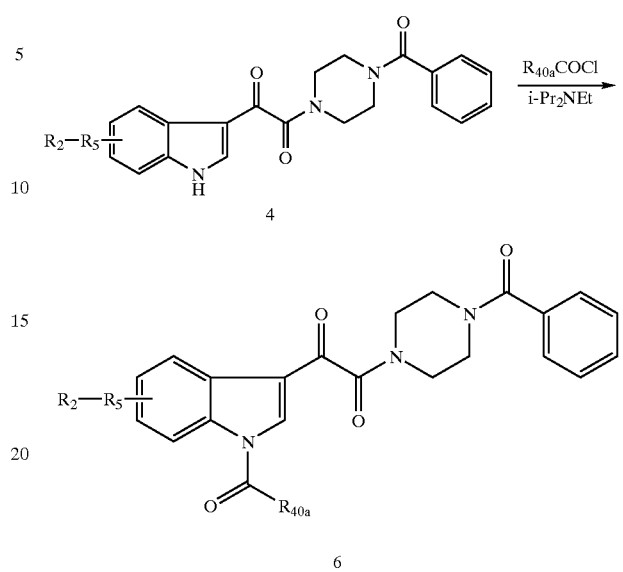

N-acyl derivatives 6 are prepared by treatment of indole gyloxamide 4 with an acid chloride ($R_{40a}COCl$) in the presence of i-$Pr_2NEt$ (Scheme 16). Alternatively, bis-acylated products are prepared as shown in Scheme 17.

Scheme 17

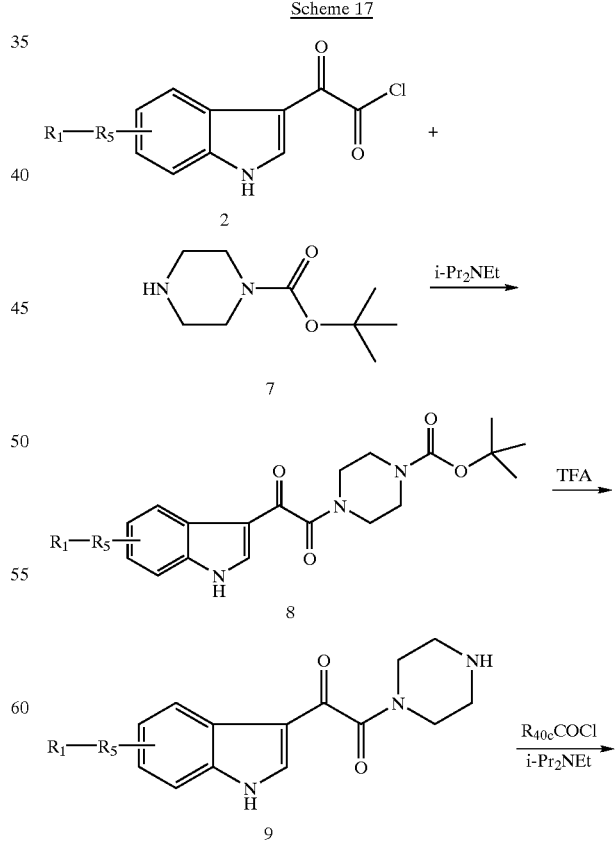

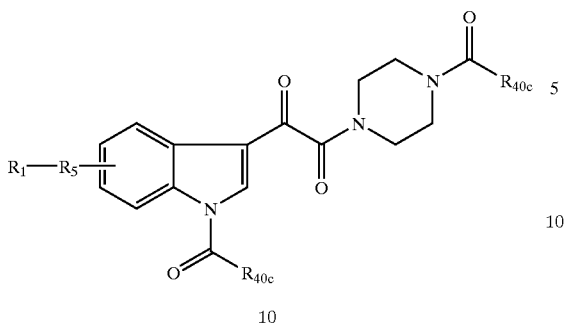

10

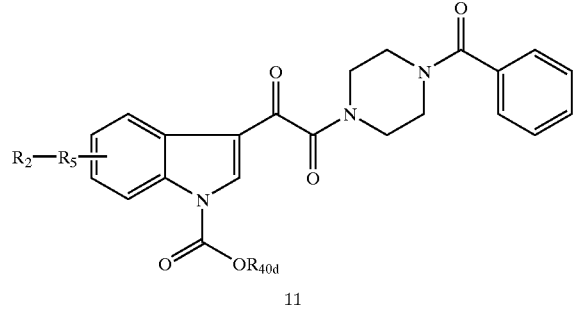

11

Carbamates 11 are synthesised by reaction of indole glyoxamide 4 with chloroformate ($R_{40d}OCOCl$) in the presence of i-Pr$_2$NEt or NaH (Scheme 18).

Treatment of indole-3-glyoxyl chloride 2 (Scheme 17) with tert-butyl 1-piperazinecarboxylate 7 affords the coupled product 8. Removal of the Boc protecting group of 8 is effected with 20% TFA/CH$_2$Cl$_2$ to yield 9. This product is then coupled with acid chloride ($R_{40c}COCl$) to afford bis-acyl products 10.

Scheme 19

Scheme 18

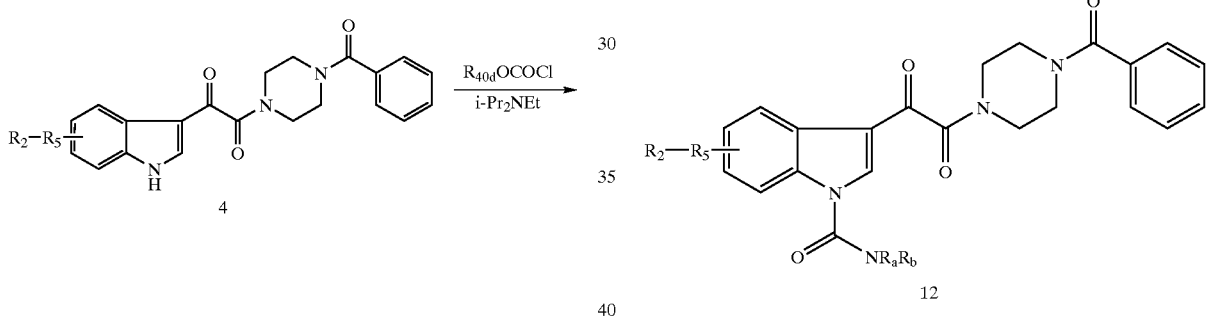

Ureas are prepared by three methods. Direct treatment of indole glyoxamide 4 with carbamoyl chloride ($R_aR_bNCOCl$) in the presence of i-Pr$_2$NEt affords the desired ureas 12 (Scheme 19).

Scheme 20

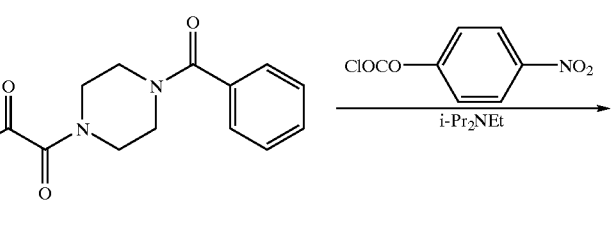

-continued

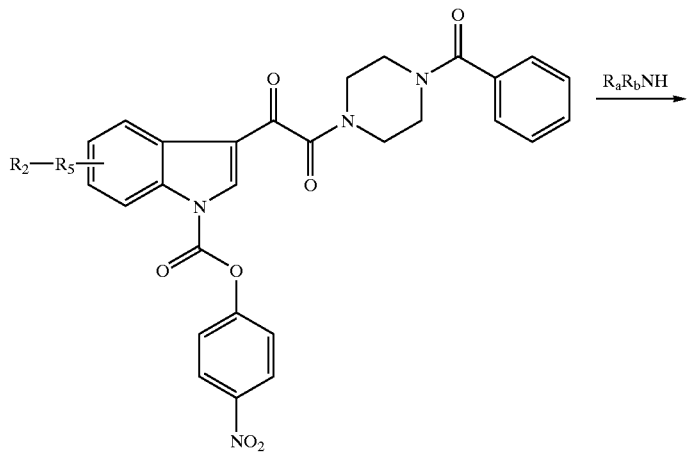

13

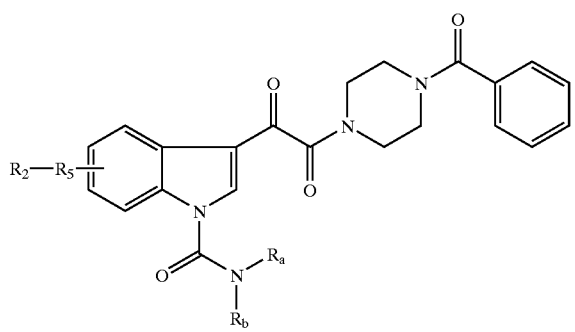

14

Alternatively, treatment of 4 (Scheme 20) with p-nitrophenylchloroformate and i-Pr$_2$NEt affords p-nitrophenylcarbamate 13 which, on exposure to amine (R$_a$R$_b$NH), affords the desired urea 14.

(Scheme 21).

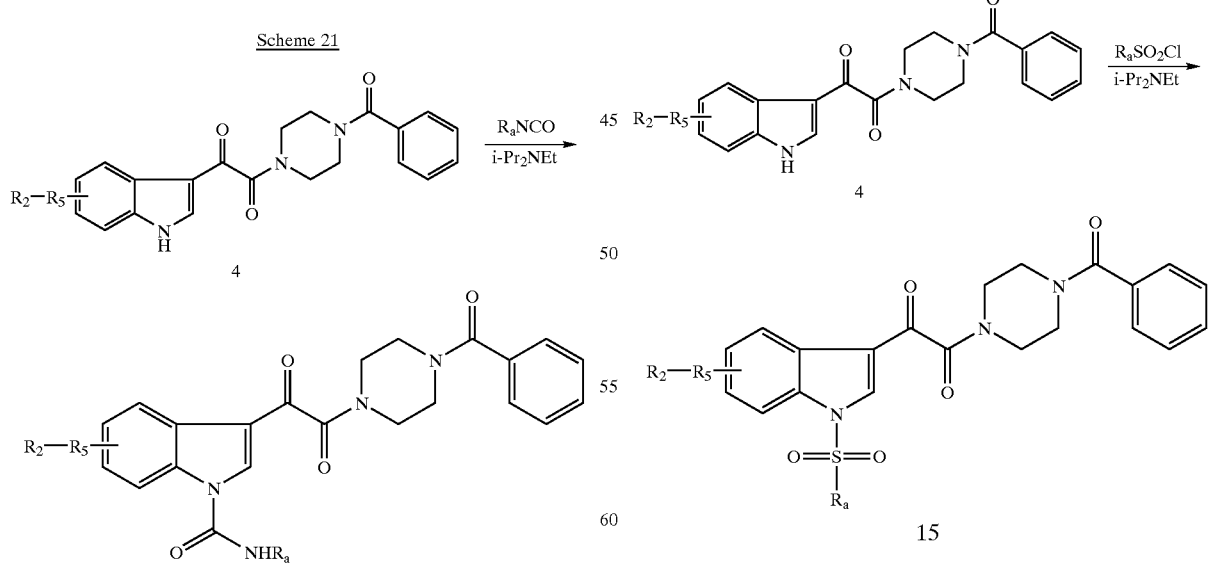

Finally, reaction of indole glyoxamide 4 with isocyanate (R$_a$NCO) in the presence of i-Pr$_2$NEt affords urea 15

Indole sulfonamides 15 (Scheme 22) are readily prepared by treatment of indole glyoxamide 4 with sulfonyl chloride (R$_a$SO$_2$Cl) in the presence of i-Pr$_2$NEt.

TABLE 9

[Structure: indole with R1 substituent and R40 on N, connected via C(O)-C(O) to piperazine-N-C(O)-phenyl]

| Example # | R₁ | R₄₀ | % Inhibition @ 10 μM |
|---|---|---|---|
| 1 | H | -CH₂-CH=CH₂ (allyl) | 65 |
| 2 | H | -CH₂-C≡CH (propargyl) | 98 |
| 3 | H | -CH₂-(3-CF₃-phenyl) | 71 |
| 4 | H | -CH₂-(4-methylphenyl) | 45 |
| 5 | H | -(CH₂)₃-O-phenyl | 83 |
| 6 | H | -CH₃ | 89 |
| 7 | H | -CH₂CH₂CH(CH₃)₂ | 60 |
| 8 | H | -CH₂-cyclohexyl | 89 |
| 9 | H | -CH₂-CH=C(CH₃)₂ | 82 |
| 10 | H | -CH₂CH₃ | 84 |

TABLE 9-continued

| Example # | R₁ | R₄₀ | % Inhibition @ 10 μM |
|---|---|---|---|
| 11 | H | -n-butyl | 84 |
| 12 | 2-Methyl | -CH₃ | 69 |
| 13 | 4-Fluoro | -CH₃ | >98 |
| 14 | 4-Chloro | -CH₃ | >98 |
| 15 | 6-Fluoro | -CH₃ | 97 |
| 16 | 4,7-Difluoro | -CH₂CH₂-N(CH₃)₂ | 71 |
| 17 | 4,7-Difluoro | -CH₂CH₂-C≡N | 97 |
| 18 | 4,7-Difluoro | -CH₂-C(O)-N(Et)₂ | 96 |
| 19 | 4,7-Difluoro | -CH₂CH₂-C(O)-OBu-t | 88 |
| 20 | 4,7-Difluoro | -CH₃ | >98 |

TABLE 9-continued

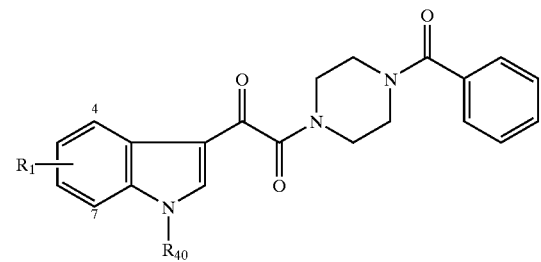

| Example # | R<sub>1</sub> | R<sub>40</sub> | % Inhibition @ 10 μM |
|---|---|---|---|
| 21 | 4,7-Difluoro | -CH2CH2C(O)OH | 93 |
| 22 | 4,7-Difluoro | -CH2C(=NOH)NH2 | 89 |
| 23 | 4,7-Difluoro | -CH2-(1,2,4-oxadiazol-5(4H)-one-3-yl) | 98 |
| 24 | 4-Fluoro | -CH2CH2N(CH3)2 | 91 |
| 25 | 4-Fluoro | -CH2CH2Cl | 92 |
| 26 | 4-Fluoro | -CH2CH2CH2CO2Et | 95 |
| 27 | 4-Fluoro | -CH(CH2CH2CH2CH2CO2Et)- | 98 |
| 28 | 4-Fluoro | -CH2CH2CO2Et | 96 |

TABLE 9-continued

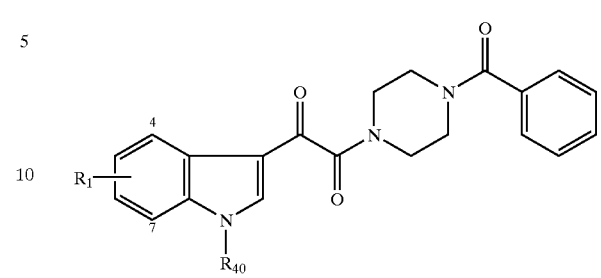

| Example # | R<sub>1</sub> | R<sub>40</sub> | % Inhibition @ 10 μM |
|---|---|---|---|
| 29 | 4-Fluoro | -CH2-(pyridin-2-yl) | 93 |
| 30 | 4-Fluoro | -CH2-(pyridin-3-yl) | 92 |
| 31 | 4-Fluoro | -CH2-(pyridin-4-yl) | 82 |
| 32 | 4-Fluoro | -CH2OC(O)C(CH3)3 | 97 |
| 33 | 4-Fluoro | -(4-CO2Et-phenyl) | 80 |
| 34 | 4-Fluoro | -(4-NO2-phenyl) | 88 |

TABLE 10

| Example # | R₁ | R₄₀ | R₅ | % Inhibition @ 10 μM |
|---|---|---|---|---|
| 35 | H | 2-F-benzoyl | 2-F-benzoyl | 95 |
| 36 | H | 2-Cl-benzoyl | 2-Cl-benzoyl | 55 |
| 37 | H | 2-Br-benzoyl | 2-Br-benzoyl | 50 |
| 38 | H | 2-MeO-benzoyl | 2-MeO-benzoyl | <10 |
| 39 | H | 3-F-benzoyl | 3-F-benzoyl | 81 |
| 40 | H | 3-Cl-benzoyl | 3-Cl-benzoyl | 82 |
| 41 | H | 3-Br-benzoyl | 3-Br-benzoyl | 86 |
| 42 | H | 3-OMe-benzoyl | 3-OMe-benzoyl | 35 |

TABLE 10-continued
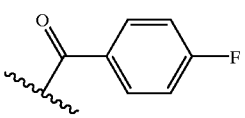
| Example # | R₁ | R₄₀ | R₅ | % Inhibition @ 10 μM |
|---|---|---|---|---|
| 43 | H | 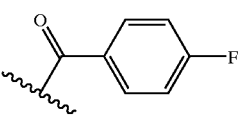 | 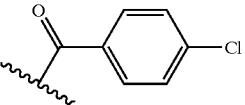 | 86 |
| 44 | H | 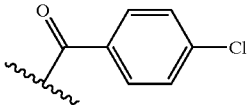 | 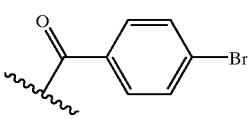 | 52 |
| 45 | H | 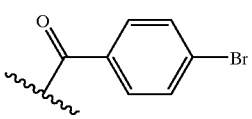 | 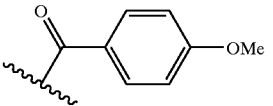 | 64 |
| 46 | H | 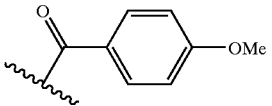 | 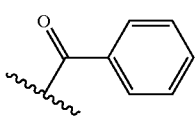 | 46 |
| 47 | H | 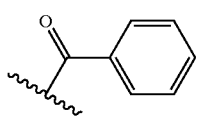 | 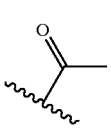 | >98 |
| 48 | H | 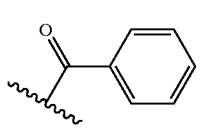 | 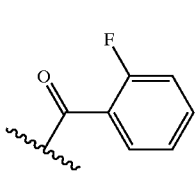 | 93 |
| 49 | H | 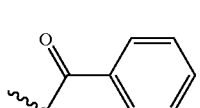 | 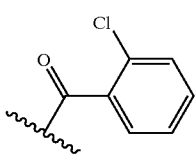 | 97 |
| 50 | H | 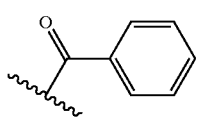 | 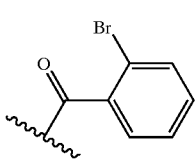 | 97 |
| 51 | H | 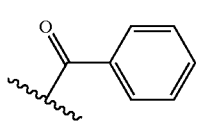 |  | 96 |

TABLE 10-continued
| Example # | R₁ | R₄₀ | R₅ | % Inhibition @ 10 μM |
|---|---|---|---|---|
| 52 | H | 2-MeO-benzoyl | benzoyl | 96 |
| 53 | H | 4-MeO-benzoyl | benzoyl | 96 |
| 54 | 4-Chloro | benzoyl | benzoyl | >98 |
| 55 | 4-Fluoro | benzoyl | benzoyl | >98 |
| 56 | 4-Fluoro | 4-MeO-benzoyl | benzoyl | >98 |
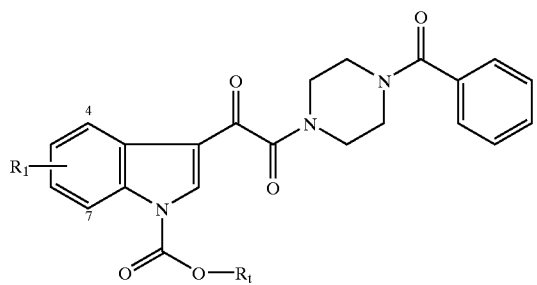
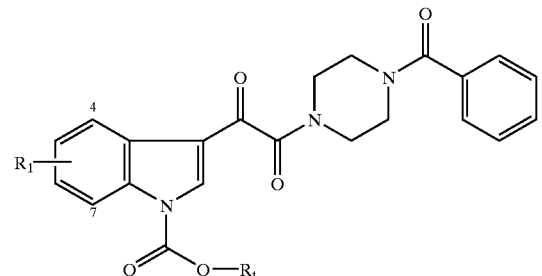
TABLE 11
| Example # | R₁ | R$_t$ | % Inhibition @ 10 μM |
|---|---|---|---|
| 57 | 4-Choro | Phenyl | >98 |
| 58 | H | Phenyl | 97 |
| 59 | 4-Fluoro | Phenyl | >98 |
| 60 | 4-Fluoro | Benzyl | >98 |
| 61 | 7-Methyl | t-Butyl | 96 |
| 62 | 4-Fluoro | Methyl | >98 |
| 63 | 4-Fluoro | Ethyl | >98 |
| 64 | 4-Fluoro | t-Butyl | >98 |

TABLE 12

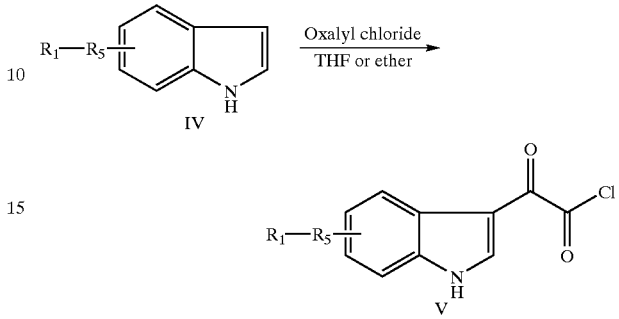

| Example # | $R_m$ | % Inhibition @ 10 uM |
|---|---|---|
| 65 | (N-methyl-N-phenyl) | 93 |
| 66 | (morpholino) | >98 |
| 67 | (N,N-dimethyl) | 97 |
| 68 | (4-methylpiperazinyl) | 97 |
| 69 | (N-ethyl-NH) | >98 |

TABLE 13

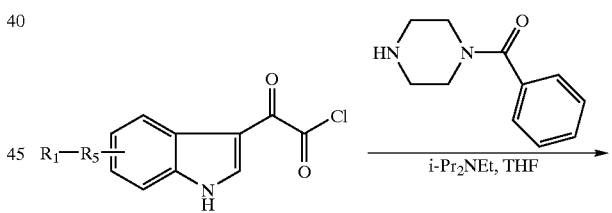

| Example # | $R_n$ | % Inhibition @ 10 uM |
|---|---|---|
| 70 | Phenyl | 90 |
| 71 | Methyl | 82 |

EXPERIMENTALS

3) General Procedure for Preparation of Examples 1–34

Step A.

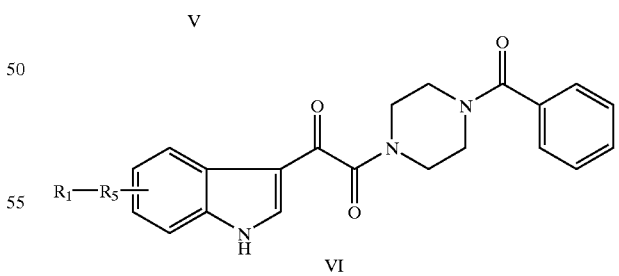

To a solution of substituted indole IV (1 eq) in dry $Et_2O$ was dropwise added oxalylchloride (1.2 eq) at 0° C. After 5 min., the reaction mixture was warmed to room temperature, or heated to ~35° C. overnight if necessary. The intermediate substituted-indole-3-glyoxyl chloride V, which was formed as a solid, was filtered and washed with dry ether (2×1 ml) to remove excessive oxalyl chloride. The product was then dried under vacuum to give desired glyoxyl chlorides V.

In cases where reaction in $Et_2O$ was unsuccessful, the following procedure was adopted: To a solution of substituted indole IV (1 eq) in dry THF (tetrahydrofuran) solvent was dropwise added oxalyl chloride (1.2 eq) at 0° C. After 5 min., the reaction was warmed to room temperature, or heated to ~70° C. under nitrogen if necessary. After concentration in vacuo, the resulting crude intermediate V was submitted to next step without further treatment.

Step B

To a solution of indole glyoxyl chloride V (1 eq) in dry THF was added benzoylpiperazine (1 eq) at room temperature. Then the mixture was cooled down to 0° C., followed by dropwise addition of diisopropylamine (1.3 eq). After 5 min., the reaction mixture was warmed to room temperature and was shaken for 3 hr. The resulting crude products VI were purified by preparative HPLC and characterized as shown in Table 14.

Step C

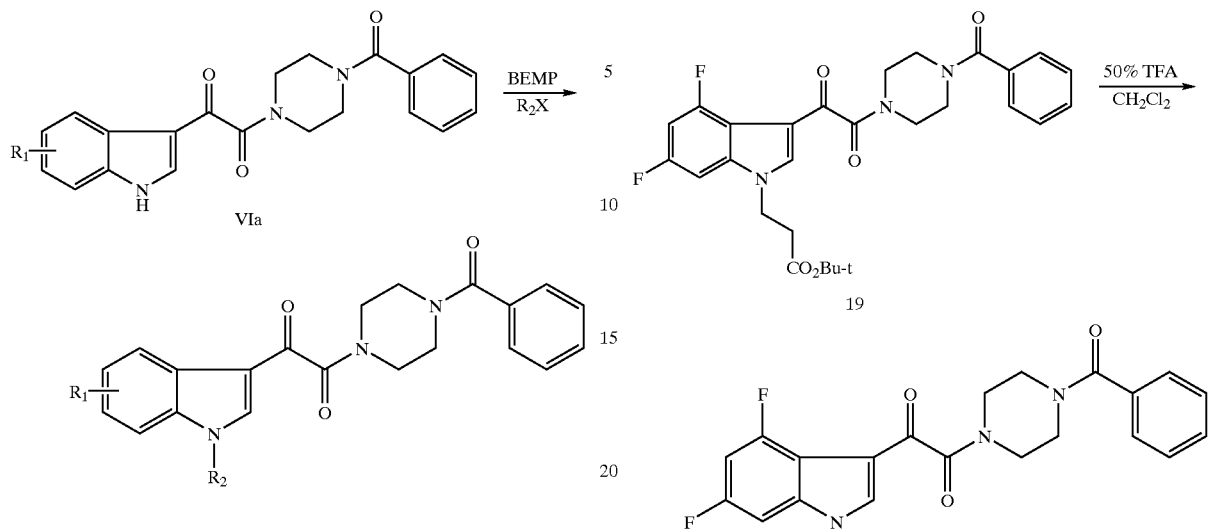

VIa

To a predried 5 ml vial was added indoles glyoxamide VIa (0.0416 μM), alkyl or aryl halide R₂X (0.0478 μM), dry DMF (2 ml) and BEMP (0.0541 μM) at rt. The reaction was shaken at 70–80° C. in a heating block under nitrogen for 4 hr. After evaporation of the solvent in vacuo, the crude compound was purified by prep HPLC and characterized as shown in Table 14.

For examples 33 and 34, the reactions were conducted in NMP and were heated to 80° C. for 16 h before purification by prep. HPLC.

Preparation of Example 19

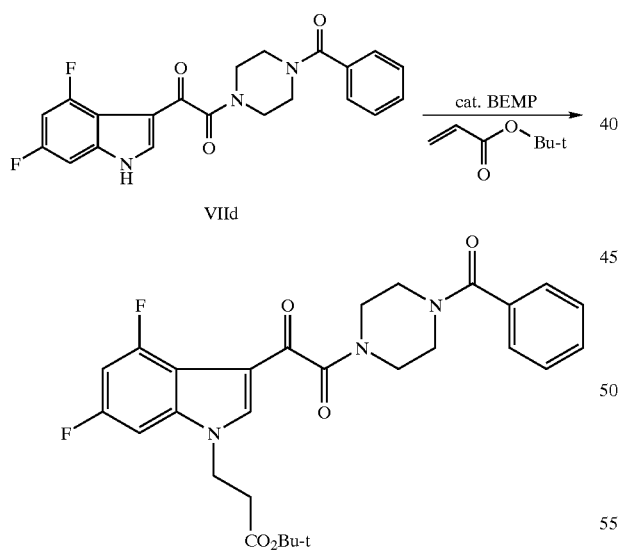

VIId

To indole glyoxamide VIId (200 mg, 0.5 mmol) in THF (1 mL) in a sealed tube was added BEMP (0.2 equiv) and t-butylacrylate (0.37 mL, 2.5 mmol). The reaction mixture was heated to 90° C. overnight. The crude product was poured into 1M HCl and was extracted with EtOAc. The organic phase was washed with sat. NaCl and dried over MgSO4, filtered and concentrated. The crude product was purified by flash chromatography (2:1 EtOAc/Hexane) to afford 195 mg of alkylated product 19.

Preparation of Example 21

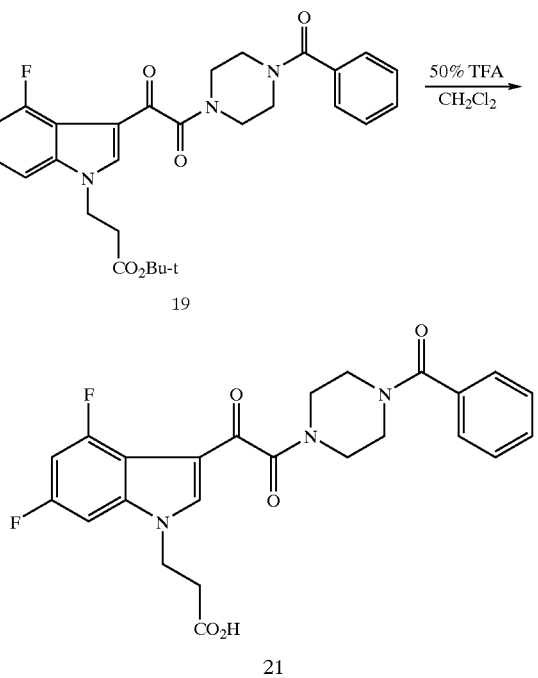

19

21

To ester 19 (956 mg) was added CH2Cl2 (4 mL) followed by TFA (4 mL). The reaction mixture was stirred at room temperature for 1 h. The solvent was removed in vacuo and the product was triturated with ether to afford acid 21 (802 mg) as a white solid.

Preparation of Example 22

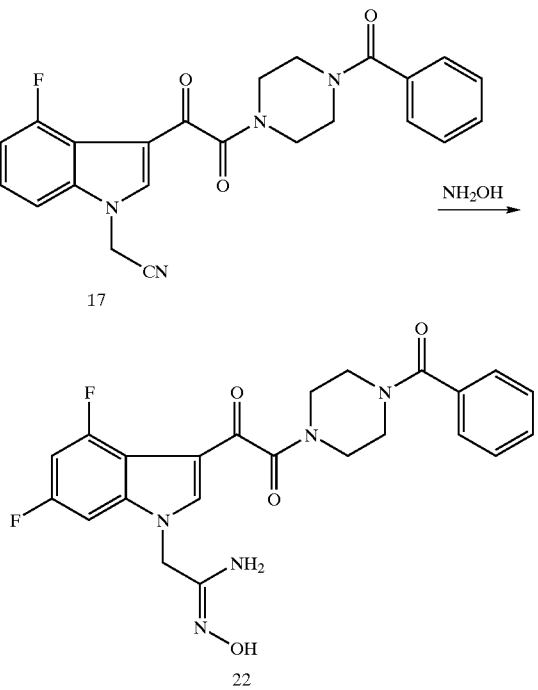

17

22

To nitrile 17 (330 mg, 0.76 mmol) in EtOH/H2O (18 mL, 2:1) was added hydroxylamine (189 mg, 2.72 mmol) followed by K2CO3 (209 mg, 1.5 mmol). The reaction mixture was heated to 65° C. overnight. The solvent was then removed in vacuo. The residue was partitioned between water and EtOAc. The organic phase was washed with brine, dried over MgSO4, filtered and concentrated. The product was then triturated with ether to afford 22 (276 mg) as a white solid.

Preparation of Example 23

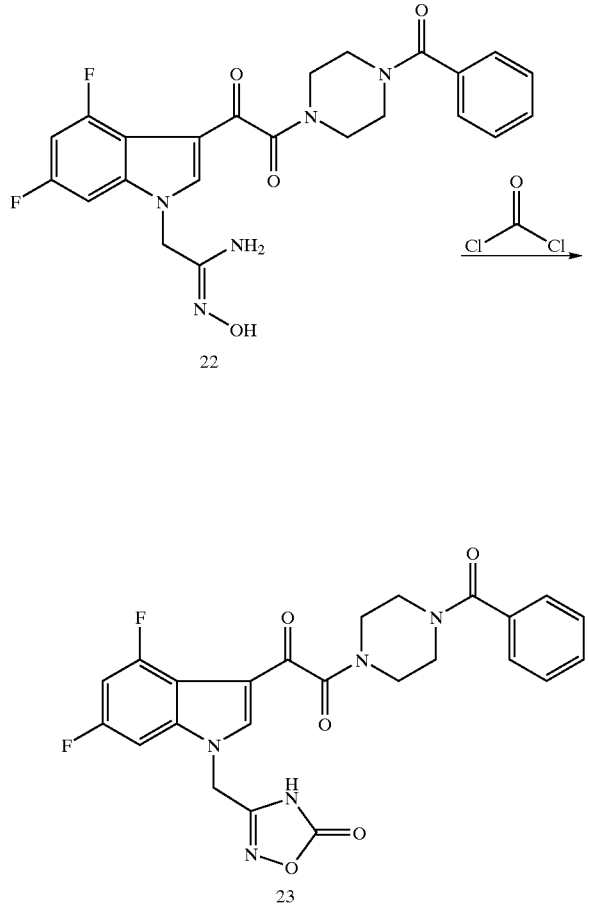

To glyoxamide 22 (100 mg, 0.21 mmol) was added toluene (1.5 mL) followed by $K_2CO_3$ (35 mg, 0.26 mmol) and phosgene in toluene (1.09 mL, 20% solution). The reaction mixture was heated to reflux for 2.5 h. The mixture was then cooled to r.t. and was stirred overnight. The product was filtered, concentrated and triturated with ether to yield 23 (89 mg) as a gold colored solid.

TABLE 14

| Example # | $R_1$ | $R_2$ | HPCL Retention Time | MS Data $(M + H)^+$ |
|---|---|---|---|---|
| 1 | H | allyl | 1.62 | 402.19 |
| 2 | H | propargyl | 1.99 | 400.16 |
| 3 | H | 3-CF3-benzyl | 1.92 | 520.22 |
| 4 | H | 4-methylbenzyl | 1.87 | 466.24 |
| 5 | H | -CH2CH2CH2-O-Ph | 1.75 | 482.20 |
| 6 | H | -CH3 | 1.52 | 376.23 |
| 7 | H | isopentyl | 1.82 | 432.30 |
| 8 | H | cyclohexylmethyl | 1.91 | 458.20 |
| 9 | H | -CH2CH=C(CH3)2 | 1.77 | 430.30 |
| 10 | H | -CH2CH(CH3)2 | 1.73 | 390.20 |

TABLE 14-continued

| Example # | R₁ | R₂ | HPCL Retention Time | MS Data (M + H)⁺ |
|---|---|---|---|---|
| 11 | H | butyl | 1.74 | 418.30 |
| 12 | 2-Methyl | —CH₃ | 1.36 | 390.15 |
| 13 | 4-Fluoro | —CH₃ | 1.24 | 394.05 |
| 14 | 4-Chloro | —CH₃ | 1.39 | 410.10 |
| 15 | 6-Fluoro | —CH₃ | 1.38 | 393.79 |
| 16 | 4,7-Difluoro | —CH₂CH₂N(CH₃)₂ | 1.16 | 469 |
| 17 | 4,7-Difluoro | —CH₂CN | 1.35 | 437 |
| 18 | 4,7-Difluoro | —CH₂C(O)N(Et)₂ | 1.49 | 511 |
| 19 | 4,7-Difluoro | —CH₂CH₂C(O)OBu-t | 1.68 | 526 |
| 20 | 4,7-Difluoro | —CH₃ | 1.47 | 412 |
| 21 | 4,7-Difluoro | —CH₂CH₂C(O)OH | 1.32 | 470 |
| 22 | 4,7-Difluoro | —CH₂C(=NOH)NH₂ | 1.18 | 470 |
| 23 | 4,7-Difluoro | —CH₂-(1,2,4-oxadiazol-5(4H)-one-3-yl) | 1.47 | 496 |
| 24 | 4-Fluoro | —CH₂CH₂N(CH₃)₂ | 1.09 | 451 |
| 25 | 4-Fluoro | —CH₂CH₂Cl | 1.40 | 442 |
| 26 | 4-Fluoro | —CH₂CH₂CH₂CO₂Et | 2.08 | 494 |
| 27 | 4-Fluoro | —(CH₂)₅CO₂Et | 2.14 | 522 |
| 28 | 4-Fluoro | —CH₂CH₂CO₂Et | 2.00 | 466 |

TABLE 14-continued

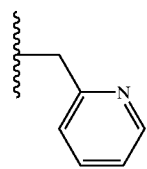

| Example # | R₁ | R₂ | HPCL Retention Time | MS Data (M + H)⁺ |
|---|---|---|---|---|
| 29 | 4-Fluoro | 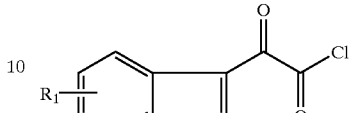 | 1.24 | 471 |
| 30 | 4-Fluoro | 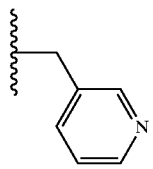 | 1.09 | 471 |
| 31 | 4-Fluoro | 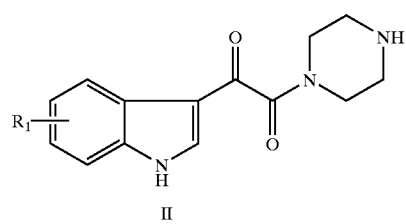 | 1.39 | 471 |
| 32 | 4-Fluoro | 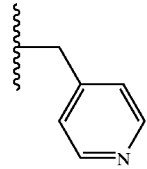 | 1.67 | 494 |
| 33 | 4-Fluoro | 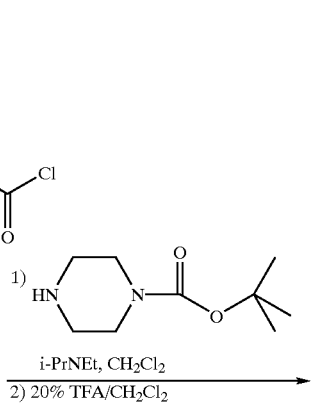 | 2.03 | 528 |
| 34 | 4-Fluoro | 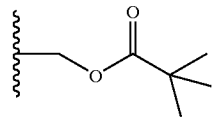 | 1.79 | 501 |

General Procedure for Preparation of Examples 35–56

Step A

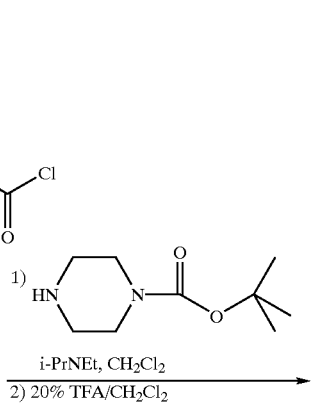

To indole-3-glyoxylyl chloride I (3 gram, 14.45 mmol) in CH₂Cl₂ at room temperature was added tert-butyl 1-piperazinecarboxylate (2.7 gram, 14.45 mmol) and diisopropylethylamine (2.76 ml, 15.9 mmol). The light-brown color solution was stirred for 2 hr at room temperature after which time LC/MS analysis indicated the completion of the reaction. The solvent was removed in vacuo and the resulting residue was diluted with ethyl acetate (250 ml) and diethylether (250 ml). The organic solution was then washed with water (100 ml×3) and brine (50 ml), dried over MgSO₄, filtered and concentrated. To the light-yellow solid was then added 30 ml of 20% trifluoroacetic acid in CH₂Cl₂. The solution was concentrated and the light-brown solid was dried in vacuo to give 3.5 g (95%) of product II. LC/MS analysis indicated this product was 100% pure and it was used for the next reaction without further purification.

Step B

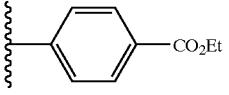

General Procedure for Preparation of Examples 35–56

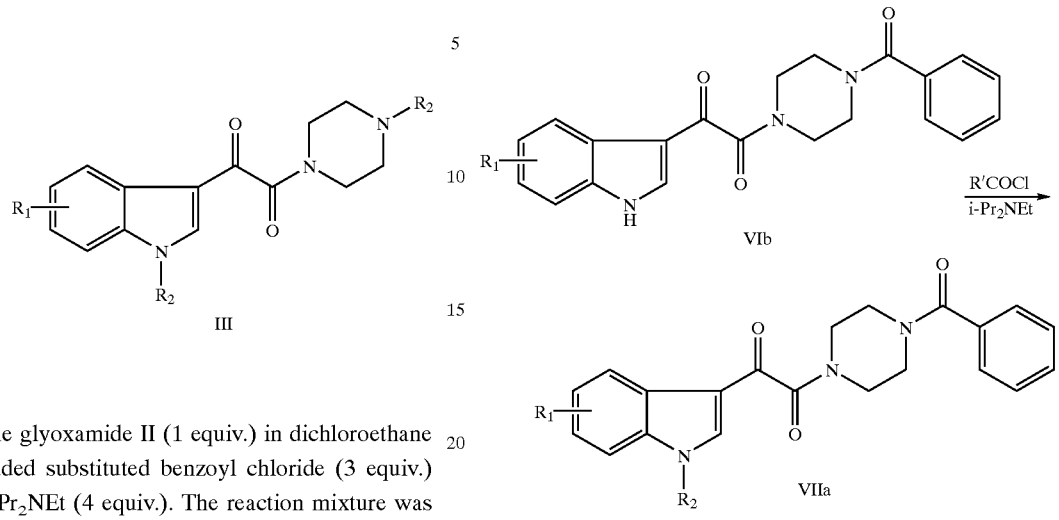

To piperazine glyoxamide II (1 equiv.) in dichloroethane (DCE) was added substituted benzoyl chloride (3 equiv.) followed by i-Pr$_2$NEt (4 equiv.). The reaction mixture was stirred at room temperature for 16 h and product III was then purified by prep HPLC.

To indole gloxamide VIb (1 equiv.) in DCE was added substituted acid chloride (3 equiv.) followed by i-Pr$_2$NEt (4 equiv.). The reaction mixture was stirred at room temperature for 16 h and product VIIa was then purified by prep HPLC.

TABLE 15

| Exp. # | R$_1$ | R$_2$ | R$_3$ | HFLC Retention Time | MS Data |
|---|---|---|---|---|---|
| 35 | H | 2-F-C$_6$H$_4$-C(O)- | 2-F-C$_6$H$_4$-C(O)- | 2.20 | 502 |
| 36 | H | 2-Cl-C$_6$H$_4$-C(O)- | 2-Cl-C$_6$H$_4$-C(O)- | 2.28 | 536 |
| 37 | H | 2-Br-C$_6$H$_4$-C(O)- | 2-Br-C$_6$H$_4$-C(O)- | 2.27 | 624 |

TABLE 15-continued

| Exp. # | R₁ | R₂ | R₃ | HPLC Retention Time | MS Data |
|---|---|---|---|---|---|
| 38 | H | 2-MeO-benzoyl | 2-MeO-benzoyl | 2.19 | 526 |
| 39 | H | 3-F-benzoyl | 3-F-benzoyl | 2.32 | 502 |
| 40 | H | 3-Cl-benzoyl | 3-Cl-benzoyl | 2.34 | 534 |
| 41 | H | 3-Br-benzoyl | 3-Br-benzoyl | 2.37 | 623 |
| 42 | H | 3-OMe-benzoyl | 3-OMe-benzoyl | 2.25 | 526 |
| 43 | H | 4-F-benzoyl | 4-F-benzoyl | 2.20 | 502 |
| 44 | H | 4-Cl-benzoyl | 4-Cl-benzoyl | 2.33 | 534 |
| 45 | H | 4-Br-benzoyl | 4-Br-benzoyl | 2.37 | 623 |

TABLE 15-continued

| Exp. # | R₁ | R₂ | R₃ | HFLC Retention Time | MS Data |
|---|---|---|---|---|---|
| 46 | H | -C(O)-C₆H₄-4-OMe | -C(O)-C₆H₄-4-OMe | 2.34 | 526 |
| 47 | H | -C(O)-Ph | -C(O)-Ph | 1.80 | 466 |
| 48 | H | -C(O)-CH₃ | -C(O)-Ph | 1.58 | 404 |
| 49 | H | -C(O)-C₆H₄-2-F | -C(O)-Ph | 1.86 | 484 |
| 50 | H | -C(O)-C₆H₄-2-Cl | -C(O)-Ph | 1.90 | 500 |
| 51 | H | -C(O)-C₆H₄-2-Br | -C(O)-Ph | 1.91 | 546 |
| 52 | H | -C(O)-C₆H₄-2-OMe | -C(O)-Ph | 1.87 | 496 |
| 53 | H | -C(O)-C₆H₄-4-OMe | -C(O)-Ph | 1.77 | 496 |
| 54 | 4-Chloro | -C(O)-Ph | -C(O)-Ph | 1.75 | 500 |

TABLE 15-continued

[Structure: Indole with R1 at positions 4-7, N-R2, 3-position bearing C(O)C(O)-piperazine-N-R3]

| Exp. # | R₁ | R₂ | R₃ | HPLC Retention Time | MS Data |
|---|---|---|---|---|---|
| 55 | 4-Fluoro | -C(O)-phenyl | -C(O)-phenyl | 1.64 | 484 |
| 56 | 4-Fluoro | -C(O)-C₆H₄-OMe (para) | -C(O)-phenyl | 1.73 | 514 |

Procedure for Preparation of Examples 57–64

To indole gloxamide VI (1 equiv.) in DCE was added chloroformate R₂OCOCl (3 equiv.) followed by i-Pr₂NEt (4 equiv.). The reaction mixture was stirred at room temperature for 16 h and carbamate VIIb was then purified by prep HPLC.

VIc + R₂OCOCl / i-Pr₂NEt → VIIb

TABLE 16

| Example # | R₁ | R₂ | HPLC Retention Time | MS Data (M+H)+ |
|---|---|---|---|---|
| 57 | 4-Choro | Phenyl | 1.82 | 516 |
| 58 | H | Phenyl | 1.77 | 482 |
| 59 | 4-Fluoro | Phenyl | 2.22 | 500 |
| 60 | 4-Fluoro | Benzyl | 2.25 | 514 |
| 61 | 7-Methyl | t-Butyl | 1.93 | 476 |
| 62 | 4-Fluoro | Methyl | 1.54 | 438 |
| 63 | 4-Fluoro | Ethyl | 1.65 | 452 |
| 64 | 4-Fluoro | t-Butyl | 1.82 | 480 |

General Procedure for Preparation of Examples
65–69

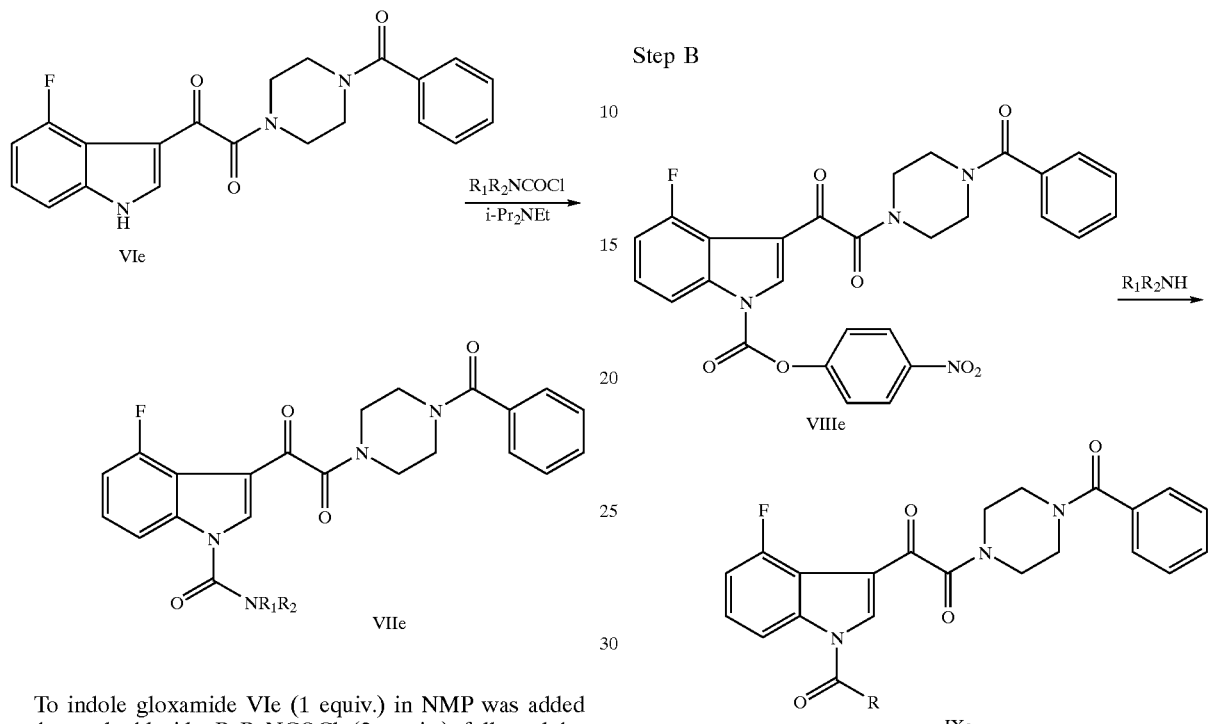

To indole gloxamide VIe (1 equiv.) in NMP was added carbamoyl chloride R₁R₂NCOCl (2 equiv.) followed by i-Pr₂NEt (4 equiv.). The reaction mixture was stirred at room temperature for 16 h and urea VIIe was then purified by prep HPLC.

General Procedure for Preparation of Examples
65–69
Step A

To indole gloxamide VIIe (1 equiv.) in DCE was added p-nitrophenylchloroformate (1.1 equiv.) followed by i-Pr₂Nt (3 equiv.). The reaction mixture was stirred at room temperature for 3 h and the crude product was used in the following reaction without further work-up or purification.

Step B

To crude p-nitrophenylcarbamate VIIe was added secondary amine R₁R₂NH. The reaction mixture was stirred for 16 h at room temperature and urea IXe was then purified by prep. HPLC.

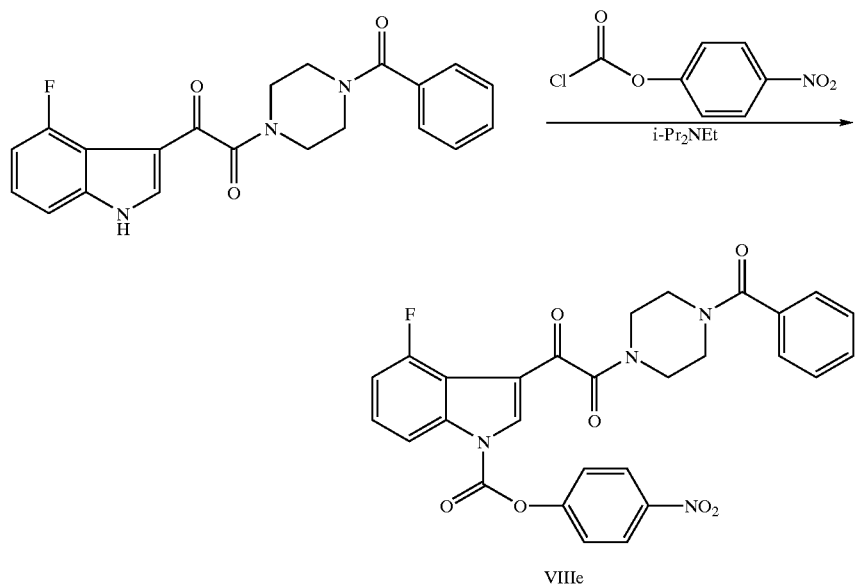

Preparation of Examples 65–69 in Table 17

VIIe $R_1NCO$ / $i-Pr_2NEt$

Xe

To indole glyoxamide VIIe (1 equiv.) in $CH_2Cl_2$ at room temperature was added isocyanate ($R_1NCO$) (2 equiv.) followed by i-Pr$_2$NEt (3 equiv.). The reaction mixture was stirred at room temperature for 18 h and the crude product Xe was purified by prep. HPLC.

TABLE 17

| Example # | R | HPLC Retention Time | MS Data (M+H)+ |
|---|---|---|---|
| 65 | N(Me)(phenyl) | 1.76 | 513 |
| 66 | morpholinyl | 1.60 | 493 |

TABLE 17-continued

| Example # | R | HPLC Retention Time | MS Data (M+H)+ |
|---|---|---|---|
| 67 | N(Me)Me | 1.58 | 451 |
| 68 | N-piperazinyl-NMe | 1.45 | 506 |
| 69 | NHEt | 1.48 | 451 |

Preparation of Examples 70–71 in Table 18

XIf $RSO_2Cl$ / $i-Pr_2NEt$

XIIf

To indole gloxamide XIf (1 equiv.) in DCE was added psulfonyl chloride (2 equiv.) followed by i-Pr$_2$NEt (3 equiv.). The reaction mixture was stirred at room temperature for 3 h and the crude product XIIf was purified by prep. HPLC.

TABLE 18

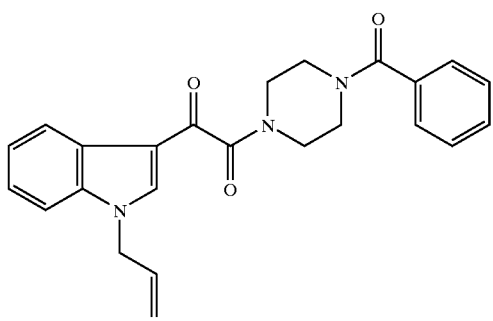

| Example # | R | HPLC Retention Time | MS Data (M+H)+ |
|---|---|---|---|
| 70 | Phenyl | 1.85 | 502 |
| 71 | Methyl | 1.69 | 440 |

Additional Analytical Data for Selected Compounds

1

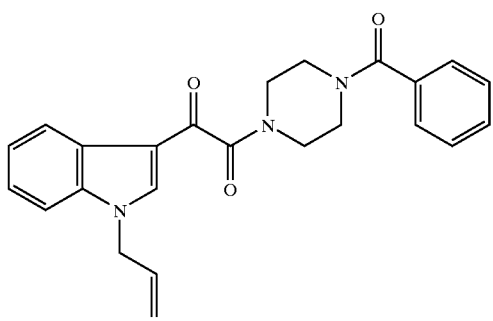

$^1$H-NMR (300 MHz, DMF-d7): δ 8.30 (s, 1H), 8.22 (d, 1H, J=7.26 Hz), 7.84 (d, 1H, J=7.26 Hz), 7.30–7.54 (m, 7H), 4.99 (s, 3H), 3.52–3.92 (m, 8H).

2

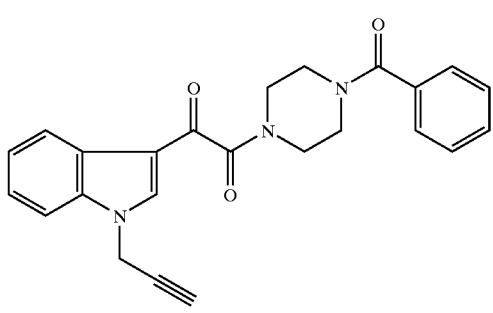

$^1$H-NMR (300 MHz, CD3OD): δ 8.28 (d, 1H, J=8.37 Hz), 8.22 (s, 1H), 7.64 (d, 1H, J=7.26), 7.27–7.56 (m, 7H), 5.16 (d, 2H, J=2.52 Hz), 3.36–4.02 (m, 8H), 3.02 (t, 1H, J=2.55 Hz).

17

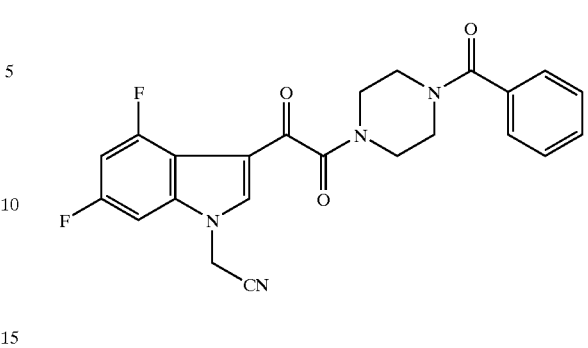

$^1$H-NMR (500 MHz, CD3Cl): δ 8.05 (s, 1H), 7.45 (br. s, 5H), 6.88–7.01 (m, 2H), 5.04 (s, 2H), 3.79 (br. m, 4H), 3.59 (br. m, 4H). Anal. Calcd for $C_{23}H_{18}F_2N_4O_3$: C 63.30; H 4.16; N 12.84; F 8.71; O 11.00. Found C 62.33; H 4.52; N 12.05. MS 437 (M+H)+.

18

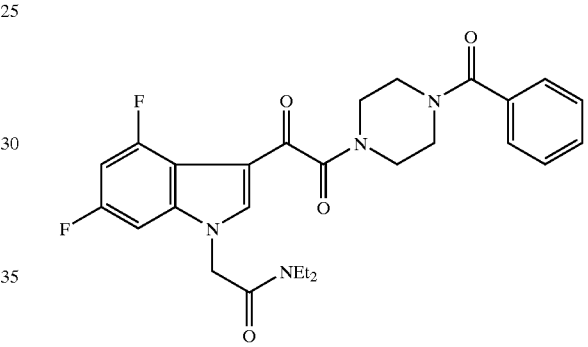

$^1$H-NMR (500 MHz, CD3Cl): δ 7.99 (s, 1H), 7.44 (br. s, 5H), 6.74–6.85 (m, 2H), 4.90 (s, 2H), 3.79 (br. m, 4H), 3.57 (br. m, 4H), 3.45 (q, J=11.4 Hz, 4H). 1.35 (t, J=11.4 Hz, 3H), 1.21 (t, J=11.4 Hz, 3H). Anal. Calcd for $C_{27}H_{28}F_2N_4O_4$: C 63.52; H 5.54; N 10.97. Found C 62.75; H 5.54; N 10.80.

20

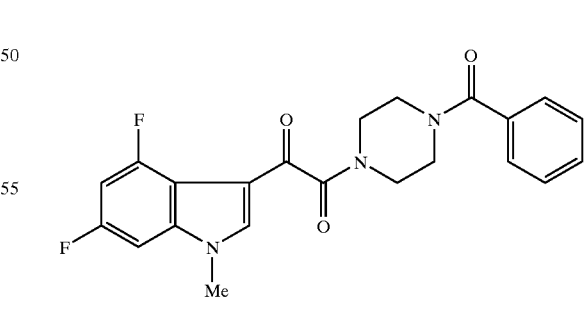

$^1$H-NMR (500 MHz, DMSO-d6): δ 8.32 (s, 1H), 7.44 (br. s, 6H), 7.12 (app. t, 1H), 3.87 (s, 3H), 3.2–3.7 (br. m, 8H). MS 412 (M+H)+ Anal. for $C_{22}H_{19}F_2N_3O_3$: C 64.23; H 4.65; N 10.1. Found $C_{64.58}$; H 4.74; N 9.63.

22

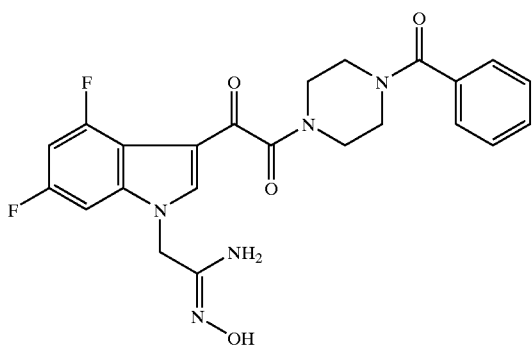

$^1$H-NMR (500 MHz, DMSO-d6): δ 8.40 (s, 1H), 7.44 (br. s, 6H), 7.14 (app. t, 1H), 5.01 (br. s, 2H), 3.2–3.7 (br. m). MS 470 (M+H)$^+$ Anal. for $C_{23}H_{21}F_2N_5O_4$: C 58.85; H 4.51; N 14.92. Found C 58.17; H 5.06; N 13.85.

23

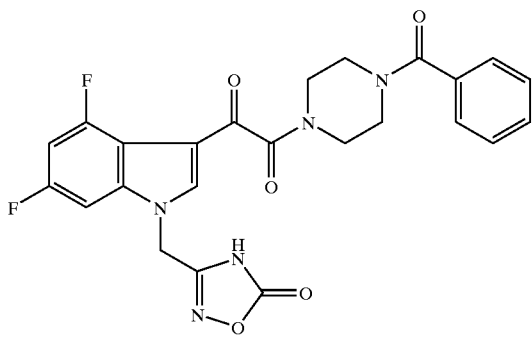

$^1$H-NMR (500 MHz, DMSO-d6): δ 8.40 (s, 1H), 7.4–7.55 (m, 6H), 7.16 (app. t, 1H), 5.61 (br. s, 2H), 3.2–3.7 (br. m). MS 496 (M+H)$^+$ The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

| Abbreviations | |
|---|---|
| TFA | Trifluoroacetic Acid |
| P-EDC | Polymer supported 1-(3-dimethylaminopropyl)-3-ethylcarbodiimide |
| EDC | 1-(3-dimethylaminopropyl)-3-ethylcarbodiimide |
| DCE | 1,2-Dichloroethane |
| DMF | N,N-dimethylformamide |
| THF | Tetrahydrofuran |
| NMP | N-methylpyrrolidone |
| BEMP | 2-tert-Butylimino-2-diethylamino-1,3-dimethyl-perhydro-1,3,2-diazaphosphorine |

What is claimed is:
1. A compound of formula I, including pharmaceutically-acceptable salts thereof,

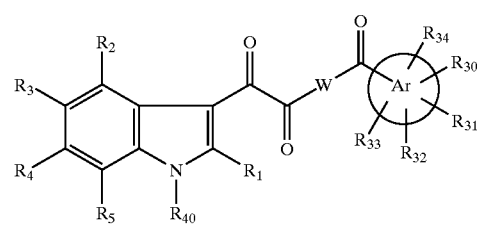

wherein:
$R_1$, $R_2$, $R_3$, $R_4$ and $R_5$ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, halogen CN, nitro, COOR$_6$ or XR$_7$, each of said alkyl and cycloalkyl being optionally substituted with one to three same or different halogen, amino, OH, CN or NO$_2$;

$R_6$ is H, $C_1$–$C_6$ alkyl, or $C_3$–$C_6$ cycloalkyl, benzyl, each of said alkyl, cycloalkyl and benzyl being optionally substituted with one to three same or different halogen, amino, OH, CN or NO$_2$;

X is O, S or NR$_6$R$_7^+$:
$R_7$ is H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl or C(O)R$_8$, each of said alkyl and cycloalkyl being optionally substituted with one to three same or different halogen, OH, amino, CN or NO$_2$;

$R_8$ is H, $C_1$–$C_6$ alkyl or $C_3$–$C_6$ cycloalkyl;
—W— is

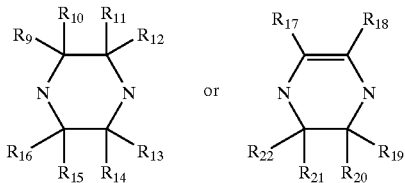

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, $CR_{23}R_{24}OR_{25}$, $COR_{26}$, $COOR_{27}$ or $C(O)NR_{28}R_{29}$, each of said alkyl and cycloalkyl being optionally substituted with one to three same or different halogen, amino, OH, CN or $NO_2$;

$R_{23}$, $R_{24}$, $R_{25}$, $R_{26}$, $R_{27}$, $R_{28}$, $R_{29}$ are each independently H, $C_1$–$C_6$ alkyl, $C_3$–$C_6$ alkenyl, $C_3$–$C_6$ cycloalkenyl or $C_2$–$C_6$ alkynyl;

Ar is a 4–7 membered aromatic ring which may contain one to five heteroatoms independently selected from the group consisting of O, S, N or $NR_6$, wherein said aromatic ring is optionally fused to group B;

B is an aromatic group selected from the group consisting of phenyl, 1-naphthyl, 2-naphthyl, indenyl, azulenyl, fluorenyl, and anthracenyl; or a heteroaryl group selected from the group consisting of 2-furyl, 3-furyl, 2-thienyl, 3-thienyl, 2-pyridyl, 3-pyridyl, 4-pyridyl, pyrrolyl, oxaz thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, and 1,3,5-trithianyl; or the resulting fused aromatic ring with B is indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl;

B and said 4–7 membered aromatic ring may each independently contain one to five substituents which are each independently selected from $R_{30}$ $R_{31}$, $R_{32}$, $R_{33}$ or $R_{34}$;

$R_a$ and $R_b$ are each independently H, $C_{1-6}$ alkyl or phenyl;

Z is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and p is 1–2;

$R_{30}$ $R_{31}$, $R_{32}$, $R_{33}$, and $R_{34}$ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, halogen, CN, nitro, $C(O)R_{35}$, $COXR_{36}$, hydroxyl, hydroxymethyl, trifluoromethyl, trifluoromethoxy, O-benzyl, O-phenyl, $OC(O)C_{1-6}$ alkyl, $SC(O)C_{1-6}$ alkyl, $S(O)_m$ $C_{1-6}$ alkyl, $S(O)_2$ $NR_aR_b$, amino, O-Z, $CH_2$—$(CH_2)_p$-Z, O—$(CH_2)_p$-Z, $(CH_2)_r$—O-Z, CH=CH-Z or $XR_{37}$, each of said alkyl and cycloalkyl being optionally substituted with one to three same or different halogen, amino, OH, CN or $NO_2$;

m is 0–2;

$R_{35}$ and $R_{36}$ are each independently H, $C_1$–$C_6$ alkyl or $C_3$–$C_6$ cycloalkyl;

$R_{37}$ is H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, $C(O)R_{38}$ or $C(O)OR_{39}$, each of said alkyl and cycloalkyl being optionally substituted with one to three same or different halogen, amino, OH, CN or $NO_2$;

$R_{38}$, $R_{39}$ are each independently H, $C_1$–$C_6$ alkyl or $C_3$–$C_6$ cycloalkyl, each of said alkyl and cycloalkyl being optionally substituted with one to three same or different halogen, amino, OH, CN or $NO_2$; provided $R_{39}$ is not H;

$R_{40}$ is $(CH_2)_n$—Y, where n is 0–6;

Y is selected from:
(1) H, $C_{1-6}$ alkyl, $C_{3-6}$ cycloalkyl, $C_{2-6}$ alkenyl, $C_{3-6}$ cycloalkenyl, $C_{2-6}$ alkynyl, halogen, CN, nitro, Ar, $COOR_6$, COOAr, —$CONR_aR_b$, $TR_6$, $NR_aR_b$, —$NC(O)NR_aR_b$, —$OC(O)R_6$, —C[N($R_a$)$_2$]=N-T-$R_b$, $XR_6$, —$C(O)R_6$, —C(O)Ar, —$S(O)R_a$ or —$S(O)_2R_a$, provided when Y is —$S(O)R_a$ or —$S(O)_2R_a$ then $R_a$ is not H; and (2) a 4–7 membered heterocyclic ring, optionally substituted with $R_6$, which may contain 1–3 heteroatoms selected from the group consisting of O, S, SO, $SO_2$, N, and $NR_{41}$, wherein $R_{41}$ is selected from the group consisting of hydrogen, ($C_1$–$C_4$)-straight or branched alkyl, ($C_2$–$C_4$)-straight or branched alkenyl or alkynyl;

T is S or O;

provided $R_1$–$R_5$, $R_9$–$R_{16}$ and $R_{30}$–$R_{34}$ are not all H at the same time and Ar is phenyl; and provided $R_1$–$R_5$, $R_9$–$R_{16}$ and $R_{30}$–$R_{34}$ are not all H at the same time and Ar is 2-furyl.

2. A compound of claim 1 wherein Ar is phenyl, furyl, isoxazolyl, thiophenyl, pyrazolyl, pyridyl, benzofuryl, benzothiophenyl, indolyl, pyrazinyl, thiazolyl, imidazolyl, thiadiazolyl.

3. A compound of claim 1 wherein:

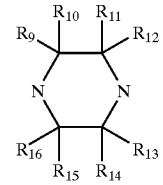

W is $R_9$, $R_{10}$, $R_{11}$, $R_{12}$, $R_{13}$, $R_{14}$, and $R_{15}$ are each H; and $R_{16}$ is methyl.

4. A compound of claim 1 wherein:

$R_2$ is H, fluoro or methoxy.

5. A compound of claim 1 wherein:

$R_1$, $R_3$ and $R_4$ are each H.

6. A pharmaceutical formulation which comprises an antiviral effective amount of a compound as claimed in any of claims 1–5 and a pharmaceutically acceptable carrier.

7. The pharmaceutical formulation of claim 6, useful for treating infection by HIV, which additionally comprises an antiviral effective amount of an AIDS treatment agent selected from the group consisting of:

(a) an AIDS antiviral agent;
(b) an anti-infective agent;
(c) an immunomodulator; and
(d) HIV entry inhibitors.

8. A method for treating mammals infected with a virus, comprising administering to said mammal an antiviral effective amount of a compound of formula II, or pharmaceutically acceptable salts thereof,

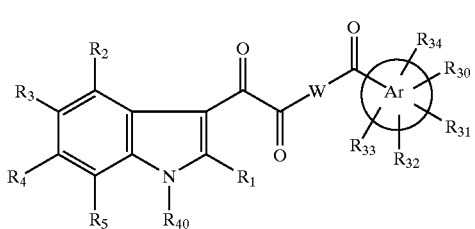

wherein:
R₁, R₂, R₃, R₄ and R₅ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, halogen, CN, nitro, $COOR_6$ or $XR_7$, each of said alkyl and cycloalkyl being optionally substituted with one to three same or different halogen, amino, OH, CN or $NO_2$;

$R_6$ is H, $C_1$–$C_6$ alkyl, or $C_3$–$C_6$ cycloalkyl, benzyl, each of said alkyl, cycloalkyl and benzyl being optionally substituted with one to three same or different halogen, amino, OH, CN or $NO_2$;

X is O, S or $NR_6R_7^+$;

$R_7$ is H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl or $C(O)R_8$, each of said alkyl and cycloalkyl being optionally substituted with one to three same or different halogen, OH, amino, CN or $NO_2$;

$R_8$ is H, $C_1$–$C_6$ alkyl or $C_3$–$C_6$ cycloalkyl;

—W— is

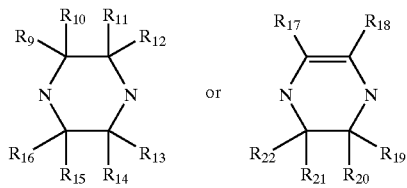

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ each independently H $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, $CR_{23}R_{24}OR_{26}$, $COOR_{27}$ or $C(O)NR_{28}R_{29}$, each of said alkyl and cycloalkyl being optionally substituted with one to three same or different halogen, amino, OH, CN or $NO_2$;

$R_{23}$, $R_{24}$, $R_{25}$, $R_{26}$, $R_{27}$, $R_{28}$, $R_{29}$ are each independently H, $C_1$–$C_6$ alkyl, $C_3$–$C_6$ alkenyl, $C_3$–$C_6$ cycloalkenyl or $C_2$–$C_6$ alkynyl;

Ar is a 4–7 membered aromatic ring which may contain one to five heteroatoms independently selected from the group consisting of O, S, N or $NR_6$, wherein said aromatic ring is optionally fused to group B;

B is an aromatic group selected from the group consisting of phenyl, 1-naphthyl, 2-naphthyl, indenyl, azulenyl, fluorenyl, and anthracenyl; or a heteroaryl group selected from the group consisting of 2-furyl, 3-furyl, 2-thienyl, 3-thienyl, 2-pyridyl, 3-pyridyl, 4-pyridyl, pyrrolyl, oxaz thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, and 1,3,5-trithianyl; or the resulting fused aromatic ring with B is indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl;

B and said 4–7 membered aromatic ring may each independently contain one to five substituents which are each independently selected from $R_{30}$ $R_{31}$, $R_{32}$, $R_{33}$ or $R_{34}$;

$R_a$ and $R_b$ are each independently H, $C_{1-6}$ alkyl or phenyl;

Z is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and p is 1–2;

$R_{30}$ $R_{31}$, $R_{32}$, $R_{33}$, and $R_{34}$ are each independently H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, halogen, CN, nitro, $C(O)R_{35}$, $COXR_{36}$, hydroxyl, hydroxymethyl, trifluoromethyl, trifluoromethoxy, O-benzyl, O-phenyl, $OC(O)C_{1-6}$ alkyl, $SC(O)C_{1-6}$ alkyl, $S(O)_m$ $C_{1-6}$ alkyl, $S(O)_2$ $NR_aR_b$, amino, O-Z, $CH_2$-$(CH_2)_p$-Z, O—$(CH_2)_p$-Z, $(CH_2)_t$—O-Z, CH=CH-Z or $XR_{37}$, each of said alkyl and $XR_{37}$, each of said alkyl and cycloalkyl being optionally substituted with one to three same or different halogen, amino, OH, CN or $NO_2$;

m is 0–2;

$R_{35}$ and $R_{36}$ are each independently H, $C_1$–$C_6$ alkyl or $C_3$–$C_6$ cycloalkyl;

$R_{37}$ is H, $C_1$–$C_6$ alkyl, $C_3$–$C_6$ cycloalkyl, $C_2$–$C_6$ alkenyl, $C_3$–$C_6$ cycloalkenyl, $C_2$–$C_6$ alkynyl, $C(O)R_{38}$ or $C(O)OR_{39}$, each of said alkyl and cycloalkyl being optionally substituted with one to three same or different halogen, amino, OH, CN or $NO_2$;

$R_{38}$, $R_{39}$ are each independently H, $C_1$–$C_6$ alkyl or $C_3$–$C_6$ cycloalkyl, each of said alkyl and cycloalkyl being optionally substituted with one to three same or different halogen, amino, OH, CN or $NO_2$; provided $R_{39}$ is not H;

$R_{40}$ is $(CH_2)_n$—Y, where n is 0–6;

Y is selected from:
(1) H, $C_{1-6}$ alkyl, $C_{3-6}$ cycloalkyl, $C_{2-6}$ alkenyl, $C_{3-6}$ cycloalkenyl, $C_{2-6}$ alkynyl, halogen, CN, nitro, Ar, $COOR_6$, COOAr, —$CONR_aR_b$, $TR_6$, $NR_aR_b$, —$NC(O)NR_aR_b$, —$OC(O)R_6$, —$C[N(R_a)_2]$=N-T-$R_b$, $XR_6$, —$C(O)R_6$, —$C(O)Ar$, —$S(O)R_a$ or —$S(O)_2R_a$, provided when Y is —$S(O)R_a$ or —$S(O)_2R_a$ then $R_a$ is not H; and
(2) a 4–7 membered heterocyclic ring, optionally substituted with $R_6$, which may contain 1–3 heteroatoms selected from the group consisting of OS, SO, $SO_2$, N, and $NR_{41}$, wherein $R_{41}$ is selected from the group consisting of hydrogen, ($C_1$–$C_4$)-straight or branched alkyl, ($C_2$–$C_4$)-straight or branched alkenyl or alkynyl; and T is S or O.

9. The method of claim 8 wherein the virus is HIV.

10. The method of claim 8, wherein Ar is phenyl, furyl, isoxazolyl, thiophenyl, pyrazolyl, pyridyl, benzofuryl, benzothiophenyl, indolyl, pyrazinyl, thiazolyl, imidazolyl, thiadiazolyl.

11. The method of claim 8, wherein W is
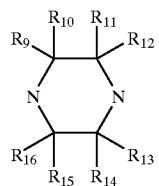
$R_9$, $R_{10}$, $R_{11}$, $R_{12}$, $R_{13}$, $R_{14}$, and $R_{15}$ are each H; and $R_{16}$ is methyl.
12. The method of claim 8, where $R_2$ is H, fluoro or methoxy.
13. The method of claim 8, wherein $R_1$, $R_3$ and $R_4$ are each H.
* * * * *